(12) United States Patent
Mehrara et al.

(10) Patent No.: US 11,583,523 B2
(45) Date of Patent: *Feb. 21, 2023

(54) COMPOSITIONS AND METHODS FOR TREATMENT OF EDEMA

(71) Applicant: Memorial Sloan Kettering Cancer Center, New York, NY (US)

(72) Inventors: Babak Mehrara, Chappaqua, NY (US); Jason Gardenier, Altona, NY (US); Ira Savetsky, Cedarhurst, NY (US); Omer Aras, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/950,652

(22) Filed: Nov. 17, 2020

(65) Prior Publication Data

US 2021/0069164 A1   Mar. 11, 2021

Related U.S. Application Data

(63) Continuation of application No. 16/277,942, filed on Feb. 15, 2019, now Pat. No. 10,874,651, which is a continuation of application No. 15/549,156, filed as application No. PCT/US2016/016680 on Feb. 5, 2016, now Pat. No. 10,251,871.

(60) Provisional application No. 62/112,273, filed on Feb. 5, 2015.

(51) Int. Cl.

| | | |
|---|---|---|
| *A61K 31/4412* | (2006.01) | |
| *A61P 7/10* | (2006.01) | |
| *A61K 38/13* | (2006.01) | |
| *A61K 31/436* | (2006.01) | |
| *A61K 9/00* | (2006.01) | |
| *A61K 47/10* | (2017.01) | |
| *A61K 9/06* | (2006.01) | |
| *A61K 45/06* | (2006.01) | |
| *A61K 31/4418* | (2006.01) | |
| *A61K 31/277* | (2006.01) | |
| *A61K 31/401* | (2006.01) | |
| *A61K 31/42* | (2006.01) | |

(52) U.S. Cl.
CPC ........ *A61K 31/4412* (2013.01); *A61K 9/0014* (2013.01); *A61K 9/06* (2013.01); *A61K 31/277* (2013.01); *A61K 31/401* (2013.01); *A61K 31/42* (2013.01); *A61K 31/436* (2013.01); *A61K 31/4418* (2013.01); *A61K 38/13* (2013.01); *A61K 45/06* (2013.01); *A61K 47/10* (2013.01); *A61P 7/10* (2018.01)

(58) Field of Classification Search
CPC .............................. A61K 31/4412; A61P 7/10
See application file for complete search history.

(56) References Cited

U.S. PATENT DOCUMENTS 10,874,651 B2 * 12/2020 Mehrara ............... A61K 31/277
2008/0161361 A1 *  7/2008 Wu ........................ A61P 39/00
514/345

OTHER PUBLICATIONS

Kim et al. Cancer Res. Treat., 2015, vol. 47, No. 3, pp. 416-423 (Published Online Nov. 17, 2014) (Year: 2015).*
Reitsma W et al., Penile and scrotal lympedema as an unusual presentation of Crohn's Disease: case report and review of the literature, Lymphology 45:37-41; 2012.
Sackett DD et al., Isolated penile lymphedema in adolescent male: a case of metastatic Crohn's disease, J. Ped. Urol. 8(5):e55-e58; 2012.

* cited by examiner

*Primary Examiner* — James D. Anderson
(74) *Attorney, Agent, or Firm* — Grimes & Yvon LLP

(57) ABSTRACT

Provided are pharmaceutical compositions and methods of treating or preventing edema, using an anti-T cell agent, an anti-TGF-β1 agent, or an anti-angiotensin agent, preferably a combination of at least two such agents. The pharmaceutical compositions can be formulated for systemic or local administration, and are preferably administered topically.

16 Claims, 53 Drawing Sheets

FIGURE 31
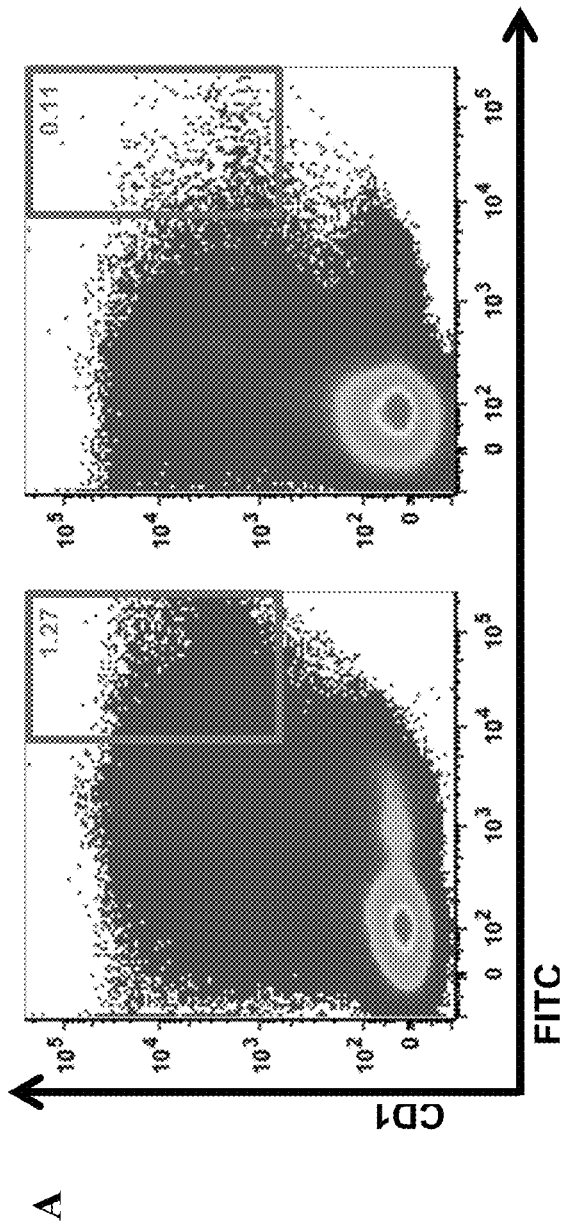
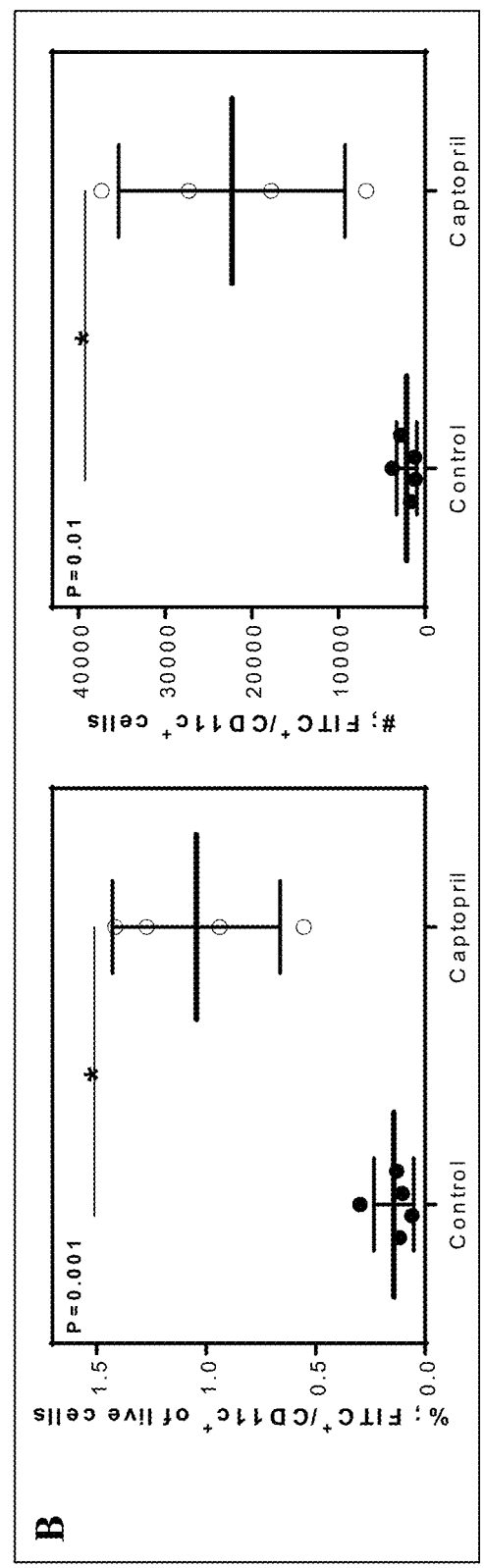

FIGURE 32
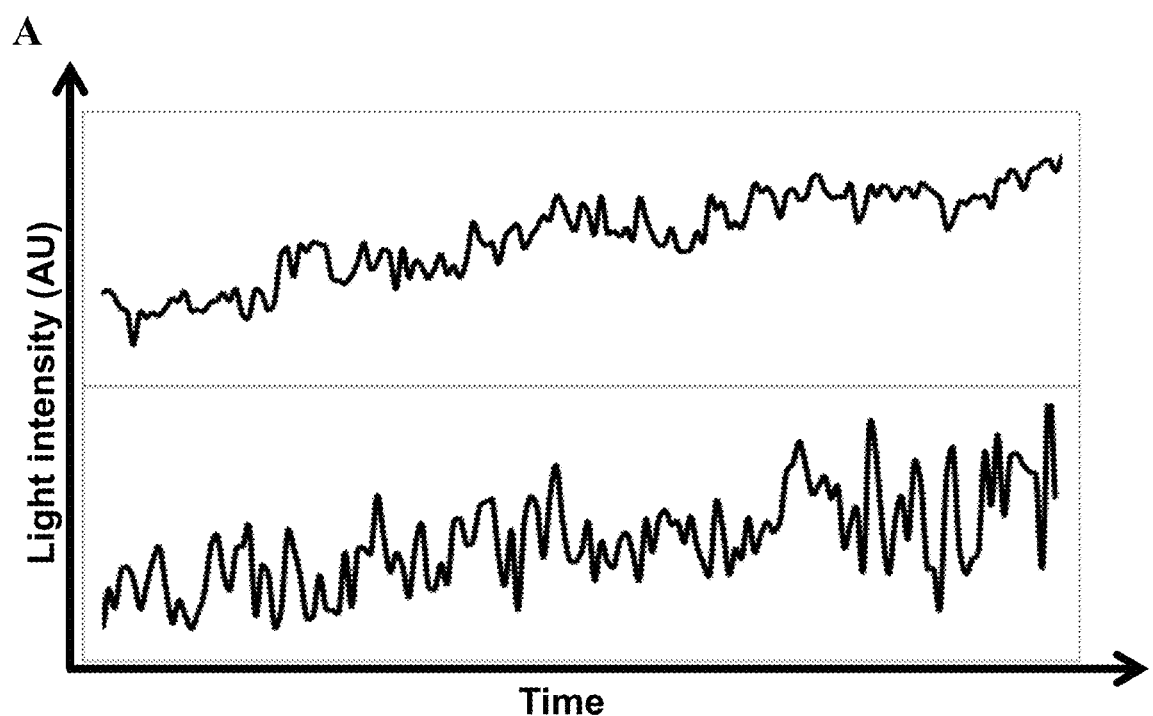
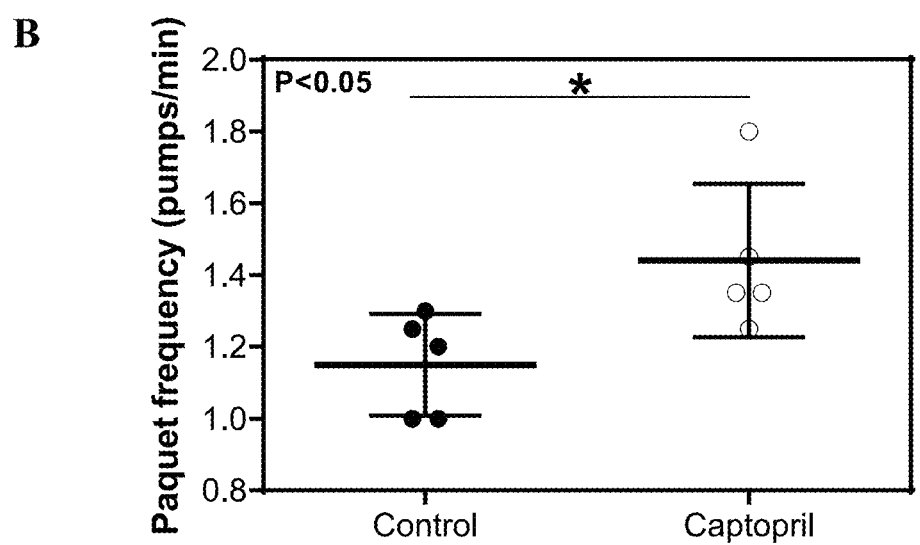

FIGURE 33
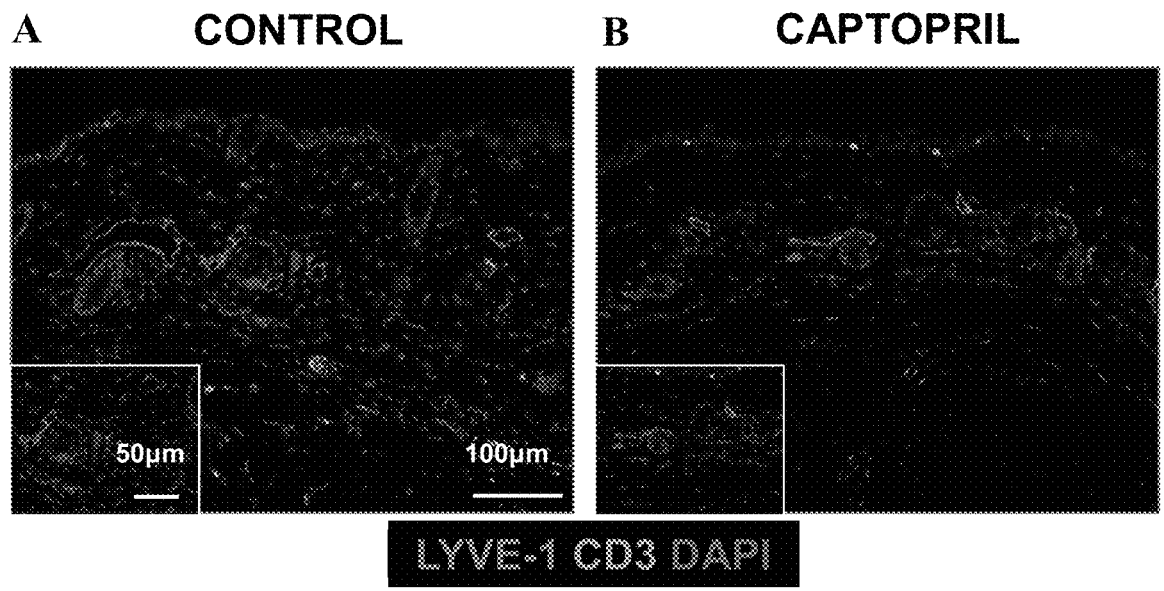
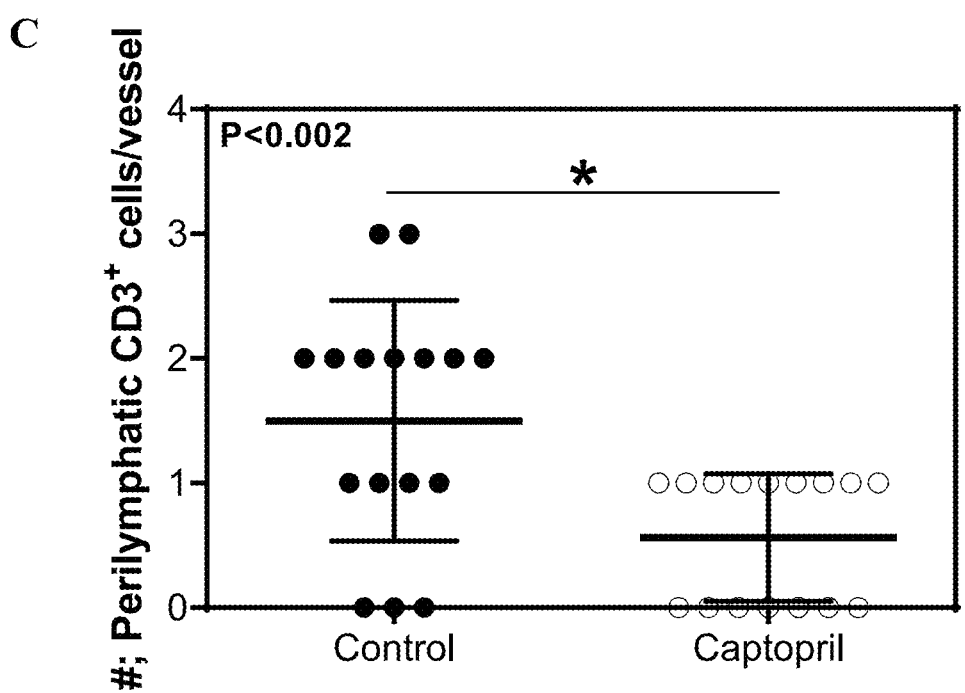

FIGURE 34
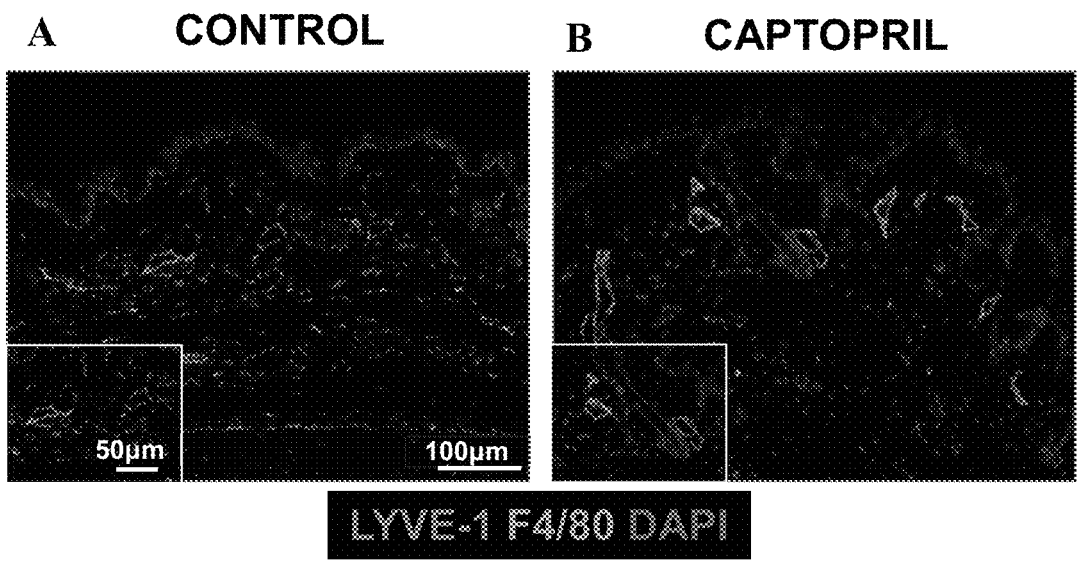
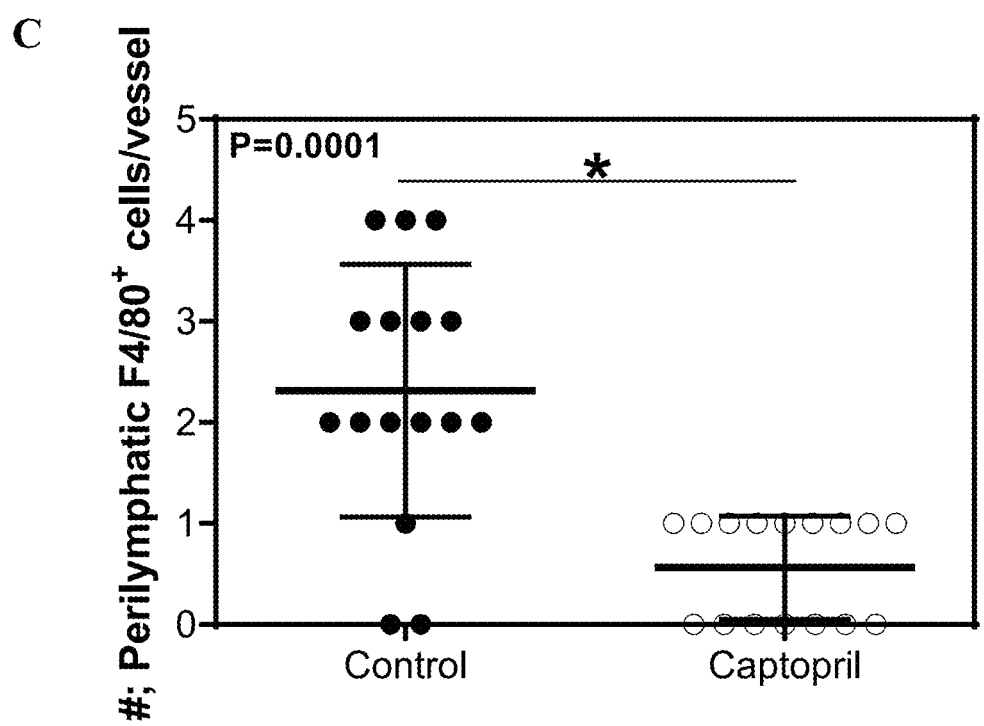

FIGURE 35
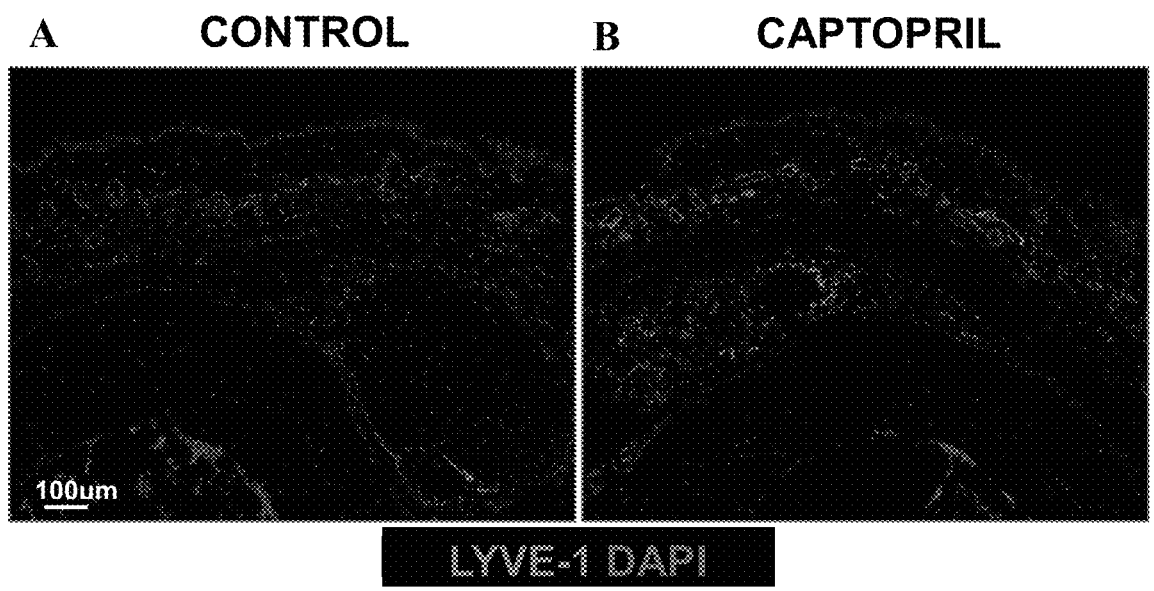
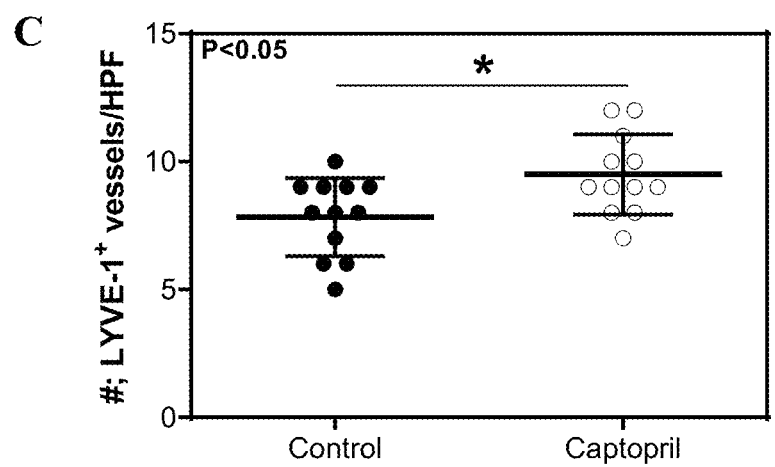

FIGURE 40
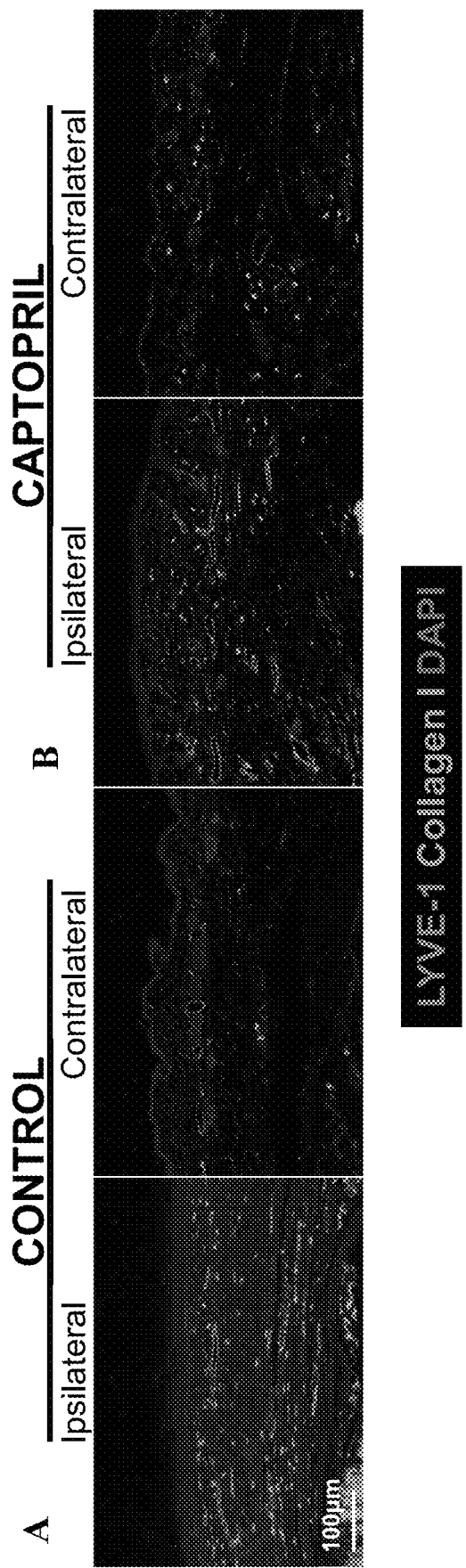
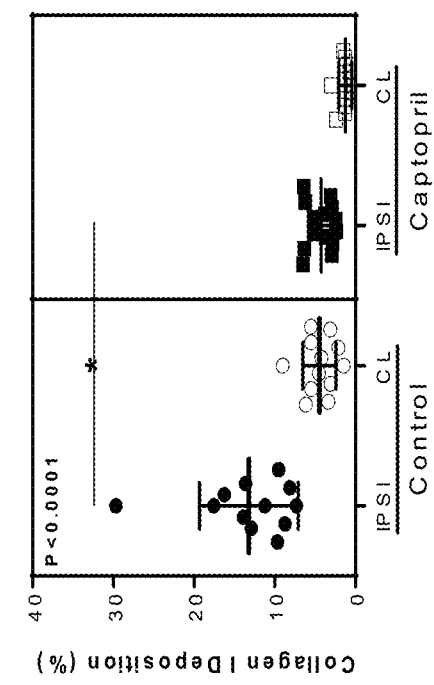

FIGURE 46
A   CONTROL      CAPTOPRIL
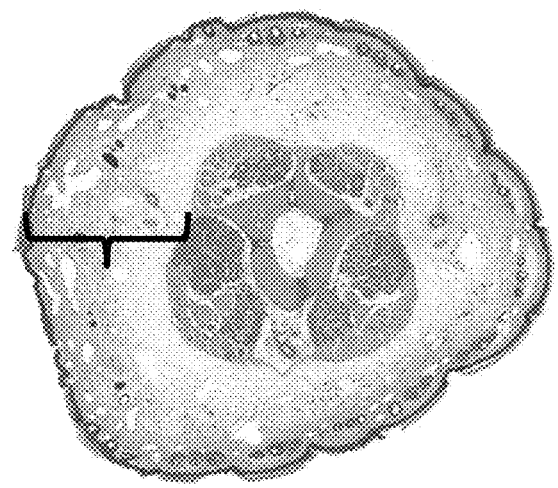
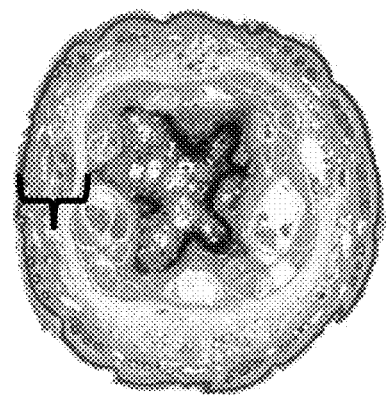
B
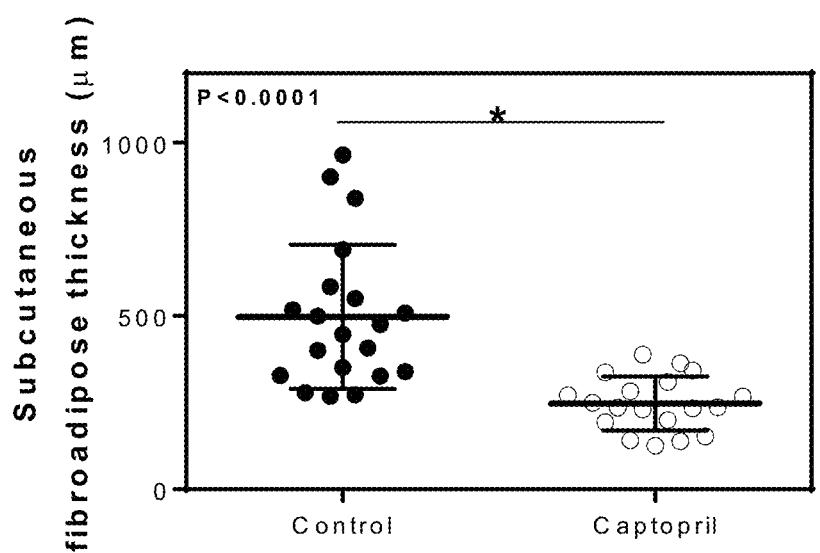

FIGURE 49
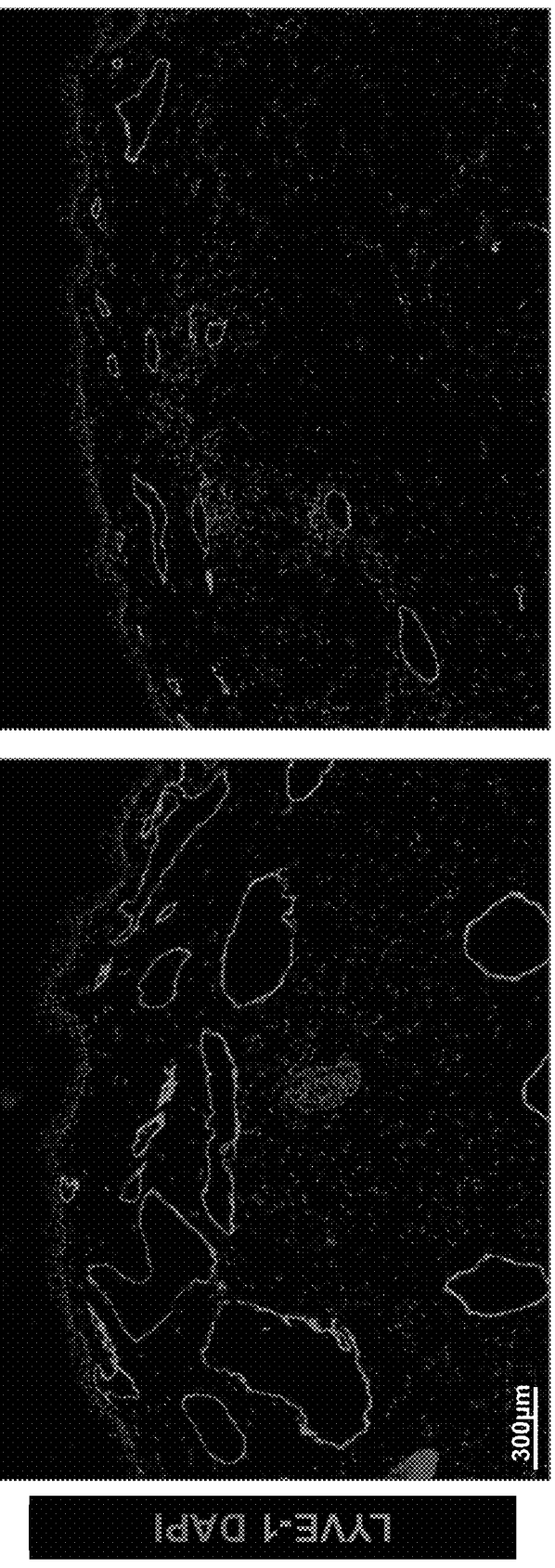
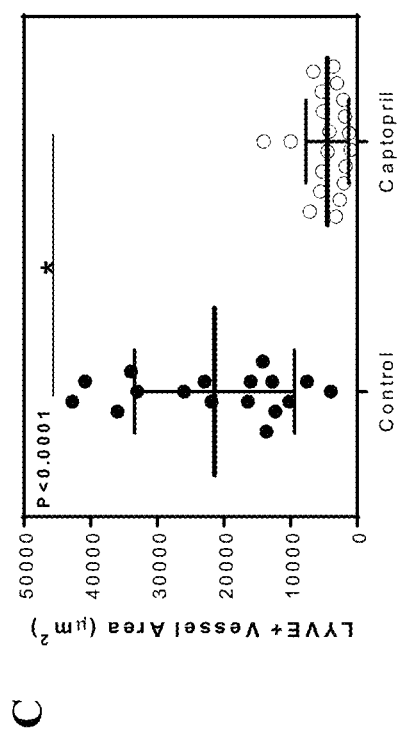

COMPOSITIONS AND METHODS FOR TREATMENT OF EDEMA

CROSS-REFERENCE TO RELATED APPLICATIONS

This application is a continuation of pending U.S. application Ser. No. 16/277,942, filed on Feb. 15, 2019, which is a continuation of U.S. application Ser. No. 15/549,156, filed on Aug. 5, 2017, now U.S. Pat. No. 10,251,871, which is the national stage under 35 U.S.C. 371 of International Application No. PCT/US2016/016680, filed on Feb. 5, 2016, which claims the benefit of priority of U.S. Provisional Patent Application No. 62/112,273, filed on Feb. 5, 2015, the entire contents of all of which are hereby incorporated by reference.

STATEMENT OF GOVERNMENT SUPPORT

This invention was made with government support under grant numbers HL111130 and CA008748, awarded by the National Institutes of Health. The government has certain rights in the invention.

COPYRIGHT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

INCORPORATION BY REFERENCE

For countries that permit incorporation by reference, all of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

BACKGROUND

Lymphedema is a chronic debilitating disease that in the United States and Western countries occurs most frequently as a complication of cancer treatment. In this setting, lymphedema occurs as a result of iatrogenic injury to the lymphatic system most commonly after lymph node dissection but also as a result of wide skin excisions and adjuvant therapy with radiation. Purushotham et al., *J. Cin. Oncol.* 23:4312-4321 (2005); Szuba et al., *Cancer* 95:2260-2267 (2002); Tsai et al., *Ann. Surg. Oncol.* 16:1959-72 (2009). It is estimated that as many as 1 in 3 patients who undergo lymph node dissection will go on to develop lymphedema and conservative estimates suggest that as many as 50,000 new patients are diagnosed annually. DiSipio et al., *Lancet Oncol.* 14:500-515 (2013); Petrek et al., *Cancer* 83:2776-2781 (1998). Because lymphedema is a life-long disease with no cure, the number of affected individuals is increasing annually with current estimates ranging between 5-6 million Americans (Rockson et al., *Ann. NY Acad. Sci.* 1131:147-154 (2008)) and over 200 million people worldwide. It is likely that this number will continue to increase in the future since the development of lymphedema is nearly linearly related with cancer survivorship, and because the prevalence of known risk factors for lymphedema, such as obesity and radiation, is rising. Erickson et al., *J. Natl. Cancer Inst.* 93:96-111 (2001).

Lymphedema is disfiguring and debilitating; patients have chronic swelling of the affected extremity, recurrent infections, limited mobility, and decreased quality of life. Hayes et al., *Cancer* 118:2237-2249 (2012). In addition, once lymphedema develops it is usually progressive. Despite the fact that lymphedema is common and highly morbid, there is currently no cure, and treatment is palliative with a goal of preventing disease progression rather than restoration of lymphatic function. Velanovich et al., *Am. J. Surg.* 177:184-187 (1999); Beaulac et al., *Arch. Surg.* 137; 1253-1257 (2002). As a result, patients are required to wear tight, uncomfortable garments for the rest of their lives, in an effort to prevent lymphatic fluid buildup in the affected extremity, and to undergo intense and time consuming physical therapy treatments. Koul et al., *Int. J. Radiat. Oncol. Biol. Phys.*, 67:841-846 (2007). In addition, despite on-going chronic care, some patients still have severe progression of their disease with increasing swelling and frequent infections in the lymphedematous limb. Currently there is no known pharmacologic therapy that can halt progression or promote resolution of lymphedema. Cormier et al., *Ann. Surg. Oncol.* 19:642-651 (2012). Development of targeted treatments for lymphedema is therefore an important goal and is an unmet biomedical need.

Recent studies have shown that fibrosis is not only a clinical hallmark of lymphedema, but also a key pathologic regulator of the disease. Cheville et al., *Semin. Radiat. Oncol.* 13:214-225 (2003); Mihara et al., *PLoS One* 7:e41126 (2012); Rasmussen et al., *Curr. Opin. Biotechnol.* 20:74-82 (2009). Transforming growth factor beta-1 (TGF-β1) is a critical regulator of fibrosis in a variety of organ systems, acting via direct mechanisms to increase collagen production by fibroblasts and decrease turnover of matrix products. Willis et al., *Am. J. Pathol.* 166:1321-1332 (2005); Sakai et al., *Am. J. Pathol.* 184:2611-2617 (2014); Qi et al., *Am. J. Physiol. Renal Physiol.* 288:F800-F809 (2005); Bonniaud et al., *J. Immunol.* 173:2099-2108 (2004); Fujimoto et al., *Biochem. Biophys. Res. Commun.* 305:1002-1007 (2003); Stramer et al., *J. Cell Physiol.* 203:226-232 (2005); Kawakami et al., *J. Invest. Dermatol.* 110:47-51 (1998); Li et al., *Circulation* 96:874-881 (1997); Martinez et al., *Hepatology* 21:113-119 (1995); Peltonen et al., *J. Invest. Dermatol.* 97:240-248 (1991); Van Laethem et al., *Gastroenterology* 110:576-582 (1996). In addition, TGF-β1 is a key regulator of inflammatory responses and is thought to regulate fibrosis indirectly by modulating chronic inflammation. Pesce et al., *PLoS Pathog.* 5:e1000371 (2009). We have recently shown that the expression of TGF-β1 is markedly increased in lymphedematous tissues, both clinically and in mouse models of lymphedema. Inhibition of TGF-β1 using immunotherapy significantly accelerates lymphatic regeneration, decreases fibrosis, decreases inflammation, and improves lymphatic function in the mouse tail model. Avraham et al., *Plast. Reconstr. Surg.* 124:438-450 (2009); Clavin et al., *Am. J. Physiol. Heart Circ. Physiol.* 295: H2113-H2127 (2008); Avraham et al., *Am. J. Pathol.* 177: 3202-3214 (2010).

Inhibition of fibrotic responses preserves the capacity of the lymphatic system to transport interstitial fluid and inflammatory cells. Recent studies from our lab have shown that $CD4^+$ cells play a crucial role in the regulation of fibrosis in both clinical and animal models of lymphedema. Avraham et al., *Am. J. Pathol.* 177:3202-3214 (2010); Avraham et al., *FASEB J.* 27:1114-1126 (2013); Zampell et al., *Am. J. Physiol. Cell Physiol.* 302:C392-C404 (2012); Zampell et al., *PLoS ONE* 7:e49940 (2012). For example, we have found that clinical lymphedema biopsy specimens and animal models of lymphedema are infiltrated by $CD4^+$ cells, and that the number of these cells correlates with the degree of fibrosis and clinical severity of disease. Avraham et al., *FASEB J.* 27:1114-1126 (2013). Patients with late stage lymphedema had significantly more infiltrating T cells in general, specifically more $CD4^+$ cells, than those with early stage disease. Improvements in clinical symptoms of lymphedema after lymphovenous bypass, a procedure in which obstructed lymphatics are shunted to the venous circulation, is associated with decreased tissue fibrosis and decreased $CD4^+$ cell infiltration. Torrisi, et al., *Lymphat. Res. Biol.* 13:46-53 (2015).

The $CD4^+$ cell response in lymphedema, similar to other fibroproliferative disorders, is characterized by a mixed Th1/Th2 cell population. Avraham et al., *FASEB J.* 27:1114-1126 (2013). Naïve $CD4^+$ T cells, also known as T-helper or Th cells, patrol secondary lymphoid structures and, upon activation, differentiate along numerous distinct/overlapping cell types (e.g., Th1, Th2, Th17, T regulatory, etc.). The Th2 subset of cells plays a key role in regulation of responses to parasites and some autoimmune responses. These cells have also been implicated in the pathology of fibroproliferative diseases in a number of organ systems including the heart, lung, kidneys and skin. More recent studies have shown that the number of Th2 is increased in tissue biopsies obtained from patients with lymphedema and that inhibition of Th2 differentiation decreases the pathology of lymphedema in mouse models.

Depletion of $CD4^+$ cells (but not other inflammatory cell types including $CD8^+$ cells or macrophages) or inhibition of Th2 differentiation (but not generalized inflammation or inhibition of interleukin-6) markedly decreases the degree of fibrosis, increases lymphangiogenesis and lymphatic fluid transport, and effectively treats established lymphedema in preclinical mouse models. Avraham et al., *FASEB J.* 27:1114-1126 (2013); Zampell et al., *PLoS ONE* 7:e49940 (2012); Ghanta et al., *Am. J. Physiol. Heart Circ. Physiol.* 308:H1065-1077 (2015). These findings are supported by recent studies demonstrating that T cells potently inhibit lymphangiogenesis by producing anti-lymphangiogenic cytokines/growth factors, including interferon gamma (IFN-γ), interleukin (IL)-4, IL-13, and TGF-β1. Kataru et al., *Immunity* 34:96-107 (2011); Shin et al., *Nat. Commun.* 6:6196 (2015); Shao et al., *J. Interferon. Cytokine Res.* 26:568-574 (2006); Oka et al., *Blood* 111:4571-4579 (2008). Taken together, these findings suggest that infiltrating $CD4^+$ cells in lymphedematous tissues decrease lymphatic function through multiple mechanisms including induction of structural changes of lymphatic vessels secondary to tissue fibrosis and inhibition of collateral lymphatic vessel formation.

Previous experimental treatments for lymphedema have focused on delivery of lymphangiogenic cytokines. Skobe et al., *Nat. Med.* 7:192-198 (2001). For example, some previous studies have focused on repairing damaged lymphatics using lymphangiogenic cytokines such as vascular endothelial growth factor-c (VEGF-C). Tammela et al., *Nat. Med.* 13:1458-1466 (2007); Baker et al., *Breast Cancer Res.* 12:R70 (2010). Although promising, application of this approach, particularly to cancer patients, may be untenable as these same mechanisms regulate tumor growth and metastasis, raising the risk of cancer metastases or recurrence. Zhang et al., *Cancer Res.* 70:2495-2503 (2010); Yu et al., *J. Exp. Clin. Cancer Res.* 28:98 (2009); Sugiura et al., *Int. J. Oncol.* 34:673-680 (2009); Gu et al., *Clin. Exp. Metastasis* 25:717-725 (2008); Kazama et al., *Hepatogastroenterology* 54:71-76 (2007); Hirakawa et al., *Blood* 109: 1010-1017 (2007). In contrast, depletion of CD4+ T cells locally can treat the underlying pathology rather than only promoting lymphangiogenesis, and can therefore be much safer for use in cancer patients. This approach can thus enable treatment of cancer survivors during flare-ups/exacerbations of lymphedema, add to conservative therapy in non-surgical patients, prevent disease development in high risk patients, or improve outcomes of surgical treatments for lymphedema.

Tacrolimus is an anti-T cell agent that is FDA approved as a topical formulation and used to treat cutaneous inflammatory/fibrotic diseases including atopic dermatitis (Ruzicka et al., *N. Engl. J. Med.* 337:816-821 (1997)), psoriasis (Wang et al., *J. Cutan. Med. Surg.* 18:8-14 (2014)), and localized scleroderma (Mancuso et al., *Br. J. Dermatol.* 152:180-182 (2005)). Tacrolimus is a macrolide produced by the soil bacterium *Streptomyces tsukubaensis* that is well-tolerated when used for prevention of transplant rejection and treatment of a variety of autoimmune diseases. It exerts its anti-T cell properties by binding to FK-506 binding protein 12 (FKBP-12) thus inhibiting calcineurin, and ultimately decreasing IL-2 expression. Clipstone et al., *Nature* 357: 695-697 (1992). Because IL-2 is essential for T cell activation and differentiation of $CD4^+$ T cells, calcineurin inhibitors have profound $CD4^+$ cell immunosuppressive effects. Liao et al., *Immunity* 38:13-25 (2013); Rautajoki et al., *Ann. Med.* 40:322-335 (2008).

Teriflunomide is an immunosuppressive agent that decreases T cell inflammatory responses. Oral administration of teriflunomide is FDA-approved for the treatment of multiple sclerosis. Williamson et al., *J. Biol. Chem.* 270: 22467-22472 (1995); Davis et al., *Biochem.* 35:1270-1273 (1996); Iglesias-Bregna et al., *J. Pharmacol. Exp. Ther.* 347:203-211 (2013). Teriflunomide is the active metabolite of leflunomide, and inhibits de novo pyrimidine synthesis by blocking the enzyme dihydroorotate dehydrogenase. Teriflunomide has also been shown to inhibit activation of Signal transducer and activator of transcription-6 (STA T-6) a key regulator of Th2 differentiation. Olsan et al., *Proc. Nat. Acad Sci. USA* 108:18067-18072 (2011). As a result of these mechanisms, teriflunomide inhibits actively dividing Th2 cells and decreases inflammatory responses.

Pirfenidone is a compound that has anti-fibrotic and anti-inflammatory effects. Recent studies have suggested that this activity is due, at least in part, to inhibition of production and activity of TGF-β. Iyer et al., *J. Pharmacol. Exp. Ther.* 291:367-373 (1999); Tada et al., *Clin. Exper. Pharmacol. Physiol.* 28:522-527 (2001); Oku et al., *Eur. J. Pharmacol.* 590:400-408 (2008); Tian et al., *Chin. Med Sci. J.* 21:145-151 (2006); Schaefer et al., *Eur. Respir. Rev.* 20:85-97 (2011). It is currently approved in the United States by the FDA for oral administration in the treatment of idiopathic pulmonary fibrosis (IPF) after its safety and efficacy were established in three clinical trials of 1,247 patients with IPF. Taniguchi et al., *Eur. Respir. J.* 35:821-829 (2010); Noble et al., *Lancet* 377:1760-1769 (2011); King et al., *N. Engl. J. Med* 370:2083-2092 (2014). In addition to the treatment of IPF, pirfenidone has been clinically evaluated for its safety and efficacy for the treatment of other chronic fibrotic disorders, including renal fibrosis, hepatic fibrosis, and myelofibrosis. Tada et al., *Clin. Exper. Pharmacol.*

Physiol. 28:522-527 (2001); Cho et al., *Clin. J. Am. Soc. Nephrol.* 2:906-913 (2007); Nagai et al., *Intern. Med* 41:1118-1123 (2002); Raghu et al., *Am. J. Respir. Crit. Care Med* 159:1061-1069 (1999); Gahl et al., *Mol. Genet. Metab.* 76:234-242 (2002); Armendariz-Borunda et al., *Gut* 55:1663-1665 (2006); Angulo et al., *Dig. Dis. Sci.* 47:157-161 (2002); Mesa et al., *Brit. J. Haematol.* 114:111-113 (2001).

Captopril is an angiotensin-converting enzyme (ACE) inhibitor, approved by the FDA for oral administration in the treatment of hypertension and certain types of heart failure and diabetic nephropathy. ACE converts angiotensin I (AngI) to angiotensin II (AngII) and causes blood vessel constriction, inhibits vasodilatation, and indirectly regulates intravascular fluid volumes by effects on the renin-angiotensin-system (RAS). Therefore, inhibition of ACE has been a mainstay therapy for hypertension. More recent studies have shown that AngII is also a key regulator of fibrosis in a variety of organ systems, including the kidney, liver, and lung. Langham et al., *Diabetes Care* 29:2670-2675 (2006); Alves de Albuquerque et al., *Kidney Intl.* 65:846-859 (2004); Osterreicher et al., *Hepatology.* 50:929-938 (2009); Mak et al., *Mol. Ther.* 23:1434-1443 (2015); Wang et al., *Cell Physiol. Biochem.* 36:697-711 (2015). The pro-fibrotic effects of AngII are mediated by a number of mechanisms, including production of reactive oxygen species, production of chemokines and cytokines, increased expression of adhesion molecules, and regulation of TGF-β expression/activity. In contrast, AngI has anti-proliferative and anti-fibrotic activities by activating its cell surface receptor, Mas. Clarke et al., *Int. J. Hypertens.* 2012:307315 (2011). As a result, inhibitors of ACE and/or AngII, such as captopril, losartan, and other similar medications, have been proposed as a potential therapeutic option for fibrotic disorders of the lung, kidney, and liver.

There are currently no pharmacologic therapies available for the treatment of lymphedema. Previous studies on lymphedema have focused on treatment with systemic medications. For example, coumarin taken by mouth has been used in patients with lymphedema with modest success. Casley-Smith et al., *BMJ* 307:1037-1041 (1993); Casley-Smith et al., *N. Engl. J. Med.* 329:1158-1163 (1993); Casley-Smith et al., *Australas J. Dermatol.* 33:69-74 (1992); Loprinzi et al., *N. Engl. J. Med.* 340:346-350 (1999). However, widespread clinical application of this drug has been hampered by significant toxicity including liver failure and death. Loprinzi et al., *N. Engl. J. Med.* 340:346-350 (1999). Strategies targeting fibrosis-in particular, inhibition of generalized $CD4^+$ inflammatory responses, Th2 differentiation, and/or the TGF-β pathway-hold clinical promise for treating lymphedema. Although highly effective, systemic depletion of CD4+ cells is not clinically viable due to unacceptable morbidity and systemic complications such as infections, cancer recurrence, and autoimmune disorders. In contrast, local delivery of agents to treat pathologic events related to lymphedema is a novel approach that may limit systemic toxicity. Because lymphedema is primarily a disease of the skin and subcutaneous soft tissues of the extremities, it is possible to use topical approaches, which might be better-tolerated and provide a more targeted approach, thereby avoiding systemic complications. Accordingly, there is a need in the art for novel treatments for lymphedema, especially topical treatments.

SUMMARY OF THE INVENTION

Some of the main aspects of the present invention are summarized below. Additional aspects are described in the Detailed Description of the Invention, Examples, Drawings, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the present invention.

In one aspect, the invention provides a pharmaceutical composition comprising a combination of anti-T cell, anti-TGF-β1, and/or anti-angiotensin agents. For example, the invention provides a pharmaceutical composition comprising: (i) an effective amount of one or more anti-T cell agents and (ii) an effective amount of one or more anti-TGF-β1 agents and/or an effective amount of one or more anti-angiotensin agents. In a particular embodiment, the invention provides a pharmaceutical composition comprising (i) an effective amount of one or more anti-T cell agents and (ii) an effective amount of one or more anti-TGF-β1 agents. In another embodiment, the invention provides a pharmaceutical composition comprising: (i) an effective amount of one or more anti-T cell agents and (ii) an effective amount of one or more anti-angiotensin agents. In still a further embodiment, the invention provides a pharmaceutical composition comprising: (i) an effective amount of one or more anti-T cell agents and (ii) an effective amount of one or more anti-TGF-β1 agents and (iii) an effective amount of one or more anti-angiotensin agents.

In one embodiment, the anti-T cell agent is selected from the group consisting of tacrolimus, teriflunomide, leflunomide, cyclosporine, pimecrolimus, denileukin diftitox, and Basiliximab. In one embodiment, the anti-TGF-β1 agent or anti-angiotensin agent is selected from the group consisting of pirfenidone, captopril, zofenopril, enalapril, lisinopril, ramipril, quinapril, perindopril, benazepril, imidapril, trandolapril, cilazapril, fosinopril, losartan, irbesartan, olmesartan, candesartan, telmisartan, valsartan, and fimasartan. In a particular embodiment, the anti-angiotensin agent is an ACE inhibitor, for example, an ACE-2 agonist. The composition can be formulated for systemic administration or for local administration. In a preferred embodiment, the composition is formulated for topical administration.

The pharmaceutical composition of the invention can comprise any combination of anti-T cell, anti-TGF-β1, and/or anti-angiotensin agents. For instance, in one embodiment, the composition comprises tacrolimus and pirfenidone. In another embodiment, the composition comprises tacrolimus, pirfenidone, and teriflunomide. In an additional embodiment, the composition comprises tacrolimus, pirfenidone, and leflunomide. In further aspects, the composition comprises tacrolimus and captopril; or teriflunomide and captopril; or leflunomide and captopril; or pirfenidone and captopril; or tacrolimus, captopril, and teriflunomide; or tacrolimus, captopril, and leflunomide; or tacrolimus, captopril, and pirfenidone.

In an embodiment in which the pharmaceutical composition is formulated for topical administration, the composition can comprise about 0.01% to about 1% tacrolimus, preferably about 0.05 to about 0.2% tacrolimus; about 0.1 mg/ml to about 5 mg/ml pirfenidone, preferably about 0.5 mg/ml to about 2 mg/ml pirfenidone; about 10 mg/ml to about 50 mg/ml teriflunomide, preferably about 20 mg/ml to about 30 mg/ml teriflunomide; about 1% to about 20% leflunomide, preferably about 5% to about 15% leflunomide; and/or about 1% to about 20% captopril. The pharmaceutical composition is preferably in a form selected from an ointment, a cream, a lotion, a paste, a gel, a mousse, a foam, a lacquer, a suspension, a liquid, and a spray. In a preferred embodiment, the composition is in the form of an ointment.

The pharmaceutical composition of the invention can be for use in treating or preventing edema.

The invention also provides a method of treating or preventing edema, the method comprising administering to a subject in need thereof a pharmaceutical composition comprising an effective amount of one or more drugs selected from the group consisting of tacrolimus, teriflunomide, leflunomide, cyclosporine, pimecrolimus, denileukin diftitox, Basiliximab, pirfenidone, captopril, zofenopril, enalapril, lisinopril, ramipril, quinapril, perindopril, benazepril, imidapril, trandolapril, cilazapril, fosinopril, losartan, irbesartan, olmesartan, candesartan, telmisartan, valsartan, and fimasartan.

In one aspect, the edema is lymphedema.

In one aspect, the method of the invention can comprise administering a combination of anti-T cell, anti-TGF-β1, and/or anti-angiotensin agents. In a particular embodiment, the method comprises administering a pharmaceutical composition comprising: (i) an effective amount of one or more anti-T cell agents selected from the group consisting of tacrolimus, teriflunomide, leflunomide, cyclosporine, pimecrolimus, denileukin diftitox, and Basiliximab; and (ii) an effective amount of one or more anti-TGF-β1 agents and/or anti-angiotensin agents selected from the group consisting of pirfenidone, captopril, zofenopril, enalapril, lisinopril, ramipril, quinapril, perindopril, benazepril, imidapril, trandolapril, cilazapril, fosinopril, losartan, irbesartan, olmesartan, candesartan, telmisartan, valsartan, and fimasartan. The method can comprise administering any combination of anti-T cell, anti-TGF-β1, and/or anti-angiotensin agents. For instance, in one embodiment, the method comprises administering a pharmaceutical composition comprising tacrolimus and pirfenidone. In another embodiment, the method comprises administering a pharmaceutical composition comprising tacrolimus, pirfenidone, and teriflunomide. In an additional embodiment, the method comprises administering a pharmaceutical composition comprising tacrolimus, pirfenidone, and leflunomide. In further aspects, the method comprises administering a pharmaceutical composition comprising tacrolimus and captopril; or teriflunomide and captopril; or leflunomide and captopril; or pirfenidone and captopril; or tacrolimus, captopril, and teriflunomide; or tacrolimus, captopril, and leflunomide; or tacrolimus, captopril, and pirfenidone.

In the methods of the invention, the pharmaceutical composition can be administered systemically or locally. In a preferred method, the pharmaceutical composition is administered topically. In this aspect of the invention, the pharmaceutical composition about 0.01% to about 1% tacrolimus, preferably about 0.05 to about 0.2% tacrolimus; about 0.1 mg/ml to about 5 mg/ml pirfenidone, preferably about 0.5 mg/ml to about 2 mg/ml pirfenidone; about 10 mg/ml to about 50 mg/ml teriflunomide, preferably about 20 mg/ml to about 30 mg/ml teriflunomide; about 1% to about 20% leflunomide, preferably about 5% to about 15% leflunomide; and/or about 1% to about 20% captopril. In a method of topical administration, the pharmaceutical composition can be in a form selected from an ointment, a cream, a lotion, a paste, a gel, a mousse, a foam, a lacquer, a suspension, a liquid, and a spray. Preferably, the pharmaceutical composition is in the form of an ointment.

It is within the skill of the ordinary artisan to determine a dosing schedule and duration for systemic or local administration. In one embodiment, the pharmaceutical composition is administered topically at least once a day. In another embodiment, the pharmaceutical composition is administered topically at least twice a day. Where the pharmaceutical composition or method involves prevention of edema, particularly prevention of lymphedema, the composition can be administered within about six weeks of a lymphatic injury, preferably within about two weeks of a lymphatic injury.

BRIEF DESCRIPTION OF THE FIGURES

FIG. 31 shows that captopril treatment increases trafficking of dendritic cells after lymphatic injury. (A) shows representative flow cytometry from inguinal lymph nodes demonstrating FITC+ CD11c cells in control and captopril treated mice after PLND. (B) shows the percentage (left) and absolute number (right) of FITC+ CD11c cells in inguinal lymph nodes of control and captopril treated mice after PLND.

FIG. 32 show that captopril treatment increases hind limb collecting lymphatic pumping. (A) shows a representative plot of collecting lymphatic pumping as assessed by ICG lymphangiography in control and captopril treated mice after PLND. (B) shows quantification of packet frequency (pumping) of hind limb collecting lymphatics.

FIG. 33 shows that captopril treatment decreases T cell infiltration after PLND. Representative high power photomicrographs of control (A) and captopril treated (B) mouse hind limb sections stained for CD3+(T cell marker) and LYVE-1 (lymphatic marker) are shown. Nuclear counterstain is shown with DAPI. (C) shows quantification of CD3+ cells in hind limb tissues of control and captopril treated mice.

FIG. 34 shows that captopril treatment decreases macrophage infiltration after PLND. Representative high power photomicrographs of control (A) and captopril treated (B) mouse hind limb sections stained for F4/80+(macrophage marker) and LYVE-1 (lymphatic marker) are shown. Nuclear counterstain is shown with DAPI. (C) shows quantification of f4/80+ cells in hind limb tissues of control and captopril treated mice.

FIG. 35 shows that captopril treatment increases lymphangiogenesis after PLND. Representative high power photomicrographs of control (A) and captopril treated (B) mouse hind limb sections stained for LYVE-1 (lymphatic marker) are shown. Nuclear counterstain is shown with DAPI. (C) shows quantification of LYVE-1+ vessels in control and captopril treated mice (*p<0.05).

FIG. 40 show that captopril treatment decreases hind limb type I collagen deposition after lymphatic ablation with DT. Representative high power photomicrographs of control (A) and captopril treated (B) mouse hind limb sections stained for type I collagen (fibrosis marker) and LYVE-1 (lymphatic marker) are shows. Nuclear counterstain is shown with DAPI. (C) shows Quantification of type I collagen in hind limb tissues of control and captopril treated mice. Note significant difference (*p<0.0001) between ipsilateral control and ipsilateral captopril limbs.

FIG. 46 shows that captopril treatment decreases fibroadipose tissue deposition in the mouse tail model of lymphedema 6 weeks after lymphatic ablation. (A) shows representative H&E stained mouse tail cross sections 6 weeks after lymphatic ablation and treated with control (left) or captopril topically. Brackets represent fibroadipose tissue deposition. (B) shows Quantification of subcutaneous fibroadipose deposition in mice treated with control or captopril topically 6 weeks after tail lymphatic ablation. Note significant decrease in captopril treated mice (*p<0.0001).

FIG. 49 shows that captopril treatment decreases lymphatic vessel area and correlates with decreased lymphatic stasis in the mouse tail model of lymphedema 6 weeks after lymphatic ablation. Representative cross sections of the mouse tails in control (A) and captopril (B) treated animals stained for LYVE-1 (a lymphatic marker) are shown. Note decreased diameter of lymphatic vessels in captopril treated mice. (C) shows quantification of LYVE-1+ vessel area in control and captopril mice. Note significant decrease in lymphatic vessel area corresponding to decreased lymphatic stasis.

DETAILED DESCRIPTION OF THE INVENTION

Figure 1:
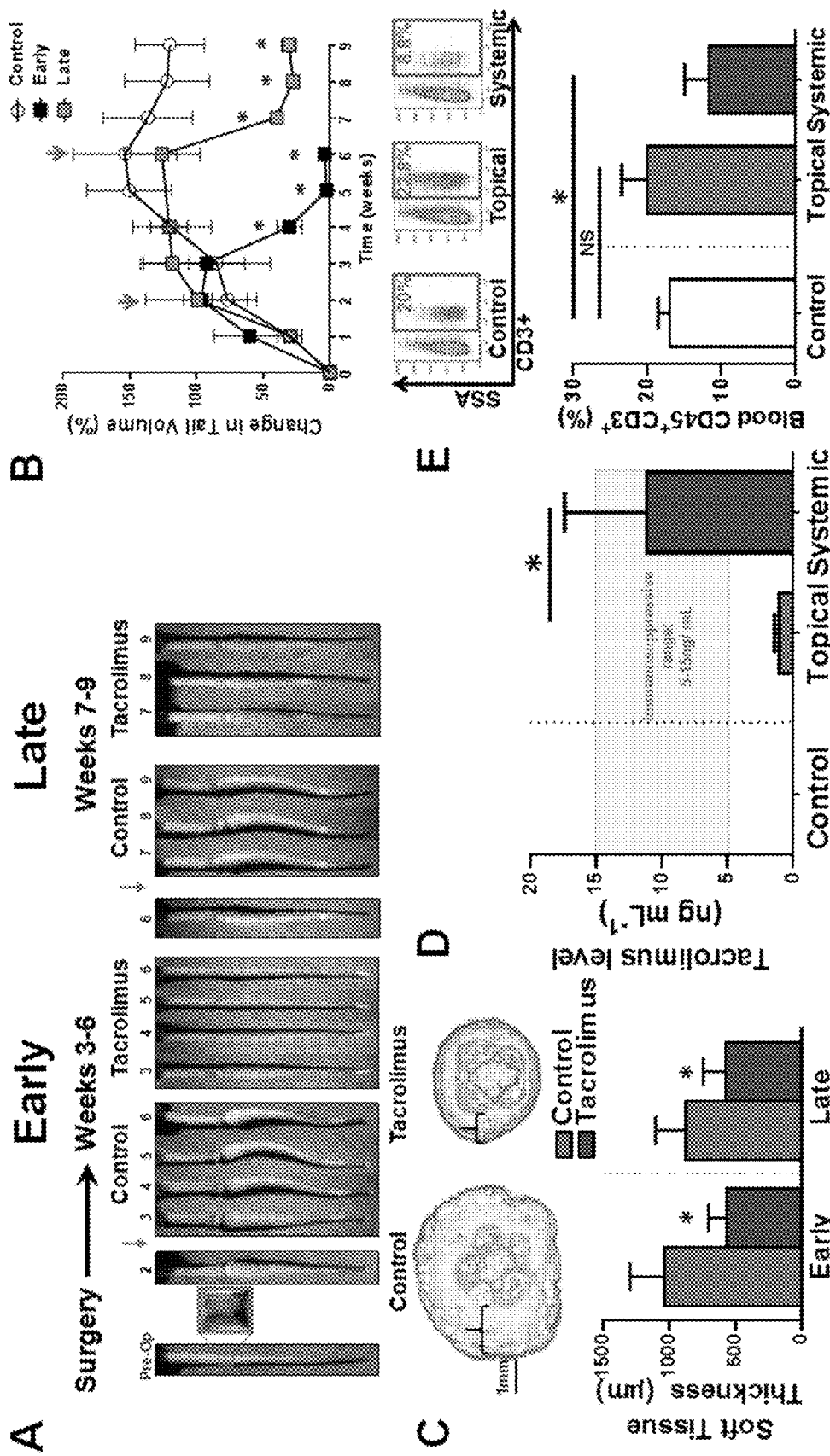
FIG. 1 shows that topical tacrolimus decreases tail lymphedema. (A) shows representative photographs of mouse tails after surgical excision of superficial/deep collecting lymphatics and treatment with or without topical tacrolimus beginning either 2 weeks (early treatment) or 6 weeks (late treatment) after surgery. Arrows indicate initiation of therapy. (B) is a graphical representation of tail volume changes after early (*p=0.021) or late (*p=0.018) treatment with tacrolimus as compared with controls. (C) (upper panel) shows representative cross-sectional histological images of control and early tacrolimus-treated mouse tails harvested 6 weeks after lymphatic ablation. Brackets show soft tissue thickness. (C) (lower panel) shows quantification of soft tissue changes after early or late treatment with tacrolimus (*p=<0.001). (D) shows quantification of whole blood tacrolimus levels demonstrating immunosuppressive concentrations in systemically-treated animals (4 mg kg IP daily) and non-immunosuppressive levels in the topically-treated group (*p=0.007). (E) shows flow cytometry plots (upper panel) and quantification of blood T cells (lower panel) in animals treated with vehicle control, topical tacrolimus, or systemic tacrolimus. Flow plots represent Side Scatter Area (SSA) on the y-axis and $CD3^+$ representing T cells on the x-axis. Note significant reduction in T cells only in systemically-treated animals (*p=0.012).

The present invention relates, in part, to the use of anti-T cell agents and/or anti-TGF-β1 agents and/or anti-angiotensin agents as novel, safe, and effective treatments for edema, especially lymphedema. The present invention is based, in part, on the surprising discovery that systemic or local administration of anti-T cell, anti-TGF-β1, and/or anti-angiotensin agents, for example, tacrolimus, pirfenidone, teriflunomide, leflunomide, and/or captopril, dramatically improves lymphedema and lymphatic function, and has a variety of other beneficial biological effects, including stimulating lymphangiogenesis, when administered to mammalian subjects. Moreover, because these agents act at different steps of the fibrosis pathway, combinations of anti-T cell, anti-TGF-β1, and/or anti-angiotensin agents can be more effective than administration of a single agent, potentially exhibiting synergistic effects.

Accordingly, the present invention provides compositions and methods for treating or preventing edema, such as lymphedema, and/or for producing a variety of other beneficial biological effects including, but not limited to: reduced tissue swelling, reduced lymphatic fluid stasis or "pooling," reduced tissue fibrosis, reduced tissue inflammation, reduced infiltration of leukocytes, reduced infiltration of macrophages, reduced infiltration of naïve and differentiated T-cells, reduced TGF-β1 expression and reduced expression and/or activation of downstream mediators (e.g., pSmad3), reduced levels of angiotensins and/or ACE, reduced collagen deposition and/or scar formation, improved or increased lymphatic function, improved or increased lymph fluid transport, improved or increased lymphangiogenesis, and/or improved or increased lymph pulsation frequency.

Unless defined otherwise, all technical and scientific terms used herein have the same meaning as commonly understood by one of ordinary skill in the art to which this invention is related. For example, *The Dictionary of Cell and Molecular Biology* (5th ed. J. M. Lackie ed., 2013), the *Oxford Dictionary of Biochemistry and Molecular Biology* (2d ed. R. Cammack et al. eds., 2008), and *The Concise Dictionary of Biomedicine and Molecular Biology* (2d ed. P-S. Juo, 2002) can provide one of skill with general definitions of some terms used herein.

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Système International de Unites (SI) accepted form. Numeric ranges are inclusive of the numbers defining the range. Where a numeric term is preceded by "about," the term includes the stated number and values ±10% of the stated number. The headings provided herein are not limitations of the various aspects or embodiments of the invention, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are included.

The term "edema," as used herein, includes lymphedema, lymphatic dysfunction, lymphatic tissue fibrosis, idiopathic edema, peripheral edema, and eye edema. As used herein, "edema" does not include pulmonary edema or cerebral edema. Edema can include acute edema, chronic edema, post-operative edema, and gradual-onset edema. Symptoms of edema can include swelling, fullness, or puffiness of tissues, inflammation, fibrosis, heaviness, pain, decreased range of motion, aching, recurring infections, skin thickening, or discomfort.

An "active agent" is an agent which itself has biological activity, or which is a precursor or prodrug that is converted in the body to an agent having biological activity. Active agents for treating or preventing edema can include immunosuppressive agents, anti-fibrotic agents, anti-T cell agents, anti-TGF-β1 agents, and anti-angiotensin agents. In some embodiments, the agents are small molecule compounds. In other embodiments, the agents are macromolecules, such as polynucleotides (e.g., inhibitory RNA) or polypeptides (e.g., antibodies).

An "anti-T cell agent" is a molecule that reduces T cell-mediated inflammation, T cell activation, T cell differentiation, and/or T cell proliferation. Classes of anti-T cell agents include calcineurin inhibitors and IL-2 inhibitors. Examples of small molecule anti-T cell agents include tacrolimus, teriflunomide, leflunomide, cyclosporine, and pimecrolimus. Examples of macromolecule anti-T cells agents include denileukin diftitox and Basiliximab.

An "anti-TGF-β1 agent" is a molecule that inhibits the expression, secretion, activation, signaling, or activity of transforming growth factor beta 1. Pirfenidone is one example of a small molecule anti-TGF-β1 agent.

An "anti-angiotensin agent" is a molecule that inhibits the activity of AngI or AngII, or a molecule that inhibits AngI to AngII conversion (e.g., ACE inhibitors). Examples of anti-angiotensin agents include captopril, zofenopril, enalapril, lisinopril, ramipril, quinapril, perindopril, benazepril, imidapril, trandolapril, cilazapril, fosinopril, losartan, irbesartan, olmesartan, candesartan, telmisartan, valsartan, fimasartan, diminazene aceturate, xanthenone, and AVE 099.

The terms "inhibit," "block," and "suppress" are used interchangeably and refer to any statistically significant decrease in biological activity, including full blocking of the activity.

In one aspect, the method of the invention can comprise administering a combination of anti-T cell, anti-TGF-β1, and/or anti-angiotensin agents. In a particular embodiment, the method comprises administering a pharmaceutical composition of the invention comprising: (i) an effective amount of one or more anti-T cell agents selected from the group consisting of tacrolimus, teriflunomide, leflunomide, cyclosporine, pimecrolimus, denileukin diftitox, and Basiliximab; and (ii) an effective amount of one or more anti-TGF-1 agents and/or one or more anti-angiotensin agents selected from the group consisting of pirfenidone, captopril, zofenopril, enalapril, lisinopril, ramipril, quinapril, perindopril, benazepril, imidapril, trandolapril, cilazapril, and fosinopril, losartan, irbesartan, olmesartan, candesartan, telmisartan, valsartan, and fimasartan. The method of the invention can comprise administering a pharmaceutical compound of the invention comprising any combination of anti-T cell, anti-TGF-β1, and/or anti-angiotensin agents. For instance, in one embodiment, the method comprises administering a pharmaceutical composition comprising tacrolimus and pirfenidone. In another embodiment, the method comprises administering a pharmaceutical composition comprising tacrolimus, pirfenidone, and teriflunomide. In an additional embodiment, the method comprises administering a pharmaceutical composition comprising tacrolimus, pirfenidone, and leflunomide. In further aspects, the method comprises administering a pharmaceutical composition comprising tacrolimus and captopril; or teriflunomide and captopril; or leflunomide and captopril; or pirfenidone and captopril; or tacrolimus, captopril, and teriflunomide; or tacrolimus, captopril, and leflunomide; or tacrolimus, captopril, and pirfenidone.

By "subject" or "individual" or "patient" is meant any subject, preferably a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, and so on.

In some embodiments the subject may have or may have had cancer, for example, a cancer comprising a solid tumor. In some embodiments the subject may have or may have had breast cancer or a cancer affecting female reproductive organs, cutaneous system, musculoskeletal system, soft tissues of the extremities or trunk, male reproductive system, urinary system, or the head and neck. In some embodiments, the subject may have undergone axillary lymph node dissection. In some embodiments, the subject has received treatment for cancer, and the edema, lymphedema, or lymphatic injury is associated with the cancer treatment or diagnosis. For example, the subject may be receiving or may have received chemotherapy or radiation therapy for cancer treatment or other indications, or may have had one or more lymph nodes surgically removed in the course of cancer treatment or diagnosis.

In some embodiments the subject may have sustained a lymphatic injury (for example as the result of removal, ligation or obstruction of lymph nodes or lymph vessels, or fibrosis of lymph tissue), or the subject may be obese or have or had an infection that leads to edema, such as lymphedema. In some embodiments the infection may be a skin infection or a history of skin infection(s) that are related to lymphedema or lymphatic injury. In some embodiments the infection may be a parasitic infection that obstructs lymphatic flow or injures the lymphatic system. In some embodiments the subject may have sustained lymphatic injury from joint replacement, trauma, burns, radiation, or chemotherapy.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already with the disorder. In certain embodiments, a subject is successfully "treated" for a disease or disorder according to the methods provided herein if the patient shows, e.g., total, partial, or transient alleviation or elimination of symptoms associated with the disease or disorder. For example, "treating edema" can include, but is not limited to, decreasing swelling, decreasing inflammation, decreasing fibrosis, decreasing pain, increasing range of motion, decreasing heaviness, decreasing tightness, decreasing skin thickening, and/or improving lymphatic function.

"Prevent" or "prevention" refers to prophylactic or preventative measures that prevent and/or slow the development of a targeted pathologic condition or disorder. Thus, those in need of prevention include those at risk of or susceptible to developing the disorder. Subjects that are at risk of or susceptible to developing lymphedema include, but are not limited to, cancer patients undergoing radiation therapy, chemotherapy, and/or surgical lymph node dissection. In certain embodiments, a disease or disorder is successfully prevented according to the methods provided herein if the patient develops, transiently or permanently, e.g., fewer or less severe symptoms associated with the disease or disorder, or a later onset of symptoms associated with the disease or disorder, than a patient who has not been subject to the methods of the invention.

In a prophylactic context, the pharmaceutical composition of the invention can be administered at any time before or after an event, for example, radiation therapy, chemotherapy, or surgical lymph node dissection, which places a subject at risk of or susceptible to lymphatic injury and/or developing edema. In some aspects, the pharmaceutical composition is administered prophylactically up to about one week before the event, such as 1, 2, 3, 4, 5, 6, or 7 days before the event. In some instances, the pharmaceutical composition is administered prophylactically on the same day as the event. In some embodiments, the pharmaceutical composition is administered prophylactically within six weeks of the event, for example, within about 1, 2, 3, 4, 5, or 6 days, or within about 1, 2, 3, 4, 5 or 6 weeks of the event. In one embodiment, the pharmaceutical composition is administered prophylactically for about 2-4 weeks or for about 1, 2, 3, 4, 5, or 6 weeks.

In some embodiments the treatment and/or prevention methods described herein may be performed in combination with one or more additional edema or lymphedema treatment and/or prevention methods known in the art, for example, treatment methods involving the administration of other therapeutic agents and/or treatment methods involving surgery, massage, compression therapy, fluid drainage therapy, acupuncture, laser, or any other suitable treatment methods.

The term "pharmaceutical composition" refers to a preparation that is in such form as to permit the biological activity of the active ingredient to be effective, and which contains no additional components that are unacceptably toxic to a subject to which the composition would be administered. Pharmaceutical compositions can be in numerous dosage forms, for example, tablet, capsule, liquid, solution, softgel, suspension, emulsion, syrup, elixir, tincture, film, powder, hydrogel, ointment, paste, cream, lotion, gel, mousse, foam, lacquer, spray, aerosol, inhaler, nebulizer, ophthalmic drops, patch, suppository, and/or enema. Pharmaceutical compositions typically comprise a pharmaceutically acceptable carrier, and can comprise one or more of a buffer (e.g. acetate, phosphate or citrate buffer), a surfactant (e.g. polysorbate), a stabilizing agent (e.g. human albumin), a preservative (e.g. benzyl alcohol), a penetration enhancer, an absorption promoter to enhance bioavailability and/or other conventional solubilizing or dispersing agents. Choice of dosage form and excipients depends upon the active agent to be delivered and the disease or disorder to be treated or prevented, and is routine to one of ordinary skill in the art.

"Systemic administration" means that a pharmaceutical composition is administered such that the active agent enters the circulatory system, for example, via enteral, parenteral, inhalational, or transdermal routes. Enteral routes of administration involve the gastrointestinal tract and include, without limitation, oral, sublingual, buccal, and rectal delivery. Parenteral routes of administration involve routes other than the gastrointestinal tract and include, without limitation, intravenous, intramuscular, intraperitoneal, intrathecal, and subcutaneous. "Local administration" means that a pharmaceutical composition is administered directly to where its action is desired (e.g., at or near the site of the injury or symptoms). Local routes of administration include, without limitation, topical, inhalational, subcutaneous, ophthalmic, and otic. It is within the purview of one of ordinary skill in the art to formulate pharmaceutical compositions that are suitable for their intended route of administration.

An "effective amount" of a composition as disclosed herein is an amount sufficient to carry out a specifically stated purpose. An "effective amount" can be determined empirically and in a routine manner, in relation to the stated purpose, route of administration, and dosage form.

In some embodiments, administration of the anti-T cell agent and/or the anti-TGF-β1 agent and/or the anti-angiotensin agent can comprise systemic administration, at any suitable dose and/or according to any suitable dosing regimen, as determined by one of skill in the art. For example, in some embodiments, tacrolimus or an analogue, variant, or derivative thereof is administered systemically to the subject at a daily dose of about 0.01 mg/kg to about 5 mg/kg. More particularly, tacrolimus or an analogue, variant, or derivative thereof can be administered to the subject at a daily dose of about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3.0, 3.25, 3.5, 3.75, 4.0, 4.25, 4.5, 4.75, or 5.0 mg/kg.

In some embodiments, teriflunomide or an analogue, variant, or derivative thereof is administered systemically to the subject at a daily dose of about 0.1 mg/kg to about 5 mg/kg. More particularly, teriflunomide or an analogue, variant, or derivative thereof can be administered to the subject at a daily dose of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3.0, 3.25, 3.5, 3.75, 4.0, 4.25, 4.5, 4.75, or 5.0 mg/kg.

In some embodiments, leflunomide or an analogue, variant, or derivative thereof is administered systemically to the subject at a daily dose of about 0.1 mg/kg. to about 5 mg/kg. More particularly, leflunomide or an analogue, variant, or derivative thereof can be administered to the subject at a daily dose of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3.0, 3.25, 3.5, 3.75, 4.0, 4.25, 4.5, 4.75, or 5.0 mg/kg.

In some embodiments, pirfenidone or an analogue, variant, or derivative thereof is administered systemically to the subject at a daily dose of about 50 mg/kg to about 2500 mg/kg. More particularly, pirfenidone or an analogue, variant, or derivative thereof can be administered to the subject at a daily dose of about 50, 55, 60, 65, 70, 75, 80, 85, 90, 95, 100, 110, 120, 130, 140, 150, 160, 170, 180, 190, 200, 220, 240, 260, 280, 300, 325, 350, 375, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 mg/kg.

In some embodiments, captopril or an analogue, variant, or derivative thereof is administered systemically to the subject at a daily dose of about 0.1 mg/kg to about 10 mg/kg. More particularly, captopril or an analogue, variant, or derivative thereof can be administered to the subject at a daily dose of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3.0, 3.25, 3.5, 3.75, 4.0, 4.25, 4.5, 4.75, 5.0, 5.5, 6.0, 6.5, 7.0, 7.5, 8.0, 8.5, 9.0, 9.5, or 10 mg/kg.

In some embodiments, administration of the anti-T cell agent and/or the anti-TGF-β1 agent and/or the anti-angiotensin agent can comprise local administration, at any suitable dose and/or according to any suitable dosing regimen, as determined by one of skill in the art. For example, in some embodiments, tacrolimus or an analogue, variant, or derivative thereof is administered to the subject in the form of a topical composition comprising from about 0.01 mg/ml to about 5 mg/ml, or from about 0.1 mg/ml to 2 mg/ml, or about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3.0, 3.25, 3.5, 3.75, 4.0, 4.25, 4.5, 4.75, or 5.0 mg/ml tacrolimus or an analogue, variant, or derivative thereof. In some embodiments, tacrolimus or an analogue, variant, or derivative thereof is administered to the subject in the form of a topical composition comprising from about 0.01% to about 1%, or from about 0.03% to about 0.5%, or from about 0.05 to about 0.2%, or about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1.0% tacrolimus or an analogue, variant, or derivative thereof.

In some embodiments, teriflunomide or an analogue, variant, or derivative thereof is administered to the subject the form of a topical composition comprising from about 10 mg/ml to about 50 mg/ml, or about 20 mg/ml to about 30 mg/ml, or about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg/ml teriflunomide or an analogue, variant, or derivative thereof. In some embodiments, teriflunomide or an analogue, variant, or derivative thereof is administered to the subject the form of a topical composition comprising from about 1% to about 20%, or from about 5% to about 15%, or about 1.0, 1.1, 1.2, 1.3, 1.4, 1.5, 1.6, 1.7, 1.8, 1.9, 2.0, 2.25, 2.5, 2.75, 3.0, 3.25, 3.5, 3.75, 4.0, 4.25, 4.5, 4.75, 5.0, 5.5, 6.0, 6.5, 7.0, 7.5, 8.0, 8.5, 9.0, 9.5, 10, 10.5, 11, 11.5, 12, 12.5, 13, 15, 14, 14.5, 15, 15.5, 16, 16.5, 17, 17.5, 18, 18.5, 19, 19.5, or 20% teriflunomide or an analogue, variant, or derivative thereof.

In some embodiments, leflunomide or an analogue, variant, or derivative thereof is administered to the subject the form of a topical composition comprising from about 10 mg/ml to about 50 mg/ml, or about 20 mg/ml to about 30 mg/ml, or about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg/ml leflunomide or an analogue, variant, or derivative thereof. In some embodiments, leflunomide or an analogue, variant, or derivative thereof is administered to the subject the form of a topical composition comprising from about 1% to about 20%, or from about 5% to about 15%, or about 1.0, 1.1, 1.2, 1.3, 1.4, 1.5, 1.6, 1.7, 1.8, 1.9, 2.0, 2.25, 2.5, 2.75, 3.0, 3.25, 3.5, 3.75, 4.0, 4.25, 4.5, 4.75, 5.0, 5.5, 6.0, 6.5, 7.0, 7.5, 8.0, 8.5, 9.0, 9.5, 10, 10.5, 11, 11.5, 12, 12.5, 13, 15, 14, 14.5, 15, 15.5, 16, 16.5, 17, 17.5, 18, 18.5, 19, 19.5, or 20% leflunomide or an analogue, variant, or derivative thereof.

In some embodiments, pirfenidone or an analogue, variant, or derivative thereof is administered to the subject the form of a topical composition comprising from about 0.1 mg/ml to about 5 mg/ml, or from about 0.5 mg/ml to 2 mg/ml, or about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3.0, 3.25, 3.5, 3.75, 4.0, 4.25, 4.5, 4.75, or 5.0 mg/ml pirfenidone or an analogue, variant, or derivative thereof. In some embodiments, pirfenidone or an analogue, variant, or derivative thereof is administered to the subject the form of a topical composition comprising from about 0.1% to about 20%, or from about 1% to about 10%, or about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3.0, 3.25, 3.5, 3.75, 4.0, 4.25, 4.5, 4.75, 5.0, 5.5, 6.0, 6.5, 7.0, 7.5, 8.0, 8.5, 9.0, 9.5, 10, 10.5, 11, 11.5, 12, 12.5, 13, 15, 14, 14.5, 15, 15.5, 16, 16.5, 17, 17.5, 18, 18.5, 19, 19.5, or 20% pirfenidone or analogue, variant, or derivative thereof.

In some embodiments, captopril or an analogue, variant, or derivative thereof is administered to the subject the form of a topical composition comprising from about 0.1 mg/ml to about 5 mg/ml, or from about 0.5 mg/ml to about 2 mg/ml, or about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3.0, 3.25, 3.5, 3.75, 4.0, 4.25, 4.5, 4.75, or 5.0 mg/ml captopril or an analogue, variant, or derivative thereof. In some embodiments, captopril or an analogue, variant, or derivative thereof is administered to the subject the form of a topical composition comprising from about 1% to about 20%, or from about 5% to about 15%, or about 1.0, 1.1, 1.2, 1.3, 1.4, 1.5, 1.6, 1.7, 1.8, 1.9, 2.0, 2.25, 2.5, 2.75, 3.0, 3.25, 3.5, 3.75, 4.0, 4.25, 4.5, 4.75, 5.0, 5.5, 6.0, 6.5, 7.0, 7.5, 8.0, 8.5, 9.0, 9.5, 10, 10.5, 11, 11.5, 12, 12.5, 13, 15, 14, 14.5, 15, 15.5, 16, 16.5, 17, 17.5, 18, 18.5, 19, 19.5, or 20% captopril or an analogue, variant, or derivative thereof.

The anti-T cell agent and/or anti-TGF-β1 agent and/or anti-angiotensin agent can be administered according to any suitable dosing regimen, for example, where the daily dose is divided into two or more separate doses. It is within the skill of the ordinary artisan to determine a dosing schedule and duration for systemic or local administration. In some embodiments, the pharmaceutical composition is administered orally at least once a day or at least twice a day. In some embodiments, the pharmaceutical composition is administered intravenously at least once a day or at least twice a day. In some embodiments, the pharmaceutical composition is administered topically at least once a day or at least twice a day. In some embodiments, the pharmaceutical composition is administered subcutaneously at least once a day or at least twice a day.

In embodiments in which more than one active agent is administered, the agents can be administered together (for example, in the same formulation and/or at the same time), or separately (for example, in different formulations and/or at different times). In some such embodiments, the agents are administered systemically. In some such embodiments, the agents are administered locally. In some such embodiments, one (or more) agent is administered systemically and one (or more) agent is administered locally, for example, topically. Where two such agents are used, it is possible to use lower dosages or amounts of each agent, as compared to the dosages necessary when each agent is used alone.

Embodiments of the present disclosure can be further defined by reference to the following non-limiting examples. It will be apparent to those skilled in the art that many modifications, both to materials and methods, can be practiced without departing from the scope of the present disclosure.

EXAMPLES

Example 1. Treatment and Prevention of Lymphedema Using Tacrolimus

Tacrolimus Decreases Tail Lymphedema Without Systemic Immunosuppression

To study the effect of topical tacrolimus on lymphedema, we used a previously described mouse tail model of lymphedema. Goldman et al., *Circ. Res.* 96:1193-1199 (2005); Shimizu et al., *J. Am. Heart Assoc.* 2:e000438 (2013); Choi et al., *Circulation* 125:872-882 (2012); Tabibiazar et al., *PLoS Med.* 3:e254 (2006); Yoon et al., *J. Clin. Invest.* 111:717-725 (2003). Disruption of the superficial and deep lymphatics of the mouse tail resulted in a greater than 100% increase in tail volumes 2 weeks after surgery (FIG. 1 (A), (B)). We have previously shown that swelling at this time point is due primarily to accumulation of interstitial fluid. Avraham et al., *FASEB J.* 27:1114-1126 (2013). Chronic lymphatic obstruction in the tail results in gradual replacement of interstitial fluid by fibroadipose tissue, as well as accumulation of inflammatory cells occurs over the ensuing 4 weeks. Avraham et al., *FASEB J.* 27:1114-1126 (2013). These pathologic changes closely mirror clinical lymphedema and persist for at least 6-9 additional weeks once lymphedema is established. Goldman et al., *Circ. Res.* 96:1193-1199 (2005); Shimizu et al., *J. Am. Heart Assoc.* 2:e000438 (2013); Choi et al., *Circulation* 125:872-882 (2012); Tabibiazar et al., *PLoS Med.* 3:e254 (2006); Yoon et al., *J. Clin. Invest.* 111:717-725 (2003).

Based on this knowledge, we used two different tacrolimus treatment approaches. One group of animals were treated with tacrolimus beginning 2 weeks after surgery for 4 weeks (total of 6 weeks after tail surgery), in an effort to prevent development of lymphedema (i.e., early treatment). In another group we waited 6 weeks after lymphatic ablation for lymphedema to become established and then treated with tacrolimus until 9 weeks, with the intent to treat established soft tissue changes (i.e., late treatment). In all studies, we treated animals twice daily with either 0.1% tacrolimus (0.05 g/application) or vehicle control (petroleum jelly). Tacrolimus or vehicle control were applied as a thin layer to the entire tail distal to (i.e., not including) the surgical site.

Early treatment with topical tacrolimus markedly decreased tail swelling and prevented development of permanent swelling (FIG. 1 (A), B)). Gross examination of the tails from experimental animals demonstrated a near complete resolution of lymphedema and this change corresponded to a 95% decrease in tail volume and nearly 50% decrease in soft tissue thickness (FIG. 1 (B), (C)). Late treatment was also highly effective in decreasing gross tail swelling, tail volume, and soft tissue thickness, as compared with controls, although in these animals the tail volumes did not return to preoperative levels (FIG. 1 (B), (C)).

Figure 7:
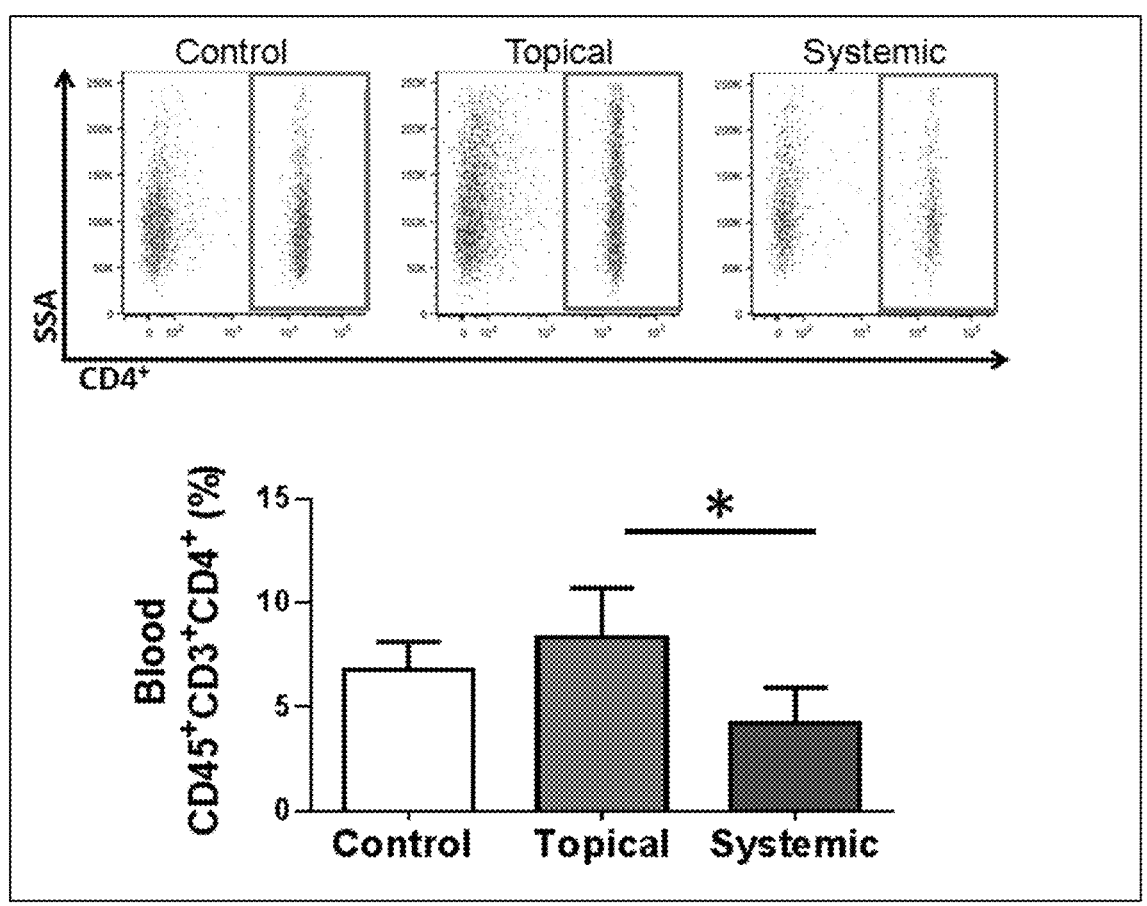
FIG. 7 shows that topical tacrolimus does not decrease circulating CD4$^+$ T cells. Representative flow plots of peripheral blood CD4$^+$ cells (upper panel) with quantification of CD4$^+$ T cells (lower panel) are shown after 2 week treatment with topical tacrolimus, systemic tacrolimus, or vehicle control.

We also analyzed systemic levels of tacrolimus and peripheral T cell counts to determine if topically applied tacrolimus is absorbed in an appreciable manner. This analysis demonstrated that systemic absorption of topical tacrolimus (mean value of 1.06 ng mL$^{-1}$) remained significantly below the known therapeutic immunosuppressive levels achieved with systemic administration (5-15 ng mL$^{-1}$; FIG. 1 (D)). In addition, animals treated with topical tacrolimus showed no changes in circulating blood T cells or CD4$^+$ cells (FIG. 1 (E), FIG. 7), as compared to vehicle treated controls.

Tacrolimus Decreases Inflammation and Fibrosis after Lymphatic Injury

Figure 2:
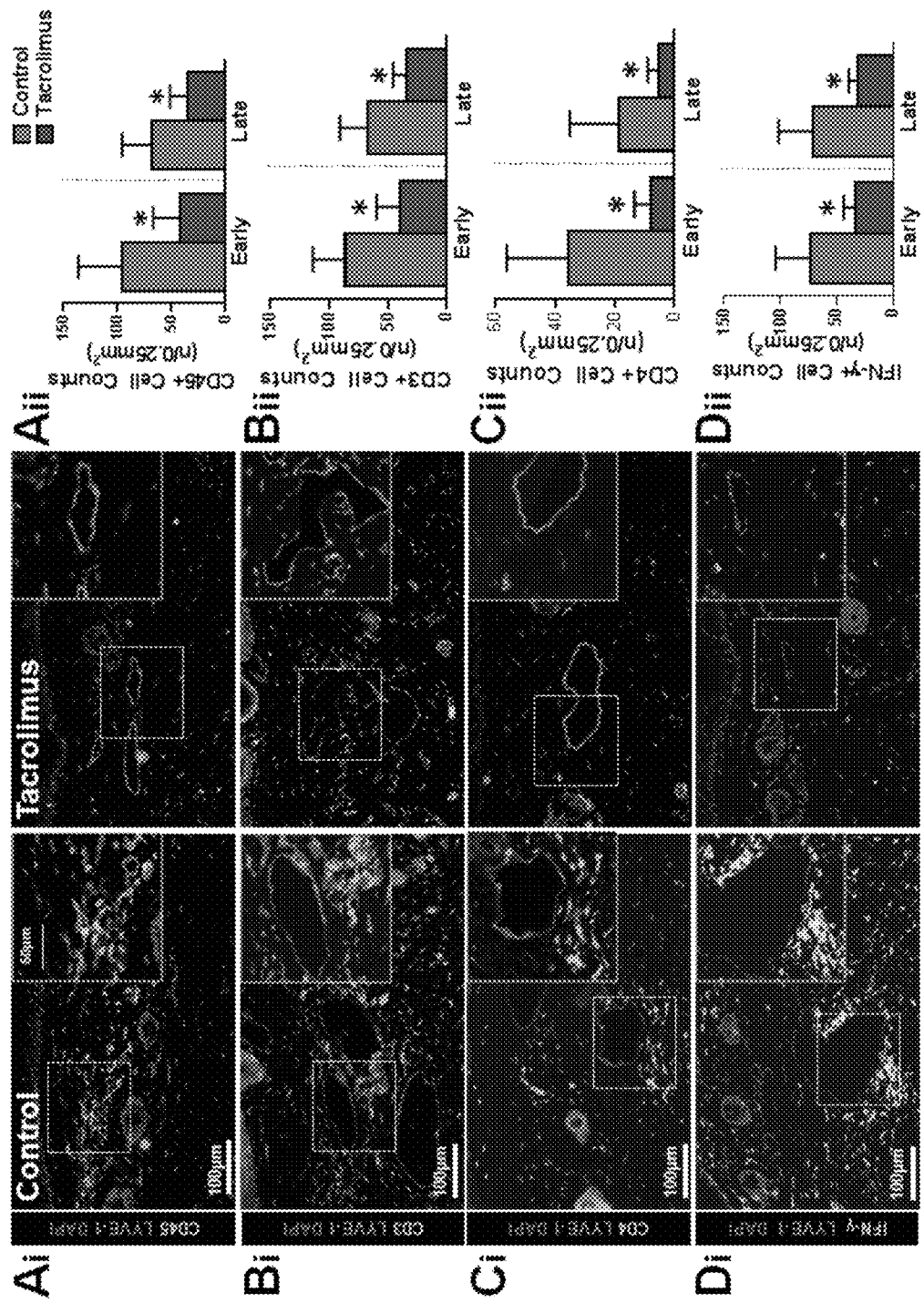
FIG. 2 shows that topical tacrolimus decreases inflammation after lymphatic injury. $(A_i)$, $(B_i)$, $(C_i)$, $(D_i)$ show representative 40× images of tail tissue sections harvested from control and tacrolimus-treated animals 6 weeks after surgery with immunofluorescent localization of $CD45^+$ $(A_i)$, $CD3^+$ cells $(B_i)$, $CD4^+$ cells $(C_i)$, and IFN-7$^+$ cells $(D_i)$. Higher-power (80×) images are shown in the top right corner inset of each figure. Lymphatic vessels are stained (LYVE-1) in each figure. Quantifications of cell counts for both early and late treatments are shown to the right of each figure in $(A_{ii})$, $(B_{ii})$, $(C_{ii})$, $(D_{ii})$ (p<0.001 for all).
Figure 8:
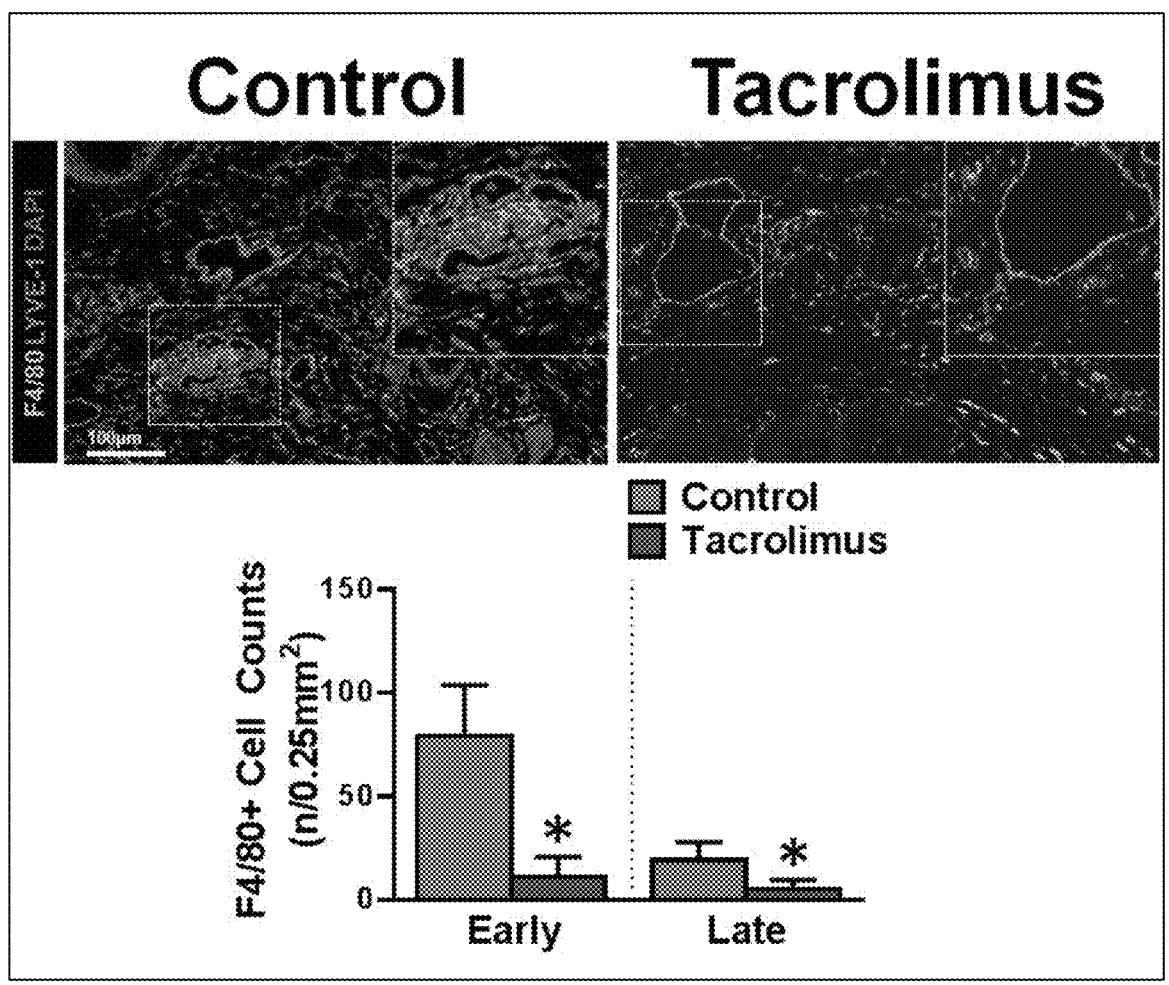
FIG. 8 shows that topical tacrolimus decreases macrophage infiltration in post-surgical lymphedema. Representative 40× images of tail tissue sections from control and early topical tacrolimus treated animals harvested 6 weeks after surgery with immunofluorescent localization of F4/80$^+$ cells are shown in the upper panels. Quantification for both early and late treatment experiments is shown below.

Chronic inflammation is a histological hallmark of clinical lymphedema and is characterized by increased accumulation of T-helper cells, T regulatory cells, and macrophages. Avraham et al., *FASEB J.* 27:1114-1126 (2013); Zampell et al., *PLoS ONE* 7:e49940 (2012); Ghanta et al., *Am. J. Physiol. Heart Circ. Physiol.* 308:H1065-1077 (2015); Olszewski et al., *Lymphology* 23:23-33 (1990). Consistent with this, we found that tacrolimus-treated animals had markedly decreased numbers of leukocytes infiltrating the dermis and subcutaneous fat as compared with controls (CD45$^+$ cells; 56% reduction-early treatment; 49% late treatment; FIG. 2 ($A_i$), ($A_{ii}$)). Inflammatory cells in lymphedematous tissues harvested from control animals were located in close proximity to the capillary and collecting lymphatics, but were virtually absent in tacrolimus treated mice. Similarly, we noted marked decreases in the numbers of infiltrating CD3$^+$ cells (53% reduction-early; 49% late treatment; FIG. 2 ($B_i$), ($B_{ii}$)), CD4$^+$ cells (78% reduction-early treatment, 71% late treatment; FIG. 2 ($C_i$), ($C_{ii}$)), and IFN-γ-producing cells (54% reduction-early treatment, 57% late treatment; FIG. 2 ($D_i$), ($D_{ii}$)). Additionally, we noted a decrease in the soft tissue infiltration of macrophages (F4/80$^+$ cells; 86% reduction-early treatment; 73% late treatment; FIG. 8). Taken together, these findings show that following lymphatic injury, inflammatory cells accumulate in large numbers in close proximity to skin/subcutaneous lymphatic vessels and that this response is mitigated by topical application of tacrolimus.

Figure 3:
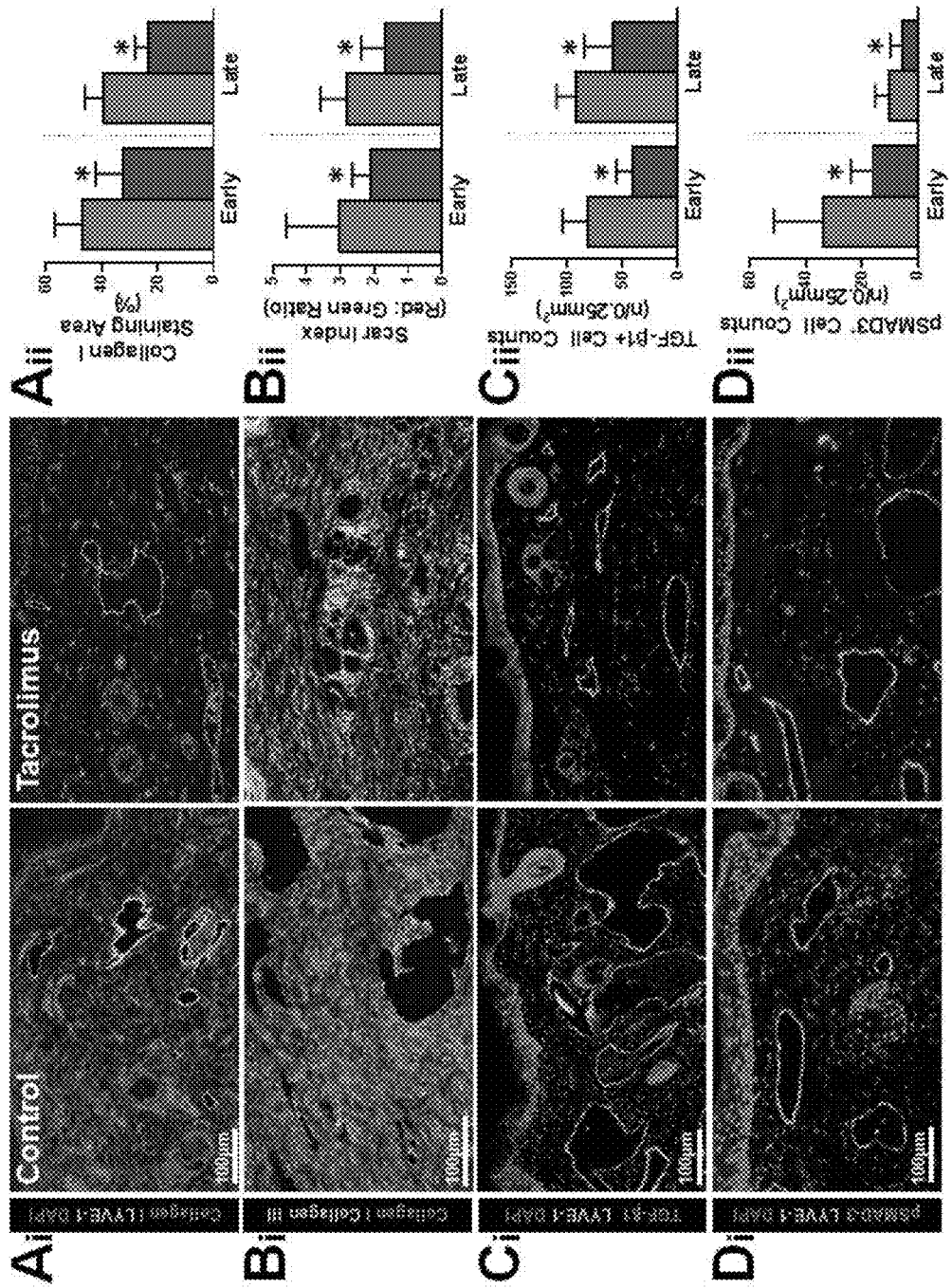
FIG. 3 shows that topical tacrolimus decreases fibrosis in lymphedema. $(A_i)$ shows representative 40× images of tail tissues harvested from control or early treatment with tacrolimus 6 weeks after surgery with immunofluorescent localization of type I collagen and lymphatic vessels. Quantifications of collagen I-staining area in both early and late treatment are shown to the right in $(A_{ii})$ (p<0.001 for both). $(B_i)$ shows representative 40× images of picrosirius red staining of tail tissues harvested from control and early tacrolimus treated animals (collagen I and collagen III deposition). Quantification of Scar Index (red:green ratio) is shown to the right in $(B_{ii})$ (p=0.036 early; p<0.001 late). $(C_i)$ and $(D_i)$ show representative 40× immunofluorescent co-localization of TGF-β1 or pSMAD3 with lymphatic vessel in tail tissues harvested from animals treated with control or early treatment with tacrolimus 6 weeks after surgery. Quantification of the number of positive cells/0.25 mm$^2$ area for both is shown to the right of each figure in $(C_{ii})$ and $(D_{ii})$.

Patients with lymphedema have progressive soft tissue fibrosis and the degree of fibrosis correlates with the severity of disease. Tassenoy et al., *Lymphat. Res. Biol.* 7:145-151 (2009). Therefore, we analyzed several markers of fibrosis in the tail tissues to understand the effects of tacrolimus treatment on this aspect of the disease. We found that topical treatment with tacrolimus markedly decreased dermal and subcutaneous type I collagen deposition and Scar index (picrosirius red birefringence measuring the ratio of collagen/III), as compared with control mice (FIG. 3 ($A_i$), ($A_{ii}$), ($B_i$), ($B_{ii}$)). Lymphatic vessels of control mice were surrounded by thick layers of type I collagen; in contrast, tacrolimus-treated animals had essentially normal lymphatic vessels. Consistent with this observation and our previous reports (Clavin et al., *Am. J. Physiol. Heart Circ. Physiol.* 295:H2113-2127 (2008)), we also found that tacrolimus treatment markedly decreased expression of the pro-fibrotic growth factor TGF-β1 and cellular expression of its activated downstream signaling molecule, phosphorylated SMAD3 (pSMAD-3; FIG. 3 ($C_i$), ($C_{ii}$), ($D_i$), ($D_{ii}$)). The degree of this response was similar for both early and late tacrolimus treatments.

Tacrolimus Increases Lymphatic Function

Figure 4:
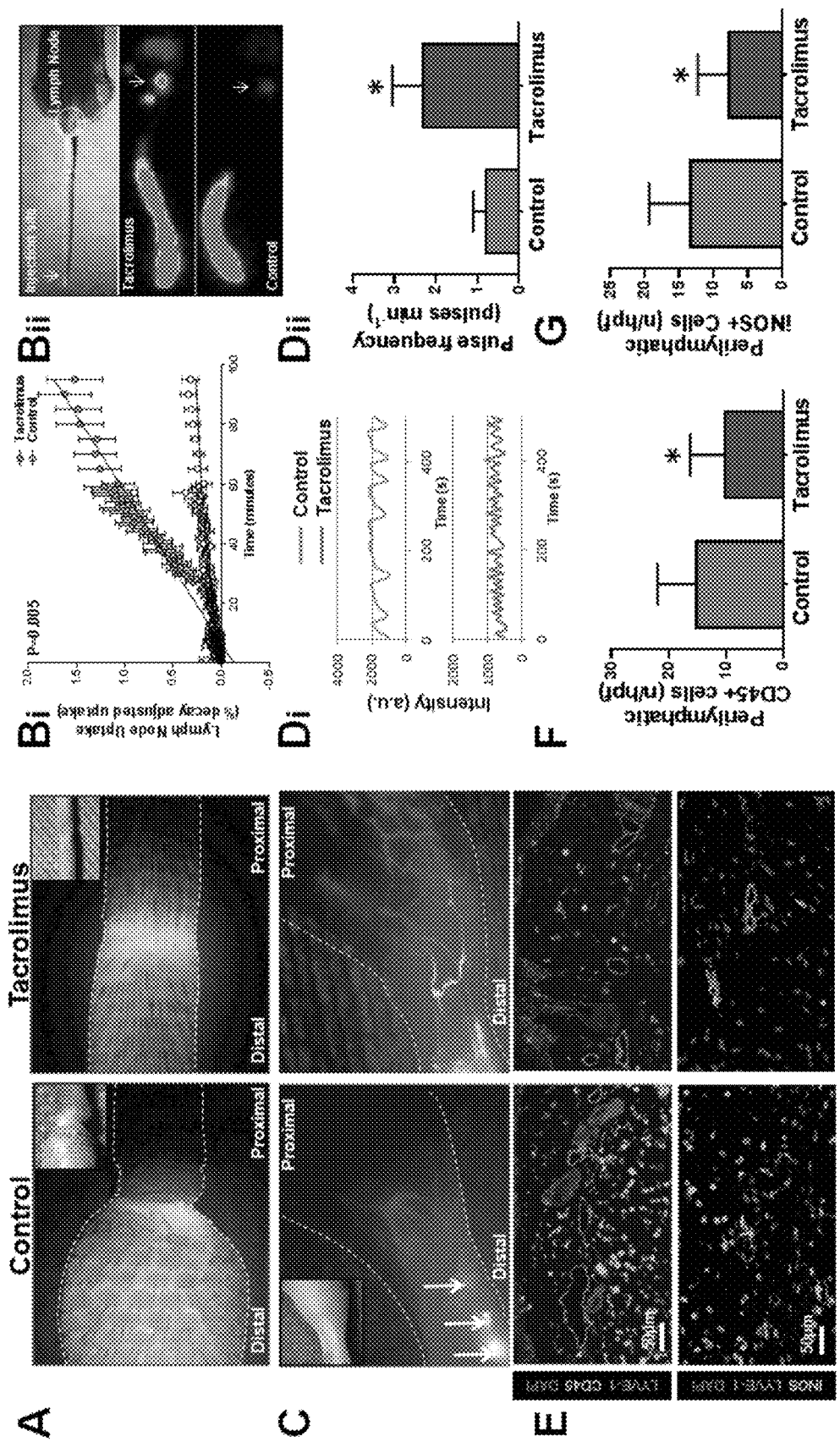
FIG. 4 shows that tacrolimus improves lymphatic function after surgical lymphatic injury. (A) shows representative ICG images of mouse tails 6 weeks after surgery following early treatment with or without tacrolimus. Note flow of ICG proximally across the wound in tacrolimus treated animals. Inset shows photograph of same mice for orientation. ($B_i$) and ($B_{ii}$) show decay-adjusted uptake of $^{99m}$Tc by sacral lymph nodes 6 weeks after surgical ligation of superficial/deep lymphatics in control and early tacrolimus (beginning 2 weeks after surgery) treated animals (*p=0.005). Gross photographs of mouse tails shown in the upper panel of ($B_{ii}$) are for orientation and show site of $^{99m}$Tc injection and location of sacral lymph nodes; representative heat maps are shown in the lower panel with the white arrow pointing toward the sacral lymph nodes. (C) shows representative ICG images of hind limbs obtained 50 minutes after distal foot injection in mice treated with or without tacrolimus 4 weeks after PLND. White arrows show dermal backflow of ICG. Inset photograph shows orientation. ($D_i$) and ($D_{ii}$) are graphical representations of lymphatic vessel pulsations in hind limb collecting vessels of mice treated with or without tacrolimus 4 weeks after PLND. Quantification of pulsation frequency is shown to the right (*p=0.001). (E) shows representative 40× fluorescent co-localization images of inflammatory cells (CD45$^+$; upper panel), iNOS$^+$ cells (lower panel) and lymphatic vessels (LYVE-1+) in tissues harvested from the distal hind limbs of animals treated with control or tacrolimus 4 weeks after PLND. Note peri-lymphatic accumulation of CD45$^+$ and iNOS$^+$ cells. (F) and (G) show quantification of peril-lymphatic CD45$^+$ cells ((F) and iNOS$^+$ cells ((G) in distal hind limb tissues of control or tacrolimus treated animals harvested 4 weeks after PLND.

To assess lymphatic function we performed Near infrared (NIR) lymphangiography with indocyanine green (ICG), which has been described as an effective means of quantifying lymphatic function in humans, pigs, and mice by enabling real-time imaging of lymphatic vessels, calculation of packet frequency (or pulsatile flow of lymphatic fluid), and analysis of dermal back flow and dye clearance. Kwon et al., *Lymphat. Res. Biol.* 5:219-231 (2007); Sharma et al., *Am. J. Physiol. Heart Circ. Physiol.* 292:H3109-3118 (2007); Unno et al., *J. Vasc. Surg.* 52:946-952 (2010). Using NIR imaging 6 weeks after lymphatic ligation, we noted rapid transport of interstitial fluid proximally across the tail wound in animals in which treatment was started 2 weeks after lymphatic injury (early treatment; FIG. 4 (A)). In contrast, control animals demonstrated pooling of ICG distal to the lymphatic excision site with no transport across the zone of injury. This finding was confirmed using technetium-99m ($^{99m}$Tc) lymphoscintigraphy, a technique in which a radiotracer is injected in the distal tail and uptake by the sacral lymph nodes is measured over time. Decay adjusted uptake of the sacral lymph nodes in the early treatment animals demonstrated a more than 6-fold increase in $^{99m}$Tc uptake in tacrolimus-treated animals as compared with controls (FIG. 4 ($B_i$), ($B_{ii}$)). Late treatment with tacrolimus similarly increased nodal uptake (2-fold); however, this difference did not reach statistical significance.

Figure 9:
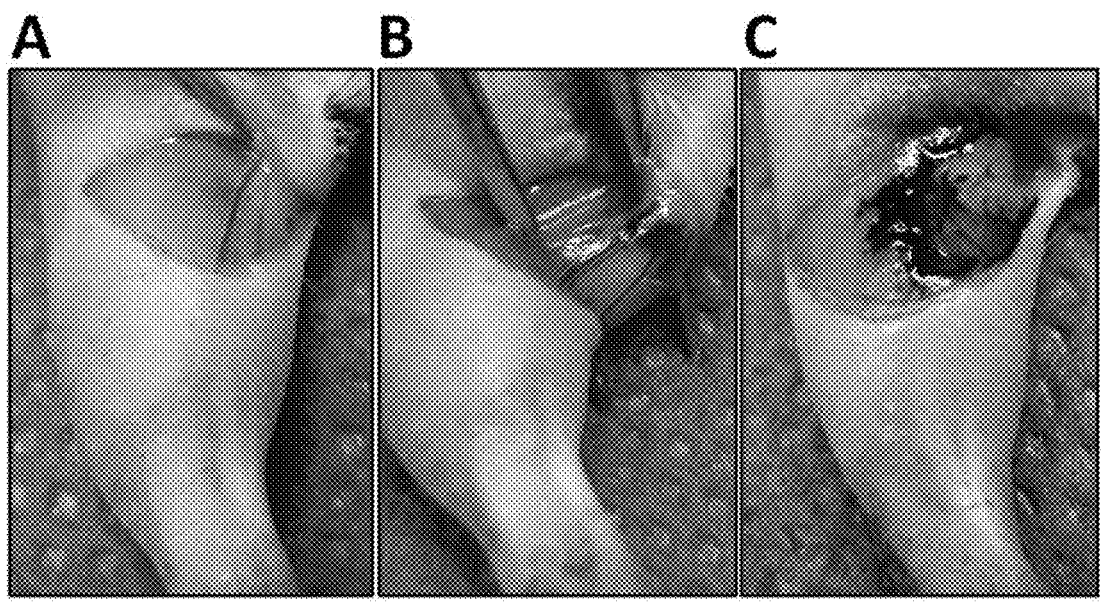
FIG. 9 shows the popliteal lymph node dissection model. (A) shows the popliteal lymph node, filled with Evan's Blue contrast, visible in the popliteal fat pad. (B) shows that the popliteal lymph node, together with afferent and efferent collectors, is isolated with its surrounding fat pad. (C) shows Evan's blue contrast spilling freely in the surgical site, following surgical resection.

Given the efficacy of tacrolimus in preventing and treating lymphedema in the tail model, we next sought to study how tacrolimus modulates lymphatic function after lymphatic injury using a previously described model of popliteal lymph node dissection (PLND) (FIG. 9 (A)-(C)). Blum et al., *Breast Cancer Res. Treat.* 139:81-86 (2013). This model is clinically relevant since lymph node dissection in the course of cancer treatment is the most common cause of lymphedema in developed countries. We first utilized the PLND mouse model to better understand the mechanisms by which chronic inflammatory reactions are activated after lymphatic injury.

Figure 10:
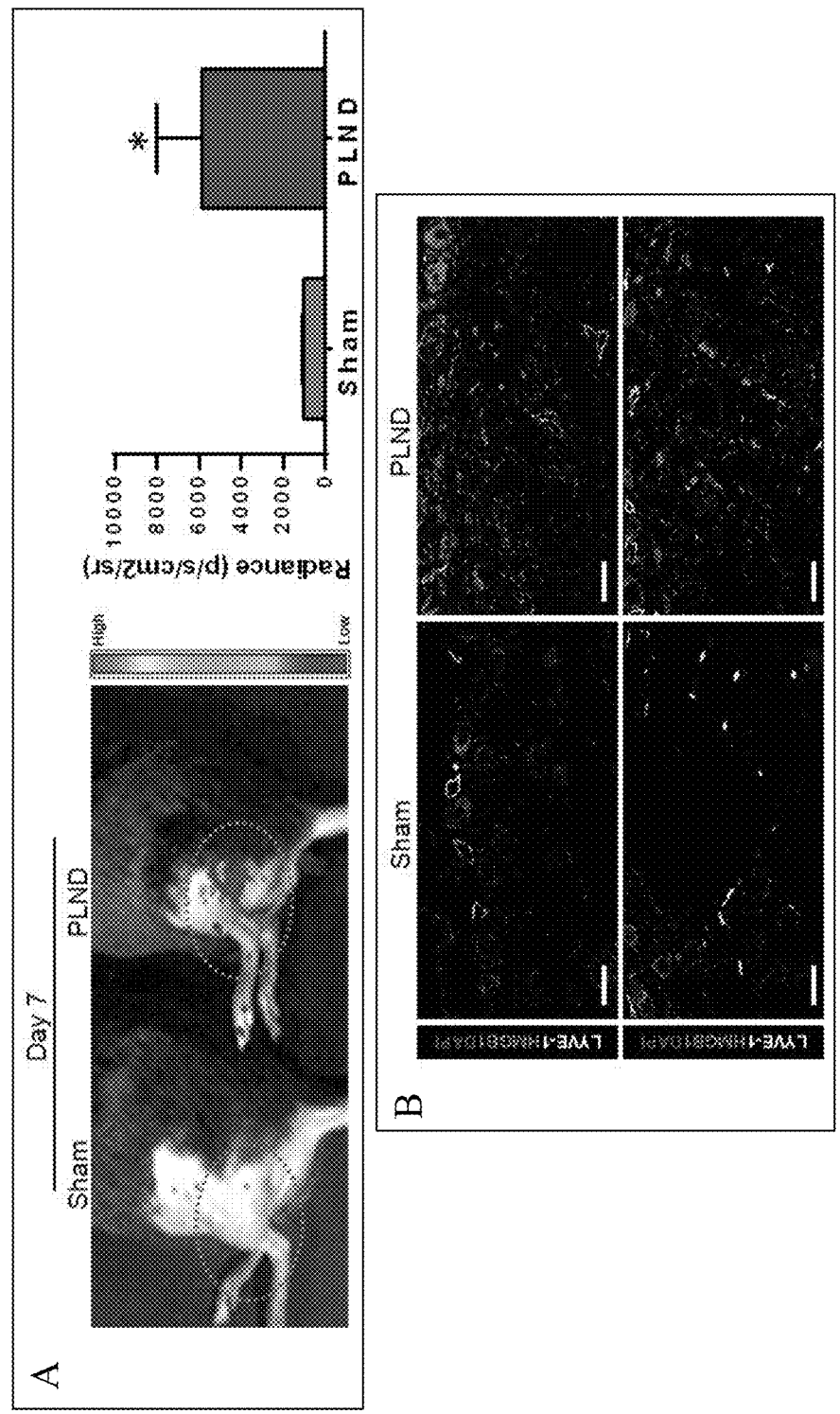
FIG. 10 shows that PLND results in increased ROS and DAMPs as compared to Sham control limbs. (A) shows representative mouse images (left panel) showing luminescence (indicating ROS) in hindlimb immediately after PLND (6 hrs) and 1 wk later. Quantification of the luminescent photons (right panel) shows significantly increased ROS levels in PLND areas but not in sham at 1 wk. (B) shows representative immunofluorescent images of hind limb skin sections from sham and PLND mice stained for HSP-70 (top panel) and HMGB1 (lower panel).

Previous studies have demonstrated that lymphatic endothelial cells (LECs) are highly sensitive to reactive oxygen species (ROS) (Kasuya et al., *Sci. Rep.* 4:4173 (2014)) and that ROS can activate chronic inflammation. Gorlach et al., *Redox Biol.* 6:372-385 (2015). To determine whether ROS are present following PLND, we analyzed accumulation of ROS in tissues distal to the zone of injury 1 week after injury based on the known role of lymphatic vessels in removing cellular metabolic products. Indeed, this analysis demonstrated a significant accumulation of ROS in the hind limb tissues immediately distal to the popliteal region in animals treated with PLND (FIG. 10 (A)). In contrast, control animals that had been treated with skin incision without lymphadenectomy had virtually no accumulation of ROS. ROS can activate innate immune responses including danger-associated molecular pattern molecules (DAMPs). Yin et al., *J. Immunol.* 194:429-437 (2015). Consistent with these studies and our finding of increased ROS after PLND, as well as with our previous studies using a tail model of lymphedema in which we demonstrated increased expression of HMGB1 in a variety of cell types in lymphomatous tissues (Zampell et al., *Am. J. Physiol. Cell Physiol.* 300:C1107-1121 (2011)), we noted a marked increase in the expression of DAMPs such as heat shock protein-70 (HSP70) and high-mobility group box 1 (HMGB-1) (FIG. 10 (B)). These findings indicate that lymphatic injury results in generation of ROS, which in turn, result in cellular injury, expression of DAMPs, and initiation of inflammatory responses.

Previous clinical and laboratory studies have described dermal backflow as pooling of ICG into the interstitial space resulting from leaky, dysfunctional lymphatics. Blum et al., *Breast Cancer Res. Treat.* 139:81-86 (2013); Tashiro et al., *Ann. Plast. Surg.* doi: 10.1097/SAP.599 (2015); Yamamoto et al., *Plast. Reconstr. Surg.* 128:314e-321e (2011). Consistent with these reports, we found that control animals treated topically with petroleum jelly alone for 4 weeks had marked leakiness of the initial lymphatics of the foot pad (punctate areas of bright ICG accumulation indicated by white arrows; FIG. 4 (C)) and dermal back flow (generalized retention of ICG in the dermis; FIG. 4 (C)). This pathologic response was markedly decreased in animals treated with topical tacrolimus resulting in decreased lymphatic leakiness and improved clearance of injected ICG.

Analysis of fluctuations in ICG florescence intensity in the collecting vessels using time lapse photography is a technique that has been previously used to measure the rate of lymphatic pumping. Sevick-Muraca et al., *J. Cin. Invest.* 124:905-914 (2014). This analysis enables calculation of "ICG packet frequency" and has been used to analyze collecting lymphatic function after PLND. Blum et al., *Breast Cancer Res. Treat.* 139:81-86 (2013). Using this technique, we found that topical tacrolimus therapy markedly increased collecting lymphatic packet frequency as compared with controls (>2-fold increase) indicating that this treatment increases collecting lymphatic function (FIG. 4 (Di), (Dii)).

Figure 11:
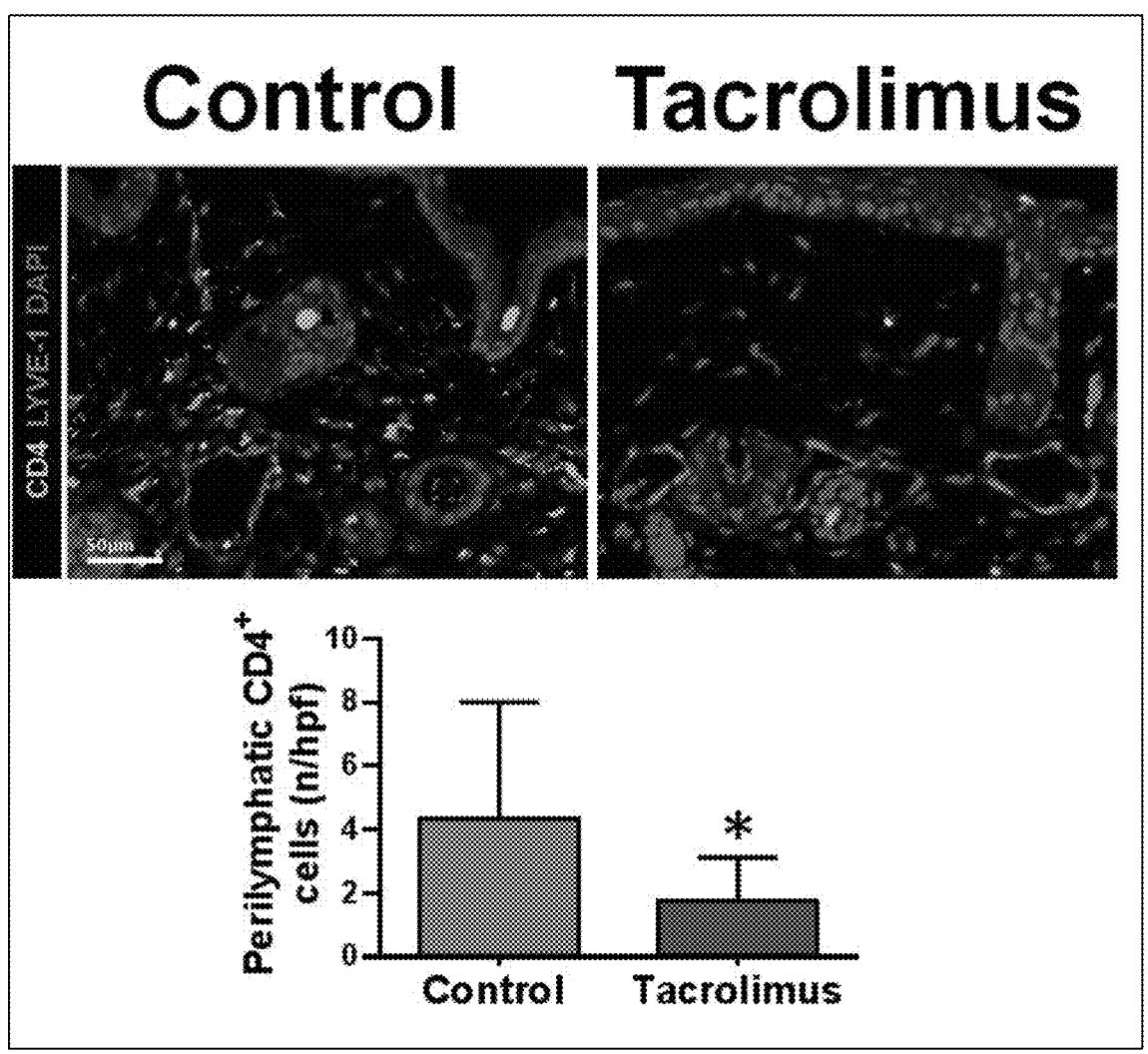
FIG. 11 shows that topical tacrolimus decreases perilymphatic CD4$^+$ cell infiltration after PLND. The upper panels show representative images of immunofluorescent localization of CD4$^+$ cells and lymphatic vessels (LYVE-1+) in animals treated with control or tacrolimus and harvested 4 weeks after PLND. Quantification is shown below.
Figure 12:
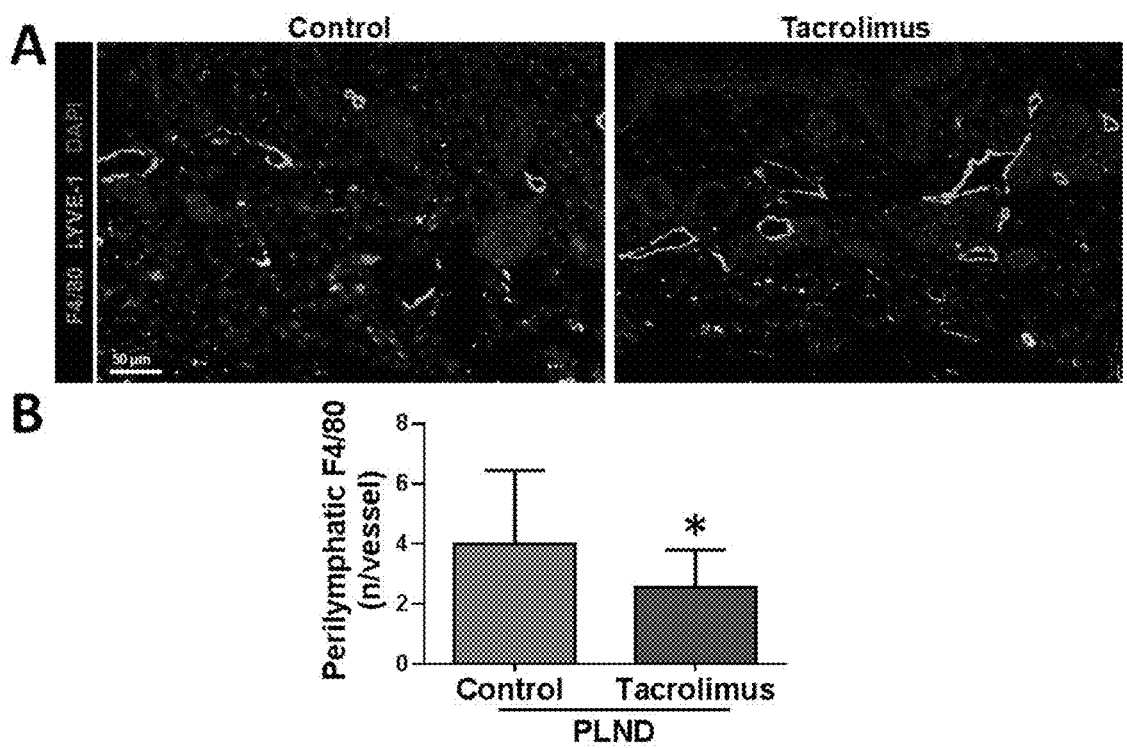
FIG. 12 shows that topical tacrolimus decreases perilymphatic F4/80 cell infiltration after PLND. (A) shows representative immunofluorescent images of tacrolimus and vehicle treated PLND hindlimb skin tissues sections stained for lymphatic vessels (LYVE-1) and macrophages (F4/80). (B) shows quantification of the perilymphatic F4/80+ macrophages.
Figure 13:
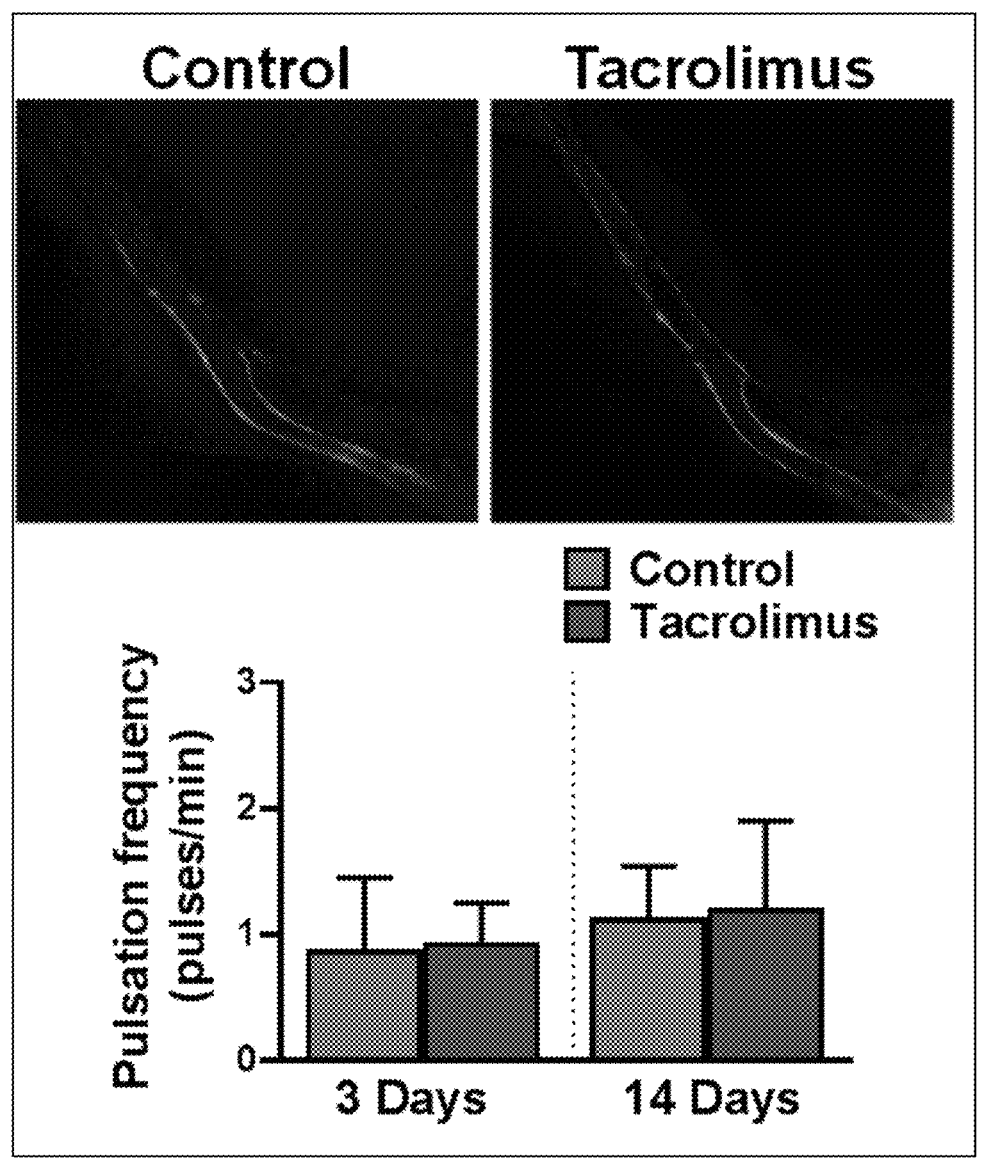
FIG. 13 shows that topical tacrolimus does not alter collecting lymphatic vessel pulsation or lymphangiogenesis in the absence of lymphatic injury or inflammation. Upper panels are representative images of NIR lymphatic images of the hind limb lymphatics in sham operated mice (i.e., anesthesia without incision or PLND) following treatment with control or topical tacrolimus for 2 weeks. Quantification of collecting lymphatic vessel pulsation frequency following 3 or 14 days of treatment with tacrolimus is shown below.

In addition, similar to our findings with the tail model, we found that treatment with topical tacrolimus after PLND markedly decreased perilymphatic infiltration of inflammatory cells (39% reduction in $CD45^+$ cells (FIG. 4 (E) upper panel, FIG. 4 (F)) 56% reduction in $CD4^+$ cells (FIG. 11) and 36% reduction in $F4/80^+$ cells (FIG. 12 (A), (B)) compared to vehicle treated controls. Treatment with topical tacrolimus also resulted in a significant decrease in perilymphatic expression of inducible nitric oxide synthase (iNOS) by inflammatory cells (42% reduction in the number of iNOS-expressing cells) (FIG. 4 (E) lower panel, FIG. 4 (G)). This is important since previous studies have shown that perilymphatic iNOS expression is an important regulator of collecting lymphatic pumping capacity. Liao et al., *Proc. Natl. Acad. Sci. USA* 108:18784-18789 (2011). Importantly, changes in lymphatic contractility in response to topical tacrolimus treatment were only observed in the setting of lymphatic injury since treatment of non-operated animals (i.e., anesthesia only but no surgery) with tacrolimus did not increase lymphatic contraction frequency or perilymphatic accumulation of inflammatory cells (FIG. 13).

Figure 14:
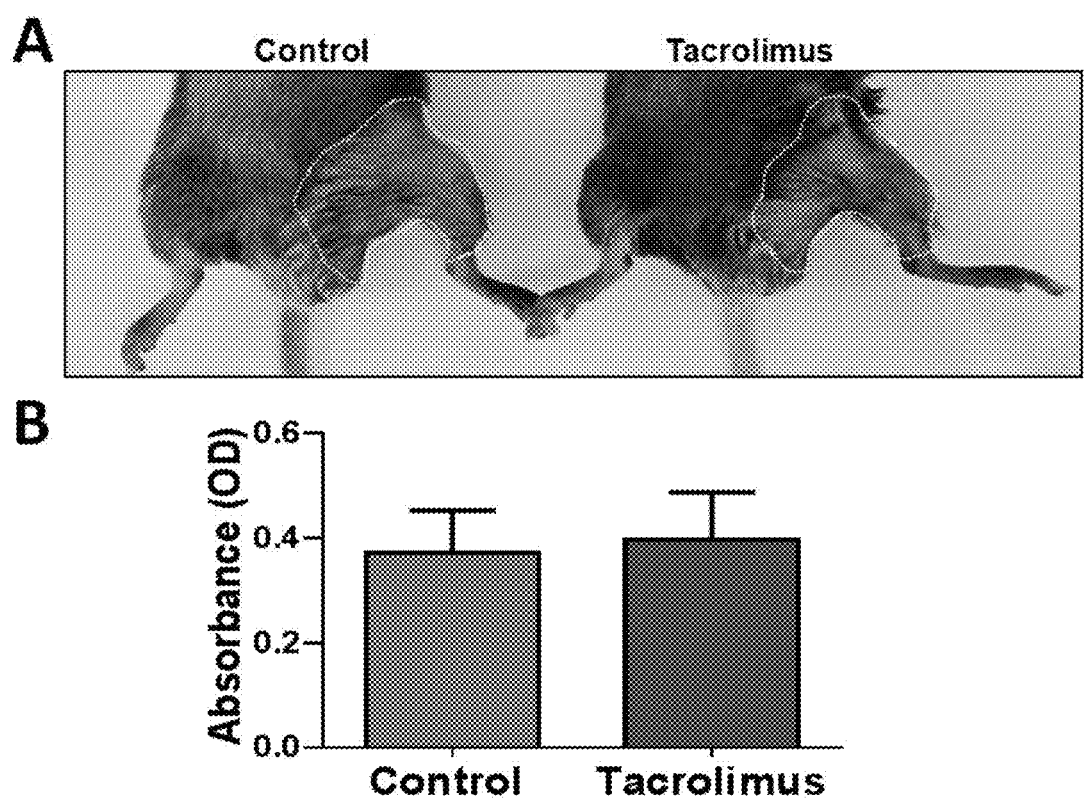
FIG. 14 shows that topical tacrolimus treatment does not alter vascular permeability following lymphatic injury. (A) shows representative gross images of tacrolimus or vehicle treated PLND mice hindlimbs after tail vein Evans blue injections to measure vascular permeability. (B) shows quantification of absorbance of formamide extracted Evans blue from tacrolimus and vehicle treated PLND hind limb tissues.

Additionally, to ensure that the observed effects of tacrolimus on lymphatic function were not a result of decreased vascular permeability and blood vessel leakage, we performed a Miles assay to measure blood vessel permeability following PLND surgeries with and without tacrolimus. We observed no differences in blood vessel permeability between tacrolimus treated and vehicle control, suggesting that the effects of tacrolimus in increasing lymphatic function are indeed due to increased lymphatic function rather than decreased vascular leakage (FIG. 14 (A), (B)).

Figure 15:
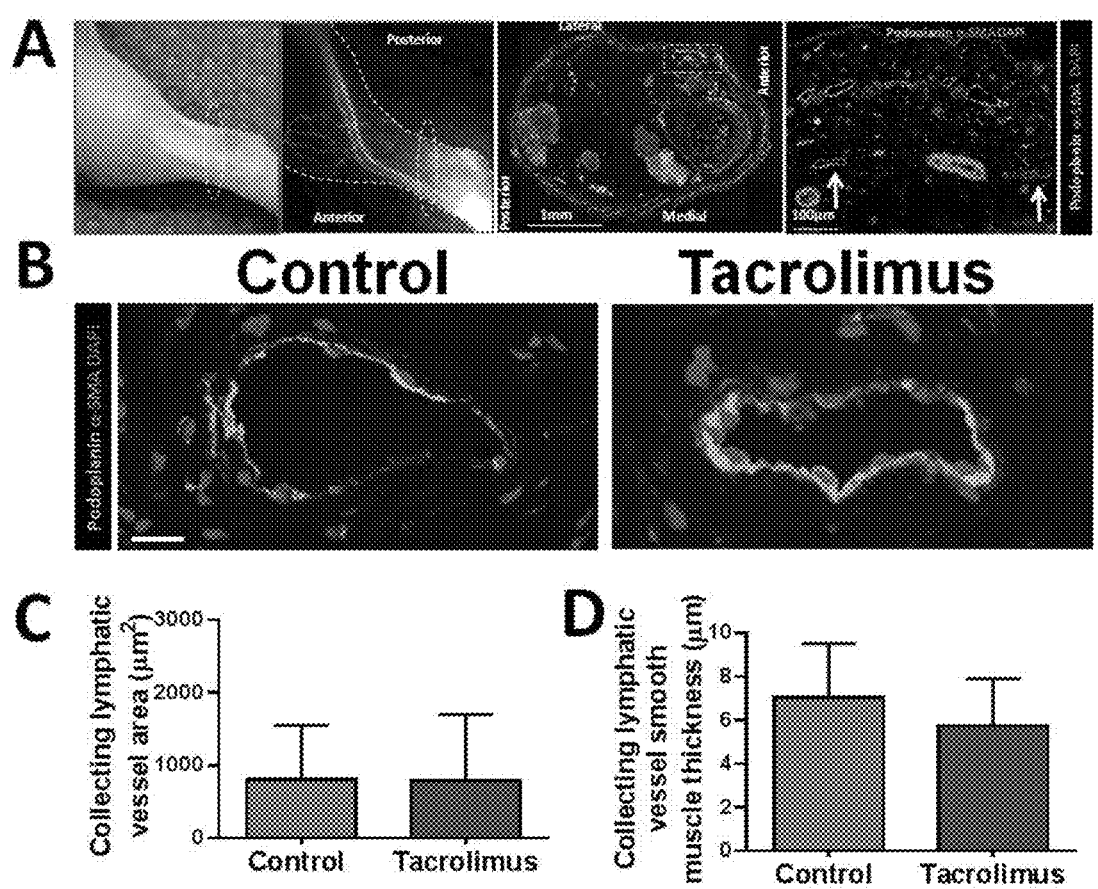
FIG. 15 shows that topical tacrolimus after PLND does not alter α-SMA coverage or luminal diameter of hind limb lymphatic collectors. (A) shows (from left to right) brightfield image of the lateral aspect of a mouse hind limb with the level of the cross-sections shown by the yellow ellipse; NIR image of a mouse hind limb showing the anatomy of lymphatic vessels of the hind limb, with two large-caliber vessels on the lateral aspect; 5× IF image of a mouse hind limb with a yellow box indicating the anterolateral leg, where the two dominant collecting lymphatic vessels are located; 20× image of the region in which the dominant collecting vessels are located (shown with white arrows). (B) shows representative 100× images of cross-sections of the collecting lymphatic vessels after dual immunofluorescent staining for Podoplanin and α-SMA. (C) shows quantification of luminal area. (D) shows quantification of the thickness of α-SMA.

We next examined luminal diameter and alpha smooth muscle cell coverage of the hind limb collecting lymphatics following PLND in control and tacrolimus treated animals based on the fact that previous clinical reports have shown that patients with long-standing severe lymphedema constricted lymphatics with smooth muscle cell hypertrophy. Mihara et al., *PLoS One* 7:e41126 (2012). Not surprisingly, in this relatively early time period after lymphatic injury (i.e., 4 weeks), we found no differences in the number of alpha smooth muscles surrounding the vessels or in the luminal area of hind limb collectors when comparing tacrolimus and control treated mice. This finding indicates that increases in collecting lymphatic packet frequency after tacrolimus treatment are not regulated by lymphatic structural changes but rather due to changes in the lymphatic microenvironment (e.g., perilymphatic inflammation or expression of iNOS; FIG. 15 (A)-(D)).

Tacrolimus Increases Collateral Lymphatic Vessel Formation

Figure 5:
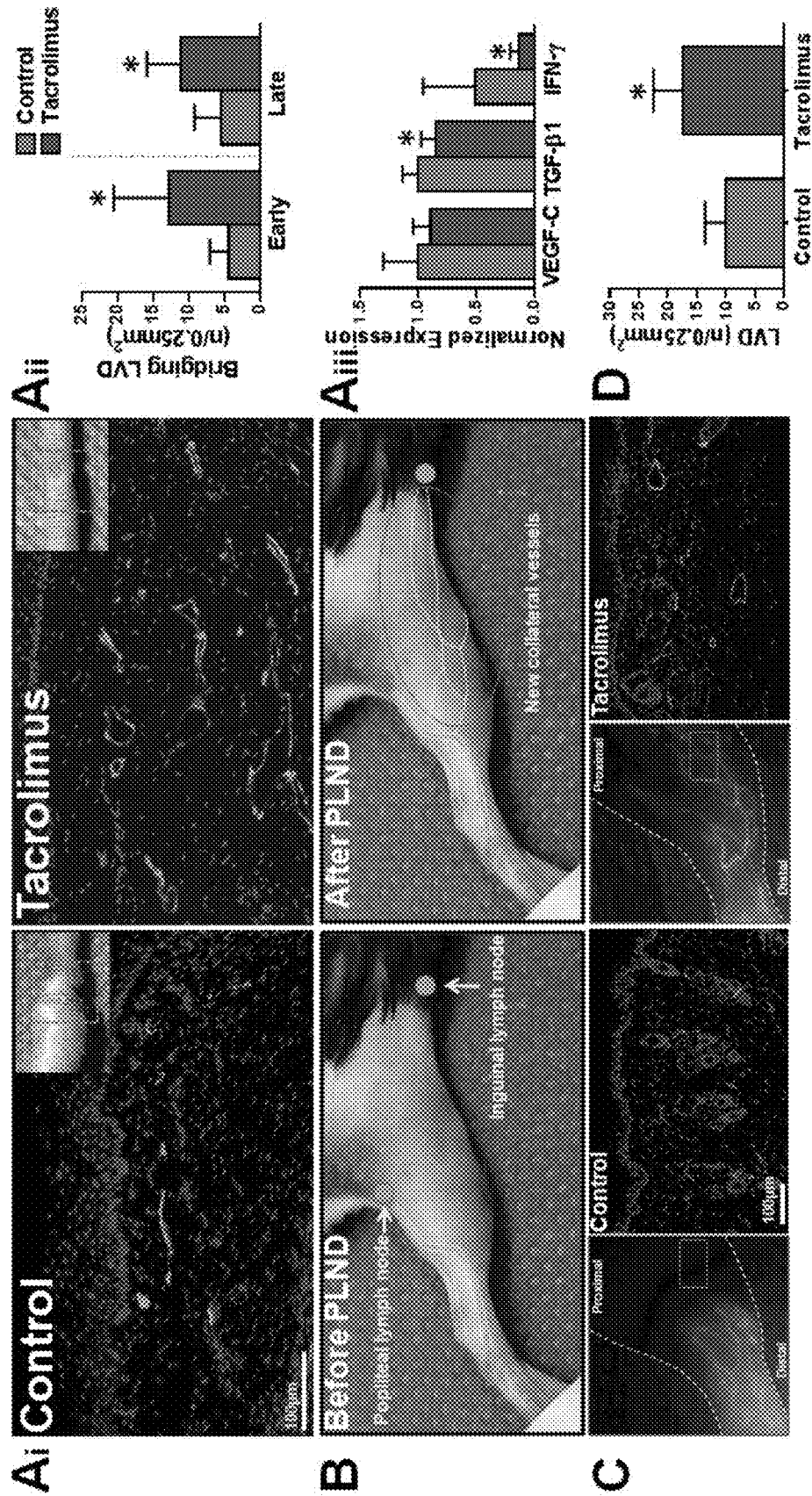
FIG. 5 shows that topical tacrolimus increases formation of collateral lymphatic vessels after lymphatic injury. ($A_i$) shows representative longitudinal immunofluorescent 40× images of LYVE-1 vessels bridging the surgically created tail wounds of control and early treated tacrolimus mice harvested 6 weeks after lymphatic injury; inset shows area where longitudinal sections were obtained. ($A_{ii}$) shows quantification of bridging lymphatic vessel density (LVD) in the wounded portion of the tail in control versus early or late treated tacrolimus mice (p<0.001 for both). ($A_{iii}$) shows qPCR of RNA harvested from control and early treated tacrolimus mouse tail tissues harvested 6 weeks after lymphatic injury, demonstrating relative expression of VEGF-C (p=0.264), TGF-β1 (p=0.006), and IFN-7 (p=0.014). (B) is a photograph of mouse hind limb showing site of collateral vessel formation draining towards the inguinal lymph nodes before and after PLND. (C) shows representative ICG (left panels) and 40× immunofluorescent images of LYVE-1$^+$ vessels (right panel showing area in box) in control and tacrolimus treated animals 4 weeks following PLND. (D) shows quantification of collateral lymphatic LVD in the aterolateral thigh region of animals treated with control or tacrolimus (p<0.001).

Because T cells are known to potently inhibit lymph node lymphangiogenesis (Kataru et al., *Immunity* 34:96-107 (2011)) and inflammatory lymphangiogenesis during wound repair (Zampell et al., *Am. J. Physiol. Cell Physiol.* 302: C392-C404 (2012)), we next sought to determine if treatment with tacrolimus increases the formation of collateral lymphatics. Indeed, histological analysis of tail wounds and identification of lymphatics using LYVE-1 immunofluorescent (IF) staining demonstrated a marked increase in newly formed lymphatic vessels bridging the zone of lymphatic injury (189% increase after early treatment; 106% increase after late treatment; FIG. 5 ($A_i$), ($A_{ii}$)). This lymphangiogenic response appeared to be independent of VEGF-C expression since we noted no differences in VEGF-C mRNA expression between control and tacrolimus treated animals (FIG. 5 ($A_i$)). However, consistent with our IF staining analysis, we noted a significant decrease in the expression of two potently anti-lymphangiogenic growth factors and cytokines, TGF-β1 (Oka et al., *Blood* 111:4571-4579 (2008); Clavin et al., *Am. J. Physiol. Heart Circ. Physiol.* 295: H2113-2127 (2008)) and IFN-γ (Kataru et al., *Immunity* 34:96-107 (2011); Shao et al., *J. Interferon Cytokine Res.* 26:568-574 (2006)) (FIG. 5 ($A_{iii}$)). Lymphangiographic analysis by NIR imaging, and IF staining for lymphatic vessels in hind limbs 4 weeks following PLND, confirmed our tail model findings demonstrating that animals treated with tacrolimus consistently had significantly more collateral lymphatics draining towards the inguinal lymph node, thereby bypassing the zone of injury (FIG. 5 (B)-(D)).

Figure 6:
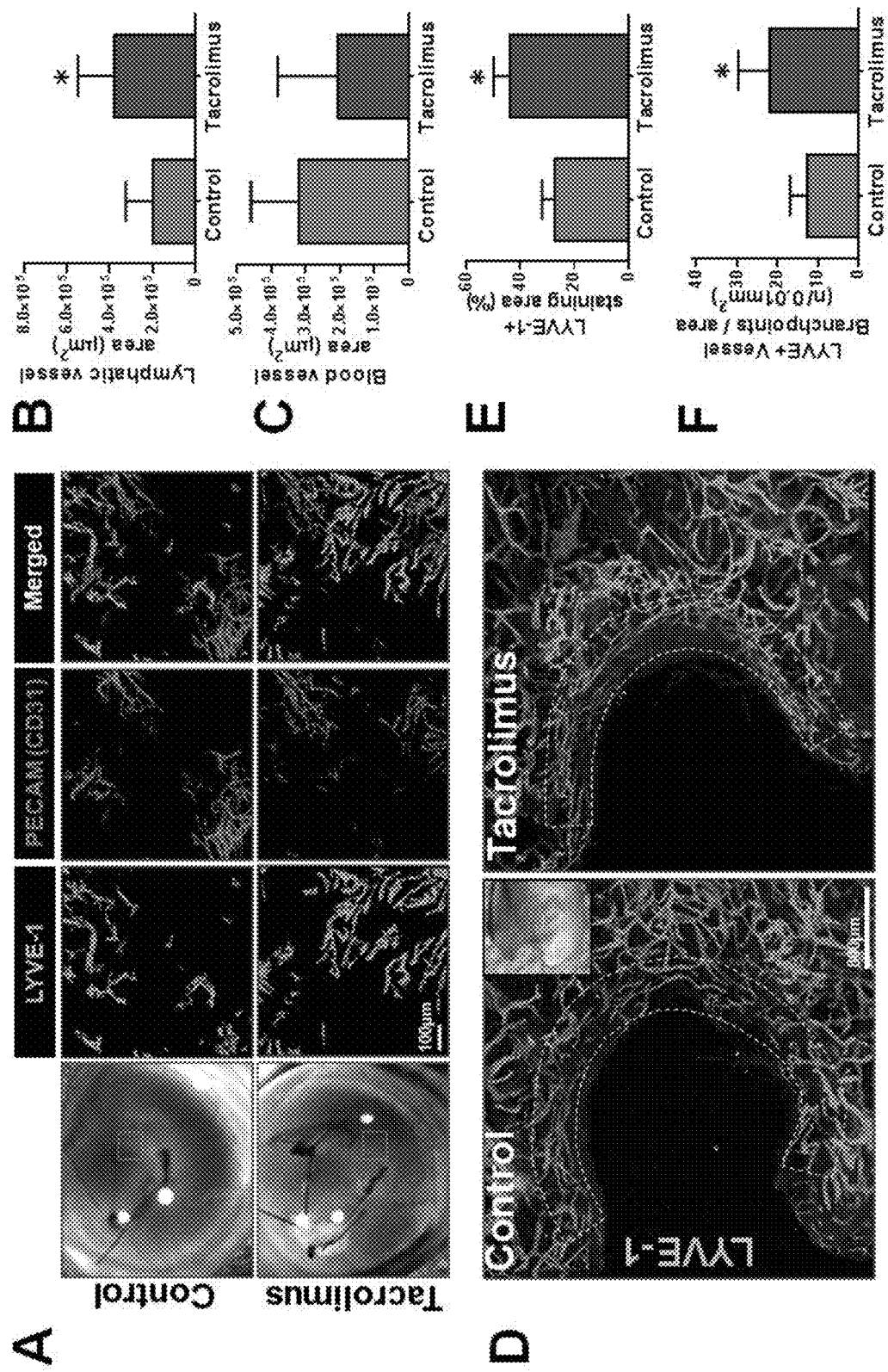
FIG. 6 shows that tacrolimus increases inflammatory lymphangiogenesis. (A) Representative gross (left panels) and whole mount 5× images (right panels) of mouse corneas stained for lymphatic vessels (LYVE-1$^+$/weakly CD31V) and blood vessels (CD31$^+$/LYVE-1$^-$) harvested 2 weeks after suture placement and treatment either with vehicle control or systemic tacrolimus. Box denotes area shown in whole mount images. (B) and (C) show quantification of corneal lymphatic (LYVE-V) and blood (CD31$^+$/LYVE-1$^-$) vessels. (D) shows representative florescent whole mount 5× images of ear wounds localizing LYVE-1$^+$ in control or topical tacrolimus treated animals harvested 4 weeks after wounding. Inset photograph shows area where sections were obtained. (E) shows quantification of the LYVE-1$^+$ staining area in ear skin (within 400 µm of the wound) demonstrating an increase in lymphangiogenesis in tacrolimus treated animals (p<0.001). (F) shows quantification of lymphatic vessel branch-points per unit area in ear wounds treated with or without tacrolimus demonstrating increased branching in tacrolimus treated animals (p<0.001).

To determine the lymphangiogenic effects of tacrolimus in other inflammatory and wound models in which drainage of lymphatic fluid is not obstructed surgically, we next used two other models of inflammatory lymphangiogenesis. The cornea is a useful tissue for studying lymphangiogenesis because it is normally devoid of both blood and lymphatic vessels but develops both in the setting of inflammation. Cursiefen et al., *J. Clin. Invest.* 113:1040-1050 (2004). We placed sutures in the corneas of mice and treated them with systemic tacrolimus or vehicle control daily for 2 weeks and found that tacrolimus treatment resulted in a significant increase in the proliferation of lymphatic (48% increase) but not blood vessels (FIG. 6 (A)-(C)).

Figure 16:
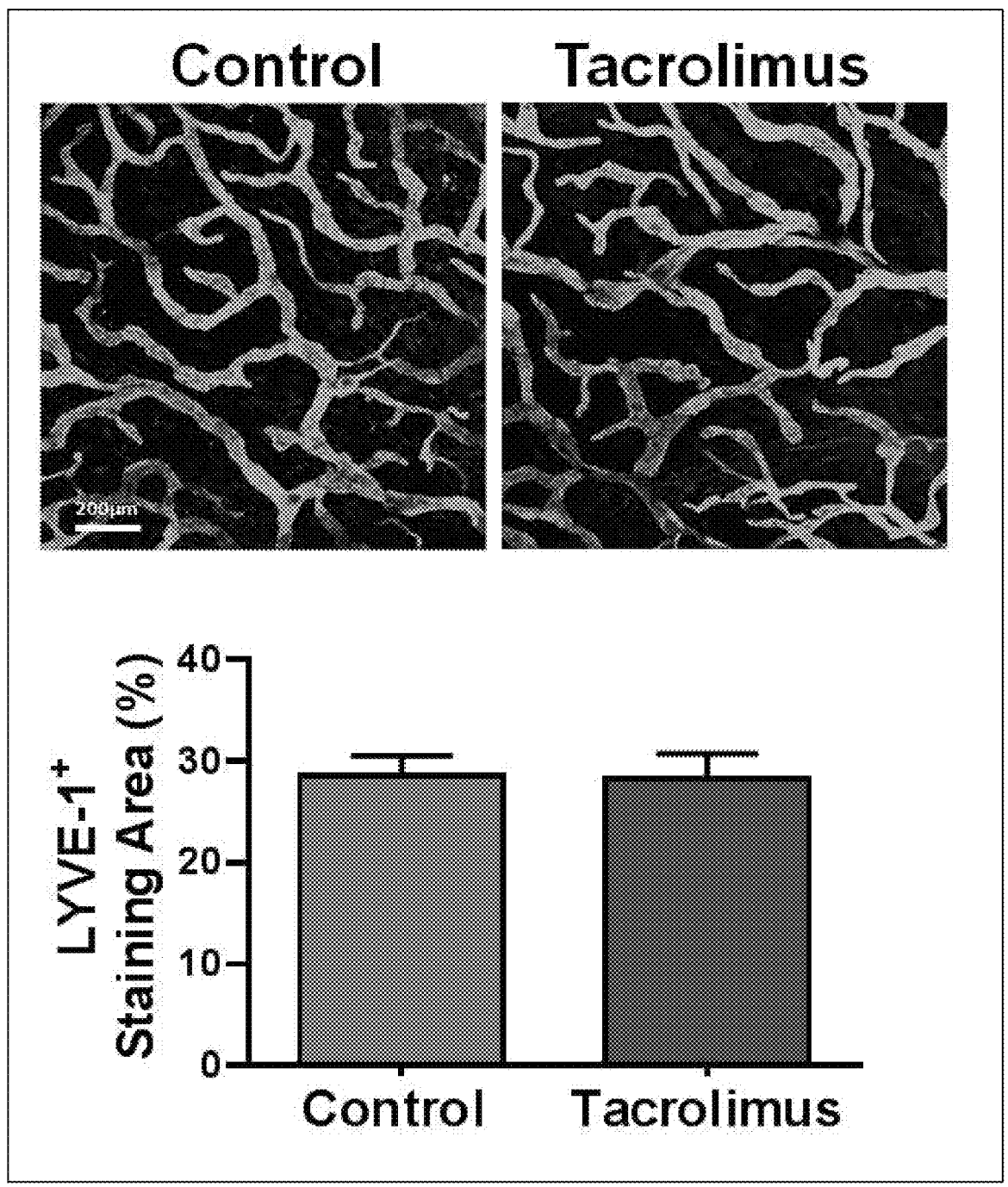
FIG. 16 shows that topical tacrolimus does not increase lymphangiogenesis in the absence of injury/inflammation. Upper panels show representative 5× images of immunofluorescent staining of lymphatic vessels in unwounded mouse ears after 4 weeks of application of topical tacrolimus or vehicle control. Quantification of the LYVE-1$^+$ staining area is shown below.
Figure 17:
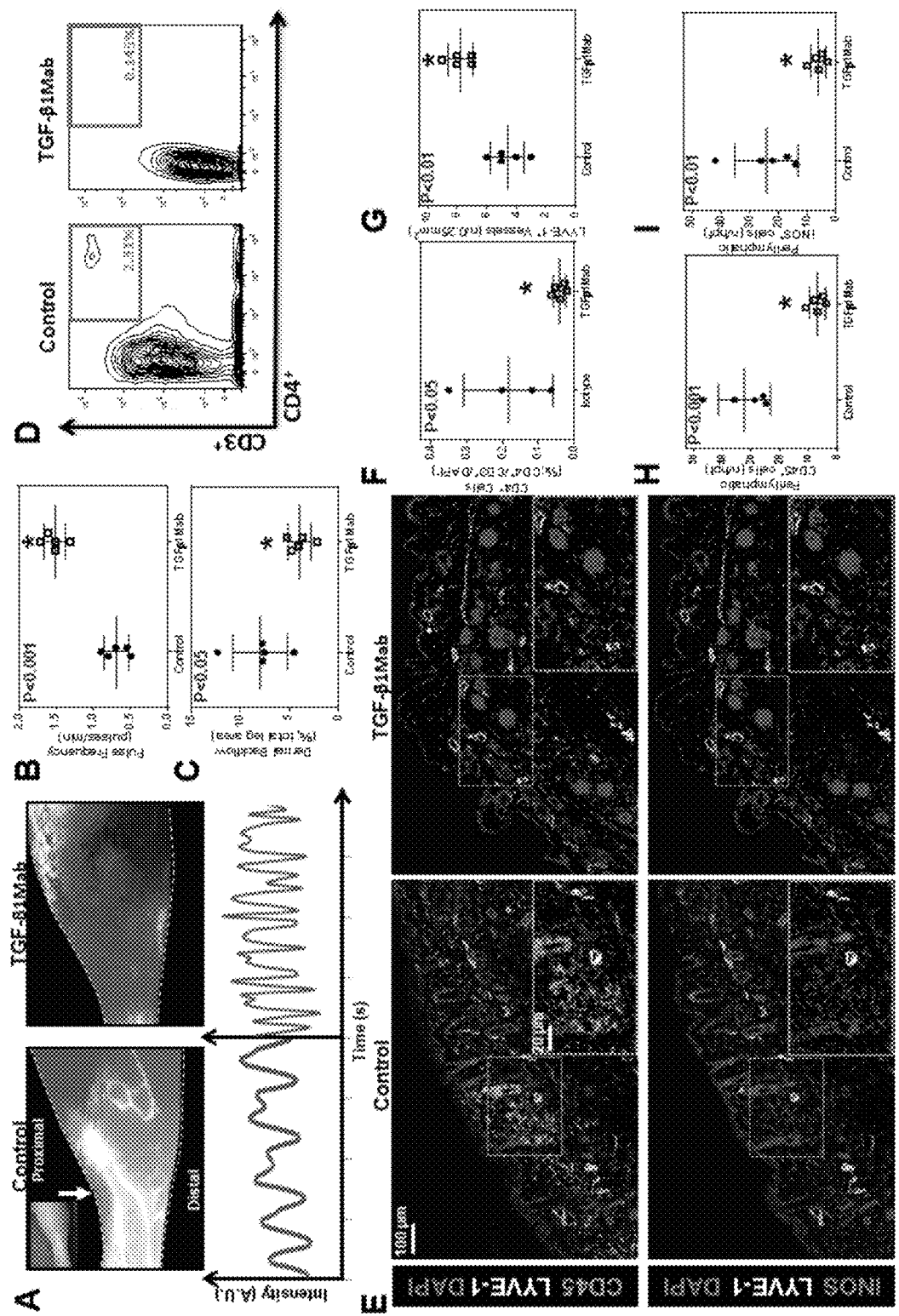
FIG. 17 shows that inhibition of TGF-β improves lymphatic function and decreases perilymphatic accumulation of inflammatory cells after popliteal lymph node dissection. (A) shows a representative photograph of near infrared images of the distal hind limbs of mice treated with isotype control or TGF-β monoclonal antibodies (mAbs) 4 weeks after PLND (upper panel) and pumping frequency in collecting lymphatics (lower panel). Note increased pumping frequency of hind limb collectors in TGF-β mAb treated mice. Also notice dermal back flow (white arrow) in control but not TGF-β mAb treated mice. (B) shows quantification of collecting lymphatic pumping (pulse) frequency in control and TGF-β mAB treated mice. (C) shows quantification of dermal back flow in control and TGF-β mAB treated mice. (D) shows a representative flow cytometry plot from distal hind limb tissues of control and TGF-β mAb treated mice 4 weeks after PLND. Note decreased percentage of CD3+CD4+ cells in TGF-β mAb treated mice. (E) shows representative low and high (inset) power photomicrographs of perilymphatic (LYVE-1+) inflammatory cells (CD45$^+$; top) and iNOS+ (bottom) cells in control and TGF-β mAb treated mice. (F) shows quantification of flow cytometry for CD4+ cells in hind limb tissues in control and TGF-β mAb treated mice. (G) shows quantification of quantification of the number of LYVE-1+ vessels in control and TGF-β mAb treated mice. (H) shows quantification of the number of perilymphatic CD45+ cells in control and TGF-β mAb treated mice. (I) shows quantification of the number of perilymphatic iNOS+ cells in control and TGF-β mAb treated mice.

We also studied lymphangiogenesis during wound healing using an ear punch wound model and applying topical tacrolimus or control ointment for 4 weeks. Similar to the corneal model, we found that topical tacrolimus significantly increased lymphatic vessel density and branching in the ear skin adjacent to the wound as compared with controls (FIG. 6 (D), (F)). To test the possibility of direct lymphangiogenic effects of tacrolimus, we applied tacrolimus to unwounded mouse ears for 4 weeks, and then performed whole mount confocal imaging of lymphatic vessels. We observed no increase in lymphangiogenesis in this uninjured, non-inflamed setting (FIG. 16). Together, these results indicate that tacrolimus facilitates the formation of new lymphatic vessels in the setting of inflammation generally and in the setting of lymphedema/lymphatic injury specifically.

Methods

Study Design

The aim of this study was to test the hypothesis that local inhibition of T cells can both prevent development of lymphedema after lymphatic injury and treat established lymphedema after it has developed. Using two different mouse models of lymphatic injury and lymphedema we analyzed the efficacy of Tacrolimus, an FDA approved topical anti-T cell medication on these outcomes. Having found that Tacrolimus was indeed effective in preventing and treating lymphedema, we then sought to analyze the cellular and molecular mechanisms that regulate this response. In these subsequent studies we tested the hypothesis that inhibition of CD4+ inflammatory responses improved lymphatic function by increasing the formation of collateral lymphatics, decreasing collagen deposition in the extracellular matrix surrounding initial lymphatics, and increasing the pumping frequency of collecting lymphatics. Our studies were all performed using adult female (10-14 week old) C57BL/6J mice (Jackson Laboratories, Bar Harbor, Me.) that were maintained in light- and temperature-controlled pathogen free environments and fed ad libitum. All studies were approved by the Institutional Animal Care and Use Committee (IACUC) at Memorial Sloan Kettering Cancer Center. Each experiment was performed using a minimum of 6-8 animals and assays were performed in triplicate. All cell counts were performed by reviewers blinded to the intervention.

Animal Models and Treatments

Tail surgery and lymphatic ablation was performed as previously published. Clavin et al., *Am. J. Physiol. Heart Circ. Physiol.* 295:H2113-H2127 (2008). Briefly, the superficial and deep collecting lymphatics of the mid portion of the tail were excised using a 2 mm circumferential excision. Tacrolimus 0.1% (Astellas, Tokyo, Japan)/vehicle control (petroleum jelly) was treated topically beginning at 2 weeks after surgery (early treatment) and beginning at 6 weeks after surgery (late treatment) in different set of animals. For both approaches we treated the animals with 0.1% tacrolimus or vehicle control, twice daily for 4 week period (for early treatment) and 3 week period (late treatment). Tacrolimus (approx. 0.05 g) was applied as a thin layer to the entire tail area. To enable analysis of the lymphatic collecting vessel pumping capacity we utilized a previously described mouse popliteal lymphadenectomy model. Blum et al., *Breast Cancer Res Treat* 139:81-86 (2013); Sharma et al., *Am. J. Physiol. Heart Circ. Physiol.* 292:H3109-H3118 (2007). Briefly, the hind limb collecting vessels and popliteal lymph nodes were identified and the lymph nodes were excised with the popliteal fat pad. Beginning 2 weeks after surgery, animals were randomized to treatment with either 0.1% topical tacrolimus or vehicle control (petroleum jelly) twice daily for 2 weeks.

A corneal lymphangiogenesis assay was performed as previously reported. Cursiefen et al., *Cornea* 25:443-447 (2006). Briefly, 10-0 nylon sutures (Ethicon, Cincinnati, Ohio) were placed in the cornea at 120° angles. Beginning immediately after suture placement, animals were treated with systemic tacrolimus or vehicle control daily for two weeks, followed by analysis using confocal microscopy (Leica Microsystems, Weitziar, Germany). Systemic tacrolimus (Biotang Inc., Lexington, Mass.) was dissolved in 10% ethanol with 1% tween 80 in PBS (Rozkalne et al., *Neurobiol. Dis.* 41:650-654 (2011); Butcher et al., *J. Neurosci.* 17:6939-6946 (1997)) and dosed at 4 mg kg$^{-1}$ IP daily. Vehicle control for systemic tacrolimus was the equivalent volume of 10% ethanol, 1% tween 80 in PBS. Cutaneous lymphangiogenesis was assessed using an ear punch wound model as previously reported. Cho et al., *Proc. Nat. Acad. Sci. USA* 103:4946-4951 (2006). Following wounding, ear skin was treated either with topical tacrolimus or vehicle control for 4 weeks. Ears were then harvested and fixed in 1% PFA overnight. The anterior and posterior portions of the ear skin were then divided removing the cartilage and whole mount staining for LYVE-1 and CD31 was performed. Tile-scan images were obtained using a confocal microscope (Leica Microsystems, Weitziar, Germany) and skin within 400 μm of the wound edge was analyzed using Metamorph software (Molecular Devices, Sunnyvale, Calif.). Standardized (200 μm×200 μm) fields were analyzed for the number of branch points present per unit area by two blinded reviewers.

Flow Cytometry

Flow cytometry was performed on peripheral blood samples as previously reported. Zampell et al., *PLoS ONE* 7:e49940 (2012). Briefly, erythrocytes were lysed with RBC lysis buffer (Ebioscience, San Diego, Calif.) followed by staining with fluorophore-conjugated antibodies (CD45, CD3, and CD4; all from Biolegend, San Diego, Calif.) and analysis with a FACSCalibur flow cytometer (BD Biosciences, Franklin Lakes, N.J.) using FlowJo software (Tree Star, Ashland, Oreg.).

Tacrolimus Blood Level by Mass Spectrometry

Blood levels of tacrolimus were measured using mass spectrometry in a modification of a previously reported method. Donaldson et al., *Meth. Mol. Biol.* 603:479-487 (2010). Briefly, whole blood was collected in sodium EDTA-coated tubes (Terumo, Shibuya, Japan) and then analyzed using a Thermo Scientific Aria TLX-2 turbulent flow chromatograph (TFC) coupled to a TSQ Quantum Ultra triple quadrupole mass spectrometer (Thermo Scientific, Franklin, Mass.). The TurboFlow column used was a Cyclone P-50× 0.5 mm while the analytical column was a Hypersil Gold C-18 column, 3×50 mm. To whole blood (50 μL) was added 200 μL of 0.2 mM ZnSO4 containing ascomycin as an internal standard. Following a 30 minute incubation and centrifugation, 50 μL of the supernatant was injected into the TFC system. The analytes were eluted through the column (0.75 mL min$^{-1}$) with a gradient of water and methanol solutions containing 10 mM ammonium formate and 0.1% formic acid. The analytical run time was 4.5 minutes. The between-day imprecision of the assay was determined at three concentrations over a period of 10 days. At concentrations of 3.3, 12.6 and 31.9 ng mL-1 the coefficients of variation were of 9.8, 7.0 and 7.8%, respectively. The assay has a linear range from 0 to 40 ng mL$^{-1}$.

Analysis of Lymphatic Function

Tail volumes were calculated using the truncated cone formula as previously reported (Clavin et al., *Am. J. Physiol. Heart Circ. Physiol.* 295:H2113-H2127 (2008)) and confirmed using histological measurements of soft tissue thickness of the skin/subcutaneous tissues in a standardized manner using Mirax Imaging Software (Carl Zeiss, Munich, Germany).

Lymphoscintigraphy was performed using our previously published methods. Avraham et al., *Am. J. Pathol.* 177:3202-3214 (2010). Briefly, 50 μl of filtered technetium-99m ($^{99m}$Tc) sulfur colloid (Nuclear Diagnostic Products, Rockaway, N.J.) was injected in the distal tail. Images were taken using an X-SPECT camera (Gamma Medica, Northridge, Calif.) and region-of-interest analysis was performed to derive decay-adjusted counts in the sacral lymph nodes and to calculate peak and rate of nodal uptake using ASIPro software (CTI Molecular Imaging, Knoxville, Tenn.).

Near infrared imaging (NR) was performed using a modification of previously published results. Tassenoy et al., *Lymphat. Res. Biol.* 7:145-151 (2009). Briefly, 15 μl (0.15 mg mL$^{-1}$) indocyanine green (ICG, Sigma-Aldrich, Saint Louis, Mo.) was injected intradermally in the web space of the dorsal hind limb and visualized using an EVOS EMCCD camera (Life Technologies, Carlsbad, Calif.) with a LED light source (CoolLED, Andover, United Kingdom). Static/video images were obtained using a Zeiss V12 Stereolumar microscope (Caliper Life Sciences, Hopkinton, Mass.) and lymphatic pumping function was analyzed using Fiji software (NIH, Bethesda, Md.) by identifying a region-of-interest over the dominant collecting vessel of the leg and subtracting the background fluorescent intensity plotted over time.

Histology and Immunostaining

Immunohistochemical staining was performed using our published methods. Clavin et al., *Am. J. Physiol. Heart Circ. Physiol.* 295:H2113-H2127 (2008). Briefly, tissues were fixed in 4% paraformaldehyde at 4° C., decalcified in 5% sodium EDTA (Santa Cruz Biotechnology, Dallas, Tex.), embedded in paraffin, and sectioned at 5 micrometers. Cut sections were rehydrated and heat-mediated antigen unmasking was performed using 90° C. sodium citrate (Sigma-Aldrich). Non-specific binding was blocked with 2% BSA/20% animal serum. Tissues were incubated overnight with primary antibody at 4° C. Primary antibodies used for immunohistochemical stains included goat anti-mouse LYVE-1, rat anti-mouse CD45, rabbit anti-mouse CD4, and rat anti-mouse F4/80 (all from R&D, Minneapolis, Minn.), rabbit anti-mouse CD3 (from Dako, Carpinteria, Calif.), Cy3-conjugated mouse anti-αSMA (from Sigma-Aldrich), rabbit anti-human IFN-γ, rabbit anti-mouse TGF-β1, rabbit anti-mouse p-SMAD3, rabbit anti-mouse collagen I, rabbit-anti-mouse iNOS, and hamster-anti-mouse podoplanin, rabbit anti-mouse HMGB-1 and HSP-70 (all from ABCAM, Cambridge, Mass.).

Immunofluorescence staining was performed using AlexaFluor fluorophore-conjugated secondary antibodies (Life Technologies, Norwalk, Conn.). Images were scanned using Mirax imaging software (Carl Zeiss). Peri-lymphatic CD45$^+$ and CD4$^+$ cell counts were assessed by counting positively stained cells within 50 μm of the most inflamed lymphatic vessel in each quadrant of the leg. Positively stained cells were counted by two blinded reviewers in four randomly-selected, 40× high-power fields in a minimum of 4 fields per animal. Collagen I deposition was quantified using Metamorph software (Molecular Devices, Sunnyvale, Calif.) in dermal areas of 5 μm cross-sections. This analysis was confirmed using picrosirius red staining and scar index calculation as previously reported. Flanders et al., *Am. J. Pathol.* 163:2247-2257 (2003). Bridging lymphatic vessels in mouse tails were counted in the re-epithelialized surgical site in 4 different high-power fields per tail.

Sirius Red Staining

Paraffin sections of tail tissues were stained with picrosirius red staining kit (Polysciences, Warrington, Pa.) according to the manufacturer's instructions. Images were obtained through polarized light on an Axiocam 2 microscope (Carl Zeiss) and the scar index was quantified with Metamorph software by calculating the ratio of red-orange:green-yellow fibers with higher numbers representing increased scarring.

Real-Time PCR

RNA extraction was performed on tail skin using TRIZOL (Invitrogen, Life Technologies, Carlsbad, Calif.) according the manufacturer's recommendations. RNA quality and quantity was assessed using an Agilent bio analyzer (Agilent Technologies, Inc; Santa Clara, Calif.). The isolated RNA was converted to cDNA using a TaqMan reverse transcriptase kit (Roche, Branchburg, N.J.) and relative expression of gene expression between groups was performed using delta-delta CT PCR analysis and normalizing gene expression using GAPDH RNA amplification as previously described. Schmittgen et al., *Nat. Protoc.* 3:1101-1108 (2008). Relative expression was calculated using the formula: $2[-(Ct\ gene\ of\ interest-Ct\ endogenous\ control)\ sample\ A-(Ct\ gene\ of\ interest-Ct\ endogenous\ control)\ sample\ B)]$. All samples were performed in triplicate. The primers used for the PCR targets of interest were for VEGF-C, TGF-β1, and IFN-γ (Applied Biosystems, Life Technologies, Carlsbad, Calif.).

In-Vivo Detection of ROS and Miles Assay for Vascular Permeability

In-vivo detection of ROS was performed by bioluminescent imaging of NADPH oxidase as described by Han et al. (*J. Vis. Exp.* doi: 10.3791/3925 (2012)). Briefly, mice were systemically injected with L-012 (an analogue of luminol) (20 μg/g) dissolved in PBS at different time points after PLND and luminescent signals representing ROS at the PLND surgery site were imaged and quantified using IVIS spectrum 200 (Xenogen Corporation). Miles assay for vascular permeability was performed as described. Radu et al., *J. Vis. Exp.* doi: 10.3791/50062 (2013). Briefly, 200 μl of 0.5% sterile Evans blue was injected via tail vein to 2 weeks tacrolimus treated PLND mice. After 30 min PLND hind limbs were imaged to observe Evans blue leakage. Hind limbs were excised and incubated in formamide for 48 hrs. at 55° C. to extract the Evans blue. Extracted Evans blue was quantified by measuring absorbance at 610 nm.

Statistical Analysis

Data was analyzed and displayed using GraphPad Prism software (GraphPad Software, La Jolla, Calif.). Values are presented as mean±standard deviation unless otherwise noted. Statistical significance was set at p≤0.05, and differences between 2 groups was assessed with the Student's t-Test while multiple analyses were performed using ANOVA with post hoc tests to compare within groups.

Conclusions

Because $CD4^+$ T cells play a critical role in lymphedema pathology, the purpose of this study was to evaluate the efficacy of topical tacrolimus for the prevention and treatment of lymphedema. We used well a described mouse tail model of lymphedema as well as a previously described model of lymphatic injury resulting from popliteal lymph node dissection (PLND) to show that topical tacrolimus potently prevents development of lymphedema after lymphatic injury by decreasing chronic inflammatory responses, decreasing tissue and lymphatic fibrosis, increasing collecting lymphatic pumping, and increasing collateral lymphatic vessel formation. These findings have important implications for the treatment of lymphedema since previous experimental attempts have focused primarily on increasing lymphatic regeneration using exogenous lymphangiogenic growth factors.

We also found that tacrolimus potently decreases dermal and subcutaneous T cell infiltration and tissue fibrosis after lymphatic injury. These changes prevent development of lymphedema and can reverse pathologic changes once lymphedema is established. Treatment with tacrolimus increases lymphatic function by increasing formation of collateral lymphatics and by increasing collecting lymphatic pumping frequency. To our knowledge, this is the first targeted topical pharmacologic means of preventing and treating post-surgical lymphedema.

We found that tacrolimus was more effective when applied earlier, immediately after surgery, likely reflecting the fact that this treatment did not require reversal of established pathology. This finding is consistent with previous studies in other fibroproliferative disorders such as hepatic fibrosis in which prevention is much more effective than reversal of histological changes. Friedman et al., *Hepatology* 43:S82-S88 (2006).

Example 2. Treatment and Prevention of Lymphedema Using Pirfenidone

Pirfenidone Decreases Tail Lymphedema

Figure 19:
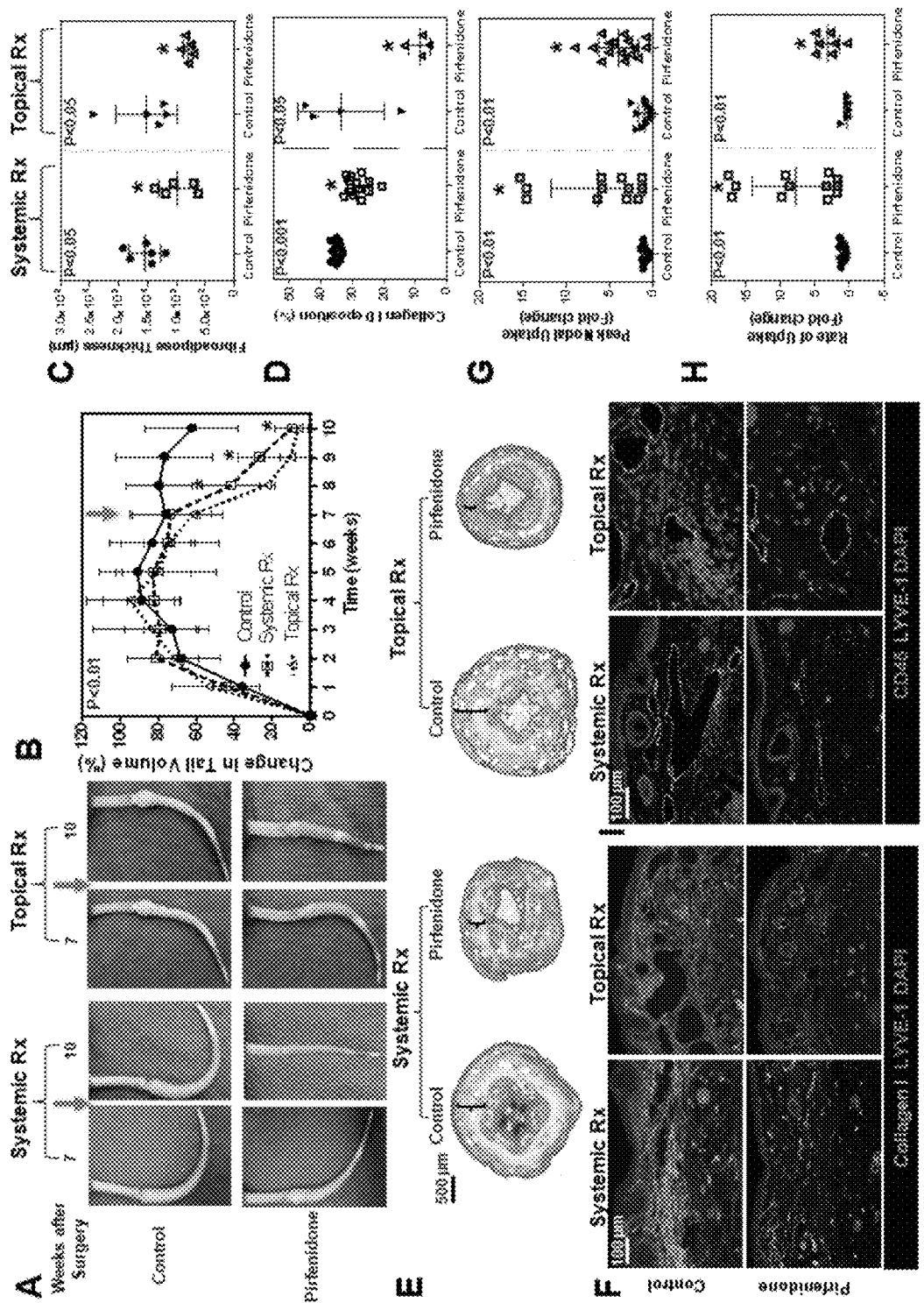
FIG. 19 shows that systemic and topical pirfenidone decrease mouse tail lymphedema and inflammation. (A) shows representative photographs of mouse tails after systemic and topical treatment with pirfenidone or vehicle control. Treatment was started 7 weeks after tail lymphatic injury. Note marked improvement in pirfenidone treated mice. (B) shows quantification of mouse tail volumes in control, topical pirfenidone, and systemic pirfenidone treated mice. Note significant reductions in pirfenidone treated mice (arrow shows when pirfenidone treatment was started). (C) shows quantification of fibroadipose tissue deposition in control and pirfenidone treated mice. (D) shows quantification of type I collagen deposition in control and pirfenidone treated mice. (E) shows representative cross-sectional photomicrographs of mouse tails treated with control or pirfenidone (systemic or topical). (F) shows representative high-power photomicrographs of tail cross sections stained for type I collagen and lymphatic vessels (LYVE-1). Note decreased type I collagen deposition in pirfenidone treated mice. (G) shows peak nodal uptake of $^{99}$Tc after distal tail injection of sulfur colloid conjugated $^{99}$Tc. Note increased uptake in sacral lymph nodes in pirfenidone treated ice. (H) shows the rate of lymph node uptake of $^{99}$Tc after distal tail injection. Note more rapid uptake in pirfenidone treated mice. (I) shows Representative high-power photomicrographs of tail cross sections stained for leukocytes (CD45$^+$) and lymphatic vessels (LYVE-1). Note decreased perilymphatic CD45$^+$ cell accumulation in pirfenidone treated mice.

Disruption of the superficial and deep lymphatics of the mouse tail resulted in almost 80% increase in tail volumes 2 weeks after surgery (FIG. 19 (A), (B)). We have previously shown that swelling at this time point is due primarily to accumulation of interstitial fluid. Avraham et al., *FASEB J.* 27:1114-1126 (2013). Chronic lymphatic obstruction in the tail results in gradual replacement of interstitial fluid by fibroadipose tissues and accumulation of inflammatory cells over the ensuing 4 weeks. Avraham et al., *FASEB J.* 27:1114-1126 (2013). These pathologic changes closely mirror clinical lymphedema and persist for at least 8-10 additional weeks once lymphedema is established. Based on this knowledge, we waited 7 weeks after surgery for lymphedema to become established and then initiated treatment with pirfenidone with an intent to treat these established soft tissue changes. We initially started with systemic treatment as most of the previous studies on pirfenidone use this route of administration for the treatment of fibrotic diseases. However, once we established pirfenidone as an effective treatment, we developed a topical formulation, as local administration would be preferred as to minimize any potential side effects due to systemic therapy. Treatment with both systemic and topical pirfenidone markedly decreased gross tail swelling, tail volume, and soft tissue thickness as compared with controls (FIG. 19 (A)-(E); p<0.01 for tail volume and p<0.05 for thickness for both treatment groups).

Pirfenidone Increases Lymphatic Function in the Tail

Given the efficacy of pirfenidone in treating lymphedema in the tail model, we next sought to study if pirfenidone regulates lymphatic function after lymphatic injury. Using $^{99}$Tc lymphoscintigraphy, a technique in which a radiotracer is injected in the distal tail, we measured its uptake by the sacral lymph nodes over 90 minutes. Decay-adjusted uptake of the sacral lymph nodes in both systemic and topical pirfenidone treated animals demonstrated an almost 4-fold increase in $^{99}$Tc uptake in pirfenidone-treated animals as compared with controls. In addition, both systemic and topically treated animals demonstrated an almost 4-fold increase in peak nodal uptake (FIG. 19 (G); p<0.01 for both). Similarly, there was an increased in the rate of uptake in both systemic and topically treated animals as indicated by the increased slope of the decay-adjusted curve (FIG. 19 (H); p<0.01 and p<0.05, respectively).

Figure 20:
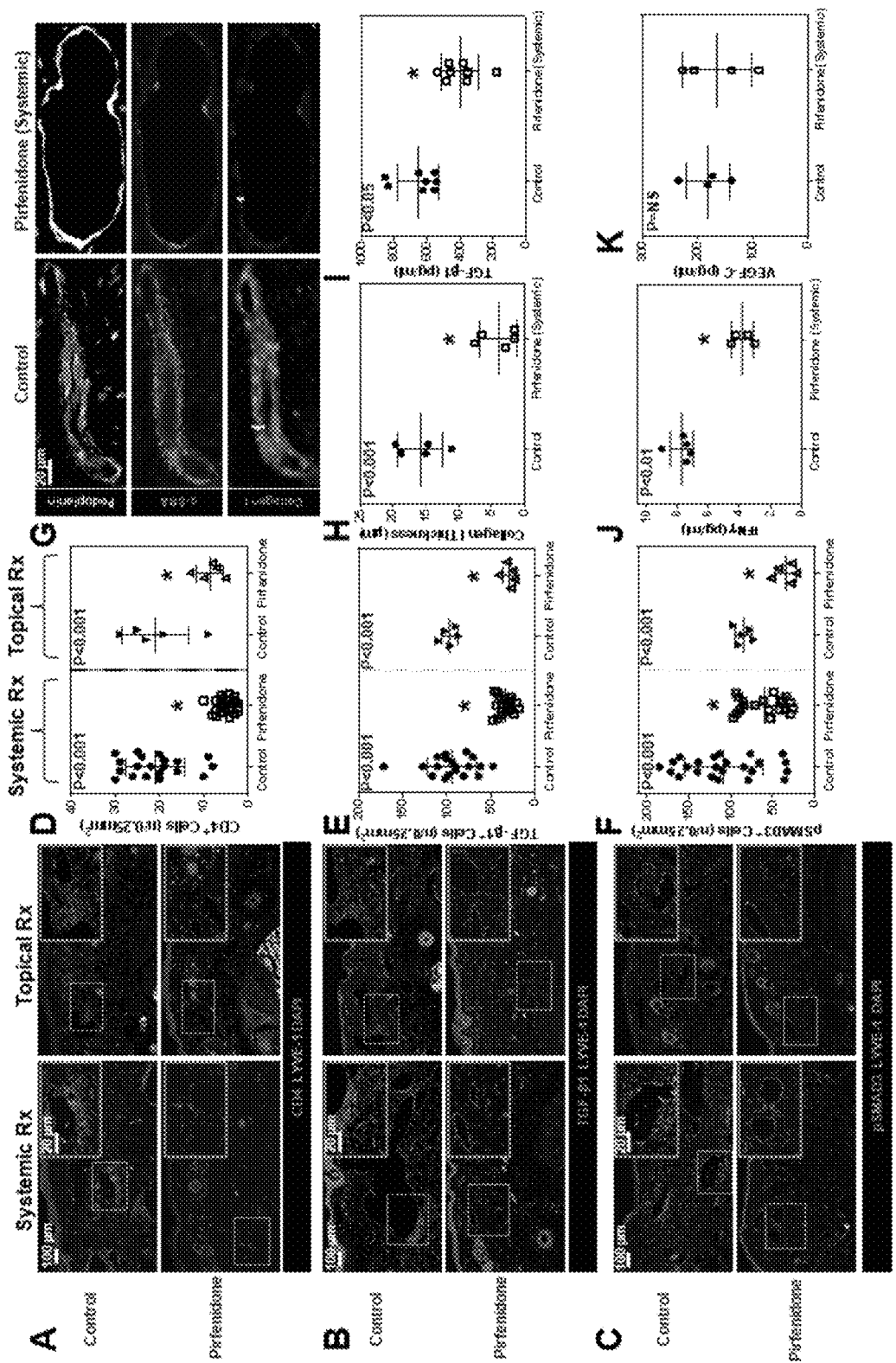
FIG. 20 shows that pirfenidone decreases perilymphatic inflammation and TGF-β expression. (A) shows representative photomicrographs of hind limb sections demonstrating perilymphatic accumulation of CD4+ cells in control and pirfenidone-treated animals (systemic treatment shown in left panels; topical treatment shown in right panels). High power images are shown in the inset. (B) shows representative photomicrographs of hind limb sections demonstrating perilymphatic accumulation of TGF-β1+ cells in control and pirfenidone-treated animals (systemic treatment shown in left panels; topical treatment shown in right panels). (C) shows representative photomicrographs of hind limb sections demonstrating perilymphatic accumulation of SMAD3+ cells in control and pirfenidone-treated animals (systemic treatment shown in left panels; topical treatment shown in right panels). (D) shows quantification of perilymphatic CD4+ cells in control and pirfenidone-treated mice. (E) shows quantification of perilymphatic TGF-β1+ cells in control and pirfenidone-treated mice. (F) shows quantification of perilymphatic SMAD3+ cells in control and pirfenidone-treated mice. (G) shows a high-powered photomicrograph of hind limb collecting vessel from control and pirfenidone treated mice stained for podoplanin, α-SMA, and type I collagen. Note thickening and proliferation of α-SMA+ cells in control mice. (H) shows quantification of type I collagen deposition around collecting lymphatics of control and pirfenidone treated mice. (I) shows serum TGF-β1 expression in control and systemic pirfenidone treated mice. (J) shows serum IFN-γ expression in control and systemic pirfenidone treated mice. (K) shows serum VEGF-C expression in control and systemic pirfenidone treated mice.

Pirfenidone Decreases Inflammation and Fibrosis in the Tail After Lymphatic Injury Chronic inflammation is a histological hallmark of clinical lymphedema and is characterized by increased accumulation of inflammatory cells, specifically T-helper cells. Avraham et al., *FASEB J* 27:1114-1126 (2013); Zampell et al., *PLoS ONE* 7:e49940 (2012); Ghanta et al., *Am. J. Physiol. Heart Circ. Physiol.* 308:H1065-1077 (2015); Olszewski et al., *Lymphology* 23:23-33 (1990). Consistent with this, we found that both systemic and topically treated animals had markedly decreased numbers of leukocytes infiltrating the dermis and subcutaneous fat as compared with controls. Inflammatory cells in lymphedematous tissues harvested from control animals were located in close proximity to the capillary and collecting lymphatics, but were virtually absent in pirfenidone treated mice. Similarly, we noted marked decreases in the numbers of infiltrating CD3$^+$ cells, and CD4$^+$ cells (FIG. 20 (A), (D); p<0.001 for both). Furthermore, we noted a significant decrease in accumulation of IFN-$\gamma$ protein, a T-helper (Th) 1 cell produced cytokine that has previously been found to be potently anti-lymphangiogenic (FIG. 20 (J); p<0.01). Kataru et al., *Immunity* 34:96-107 (2011); Shao et al., *J. Interferon Cytokine Res.* 26:568-574 (2006).

In addition, we have previously shown macrophages to accumulate in tissues distal to lymphatic injury. Zampell et al., *PLoS ONE* 7:e49940 (2012). We analyzed the effect of pirfenidone on macrophage infiltration since they regulate both fibrosis (primarily through TGF-$\beta$1) and regulate lymphangiogenesis (via VEGF-C). We found no difference in F4/80 cellular infiltration in lymphedematous tail tissues with pirfenidone treatment, both systemic and topical, compared to controls. Consistent with this, we found no difference in VEGF-C protein accumulation after treatment with pirfenidone (FIG. 20 (K); p=NS). Taken together, these findings show that following lymphatic injury, inflammatory cells, specifically T cells, accumulate in large numbers in close proximity to skin/subcutaneous lymphatic vessels and that this response is mitigated by systemic and topical pirfenidone treatment.

Patients with lymphedema have progressive soft tissue fibrosis and the degree of fibrosis correlates with the severity of disease clinically. Tassenoy et al., *Lymphat. Res. Biol.* 7:145-151 (2009). Consistent with other fibrotic disorders, we have previously shown TGF-$\beta$1 to be a critical pro-fibrotic growth factor in lymphedema. Avraham et al., *Am. J. Pathol.* 177:3202-3214 (2010). In addition, we have shown TGF-$\beta$1 to have direct anti-lymphangiogenic effect on LECs. Clavin et al., *Am. J. Physiol. Heart Circ. Physiol.* 295:H2113-H2127 (2008). Therefore, we analyzed infiltration of TGF-$\beta$1$^+$ cells and cellular expression of its activated downstream signaling molecule, pSMAD3. In both systemic and topical pirfenidone treatment groups we found markedly decreased accumulation of both TGF-$\beta$1$^+$ cells and pSMAD3$^+$ cells as compared to controls (FIG. 20 (B), (C), (E), (F); p<0.001 for all). Consistent with this, we found decreased accumulation of TGF-$\beta$1 protein accumulation after treatment with pirfenidone (FIG. 20 (I); p<0.05). This correlated with significantly decreased dermal and subcutaneous type I collagen deposition in both treatment groups as compared with control mice (FIG. 19 (D), (F); p<0.001 for systemic and p<0.05 for topical).

Since structural changes in collecting lymphatic vessels (hypertrophy of smooth muscle, thick layers of type I collagen, constriction of the lumen) have been described in human patients with lymphedema, we examined the collecting lymphatic vessels of our animals for similar changes. Mihara et al., *PLoS One* 7:e41126 (2012). Consistent with these human studies, collecting lymphatics ($\alpha$-SMA$^+$/podoplanin$^+$) of control mice were surrounded by thick layers of type I collagen while pirfenidone-treated animals had essentially normal lymphatic vessels (FIG. 20 (H)).

Pirfenidone Increases Lymphatic Function in the Hind Limb

Figure 18:
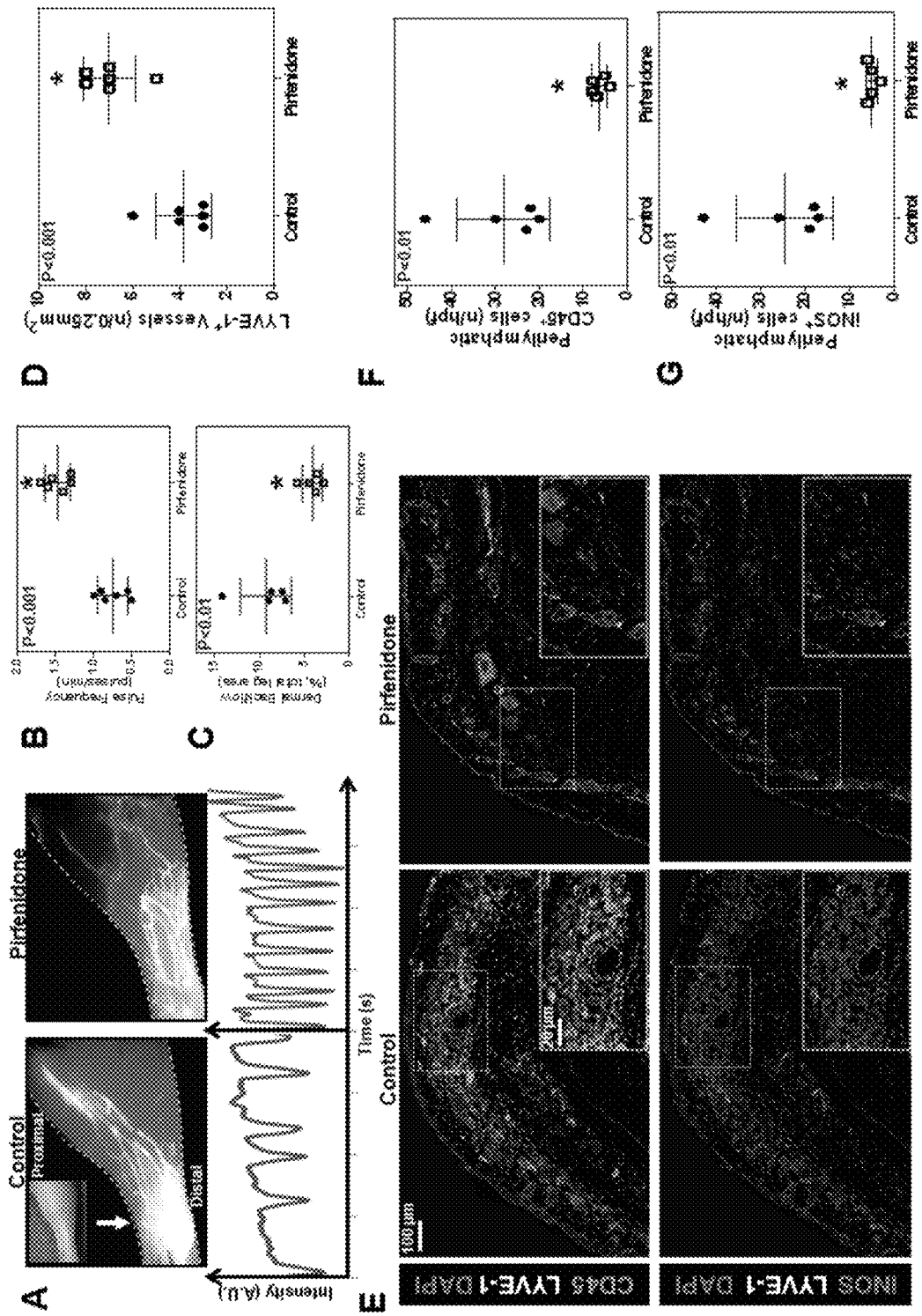
FIG. 18 shows that systemic pirfenidone improves lymphatic function in the hind limb after surgical lymphatic injury. (A) (upper panels) shows representative NIR images of hind limbs obtained 50 minutes after distal foot injection of ICG in mice treated with or without pirfenidone 4 weeks after PLND. White arrows show dermal backflow of ICG. Inset photograph is for orientation. Lower panels show graphical representations of lymphatic vessel pulsations in hind limb collecting vessels of mice treated with or without pirfenidone 4 weeks after PLND. (B) shows quantification of pulsation frequency (pulses/minute) to the right (n=6 animals/group; *p<0.05). (C) shows quantification of dermal backflow in control and pirfenidone treated mice. (D) shows quantification of LYVE-1$^+$ vessels/0.25 mm$^2$ area in distal hind limb tissues of control or pirfenidone-treated animals harvested 4 weeks after PLND (n=6 animals/group; *p<0.001 for LYVE-1). (E) shows representative low and high (inset) power fluorescent co-localization images of inflammatory cells (CD45$^+$; upper panels), iNOS$^+$ cells (lower panels) and lymphatic vessels (LYVE-1$^+$) in tissues harvested from the distal hind limbs of animals treated with or without pirfenidone 4 weeks after PLND, scale bar=100 µm. Higher-power (80×) images are shown in the lower right corner inset of each figure, scale bar=20 µm. Note perilymphatic accumulation of CD45$^+$ and iNOS$^+$ cells. (F) shows quantification of peril-lymphatic CD45$^+$ cells in control and pirfenidone treated mice. (G) shows quantification of perilymphatic iNOS$^+$ cells/hpf in control and pirfenidone-treated mice.

In order to understand the mechanisms by which pirfenidone increases lymphatic function, we analyzed dermal backflow in initial lymphatics and collecting lymphatic pumping capacity using a mouse hind limb PLND model. Blum et al., *Breast Cancer Res. Treat.* 139:81-86 (2013). Using NIR lymphangiography 4 weeks after PLND, we found that animals treated with 2 weeks of systemic pirfenidone had markedly less dermal backflow and capillary vessel leakage as compared with vehicle-treated controls (FIG. 18 (A), white arrow). In addition, pirfenidone-treated animals had significantly increased rate of collecting lymphatic vessel contraction as compared with controls (2-fold increase; FIG. 18 (A), (B); p<0.0015). This response, similar to our findings with the tail model, correlated with a significant decrease in perilymphatic infiltration of inflammatory cells in mice treated with pirfenidone (FIG. 18 (E) (upper panels), FIG. 18 (F); p<0.01). In addition, treatment with pirfenidone resulted in a significant decrease in peri-lymphatic expression of iNOS by inflammatory cells (FIG. 18 (E) (lower panels), FIG. 18 (G); p<0.01). This is a critical finding as increased peri-lymphatic iNOS accumulation, in the setting of inflammation, has been shown to disrupt normal nitric oxide gradients that are critical for normal, coordinated lymphatic vessel contractility. Liao et al., *Proc. Natl. Acad. Sci. USA* 108:18784-18789 (2011). This provides an important mechanism as to how pirfenidone improves lymphatic vessel contractility.

Pirfenidone Increases Collateral Lymphatic Vessel Formation

Since T cells, specifically Th1 and Th2 cytokines, are known to potently inhibit lymph node lymphangiogenesis and inflammatory lymphangiogenesis during wound repair, we next sought to determine if treatment with pirfenidone increases the formation of collateral lymphatics. Kataru et al., *Immunity* 34:96-107 (2011); Clavin et al., *Am. J. Physiol. Heart Circ. Physiol.* 295:H2113-H2127 (2008); Zampell et al., *Am. J. Physiol. Cell Physiol.* 302:C392-C404 (2012); Savetsky et al., *PLoS One* 10:e0126908 (2015). Indeed, histological analysis and identification of lymphatics using LYVE-1 immunofluorescent staining demonstrated a marked increase in lymphatic vessels density in both the tail and hind limb (FIG. 18 (D), (E); p<0.001). This lymphangiogenic response appeared to be independent of VEGF-C expression since we noted no differences in VEGF-C protein analysis in pirfenidone-treated lymphedematous tails as compared to controls whereas there was a profound decrease in anti-lymphangiogenic T cell cytokines such as IFN-$\gamma$ and TGF-1 (FIG. 20 (E), (I), (K); p<0.05 for TGF-$\beta$1, p<0.01 for IFN-$\gamma$, and p=NS for VEGF-C).

Figure 21:
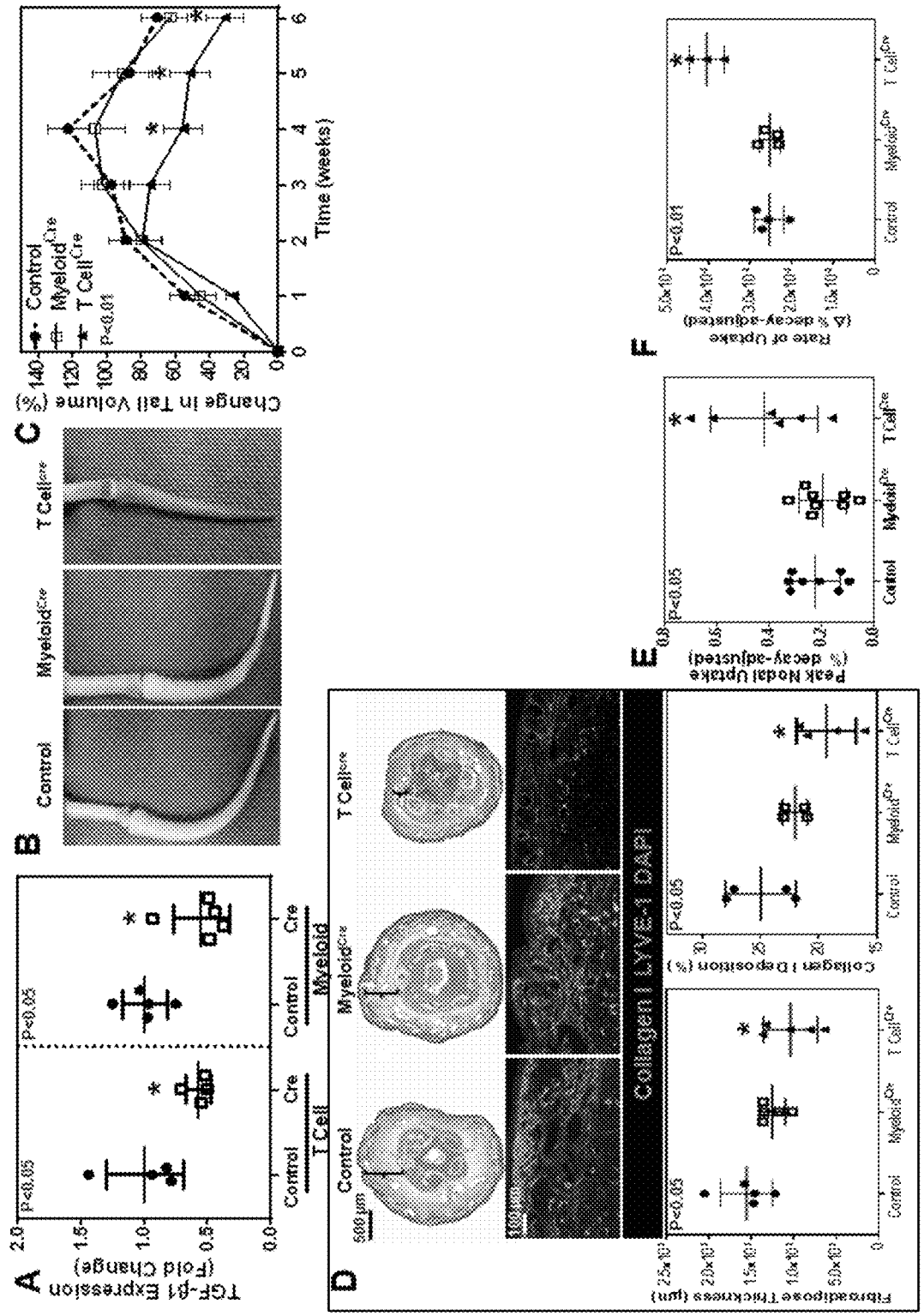
FIG. 21 shows that loss of T cell but not myeloid cell TGF-β expression prevents development of lymphedema after lymphatic injury. (A) shows relative expression of TGF-β1 mRNA in tail tissues harvested from control, T cell"and myeloid" animals 6 weeks following tail lymphatic injury. (B) shows representative photomicrographs of control, myeloid-TGF-β1$^{cre}$, and T cell-TGF-β1$^{cre}$ mice. Note lack of swelling in T cell$^{cre}$ mice. (C) shows quantification of mouse tail volumes in various groups. Note decreased tail volumes in T cell$^{cre}$ mice as compared to wild-type controls. (D) shows representative photomicrographs of tail cross sections stained for H&E (top), type I collagen/LYVE-1 (middle) and quantification of fibroadipose tissue deposition and Type I collagen expression (lower) in various groups. Note decreased fibroadipose tissue deposition in T cell$^{cre}$ mice. (E) shows peak nodal uptake of $^{99}$Tc injected in the distal tail. Note increased uptake in T cell$^{cre}$ mice. (F) shows rate of sacral nodal uptake of $^{99}$Tc in various groups. Note more rapid uptake in T cell$^{cre}$ mice.

TGF-β1 Immunotherapy with Pirfenidone does not Further Improve Lymphatic Function Given that the major mechanism of action of pirfenidone is blockade of TGF-β1 activity, we compared the effect of pirfenidone treatment with TGF-β1 immunotherapy after PLND in separate studies. Schaefer et al., *Eur. Respir. Rev.* 20:85-97 (2011). Using NIR imaging, compared to isotype controls, we found that TGF-β1 immunotherapy alone as well as the combination of TGF-β1 immunotherapy and pirfenidone had decreased dermal backflow, and significantly increased rate of collecting lymphatic vessel contraction. More importantly, there was no added benefit with combination therapy compared to immunotherapy alone, indicating that we were maximally inhibiting TGF-β1 at the doses we utilized (FIG. 21 (A)-(C); p=NS). Similarly, using flow cytometry, compared to isotype controls, we found that TGF-β1 immunotherapy alone as well as the combination of TGF-β1 immunotherapy and pirfenidone had significantly decreased tissue accumulation of T-helper cells distal to the lymphatic injury whereas there was no additional with combination therapy compared to immunotherapy alone.

TGF-β1 KO from T Cells Decreases Tail Lymphedema, Improves Lymphatic Function and Decreases Inflammation and Fibrosis in the Tail after Lymphatic Injury To determine the cellular source of TGF-β1 in the setting of lymphedema, we developed transgenic mice with selective KO of TGF-β1 production from T cells and myelocytes. Phenotypic confirmation of these transgenic mice was confirmed using polymerase chain reaction (PCR) that showed significant decreased TGF-β1 expression from isolated T and myeloid cells from T Cell$^{cre}$ and Myeloid$^{cre}$ mice, respectively, as compared to control mice (FIG. 21 (A); p<0.05 for both). Tail surgeries were performed and analysis was performed 6 weeks after surgery. T Cell$^{cre}$ mice had markedly decreased gross tail swelling, tail volume, and fibroadipose thickness as compared to Myeloidre and control mice (FIG. 21 (B)-(D); p<0.01 for tail volume and p<0.05 for thickness). Analysis of $^{99}$Tc lymphoscintigraphy demonstrated an almost 4-fold increase in decay-adjusted uptake of the tracer in the sacral lymph nodes of T Cell$^{cre}$ mice as compared to Myeloidre and control mice. Similarly, there was an increase in peak nodal uptake as well as the rate of tracer uptake in the T Cell$^{cre}$ mice as compared to Myeloid$^{cre}$ and control mice (FIG. 21 (E), (F); p<0.05 and p<0.01, respectively).

Figure 22:
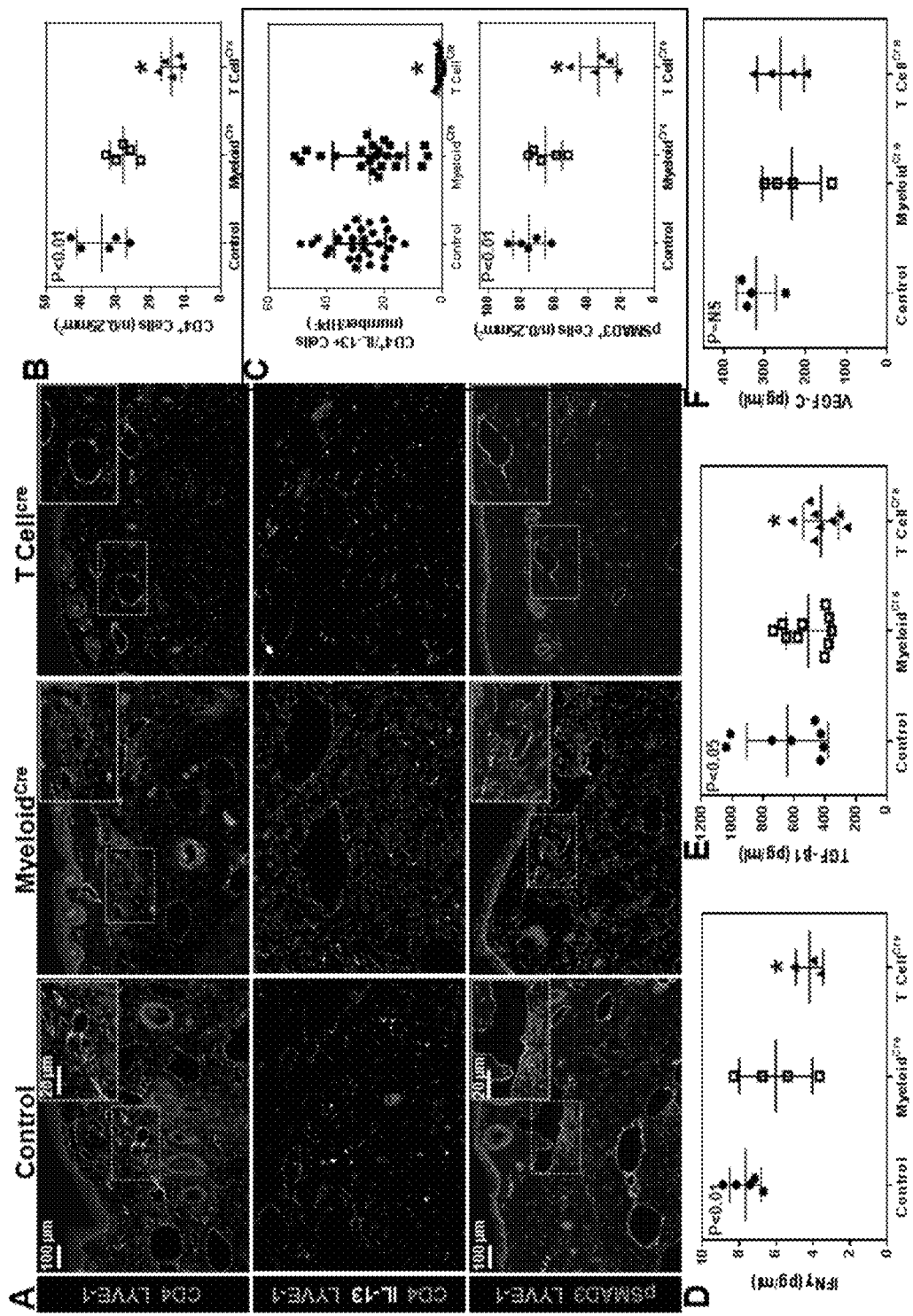
FIG. 22 shows that mice lacking T cells that express TGF-β1 have decreased perilymphatic inflammation and TGF-β1 expression. (A) shows representative photomicrographs of mouse hind limbs from various groups stained for CD4+ cells (top), IL13+ cells (middle), pSMAD3+ cells (bottom), and lymphatic vessels (LYVE-1+). Note decreased CD4+ cell accumulation, decreased number of IL13+ cells, and decreased number of pSMAD3+ cells in T Cell$^{cre}$ mice. (B) shows quantification of CD4+ cells in hind limb tissues of animals in various groups. (C) shows quantification of Th2 cells (CD4+/IL13+) in hind limb tissues of animals in various groups. (D) shows quantification of pSMAD3$^+$ cells in hind limb tissues of animals in various groups. (E)-(G) show serum levels of IFN-γ (E), TGF-β1 (F), and VEGF-C(G) protein concentration from control, Myeloid$^{Cre}$, and T Cell$^{Cre}$ mice.

Previously, we have shown that TGF-β1 immunotherapy in our tail model of lymphedema resulted in decreased inflammation, specifically T-helper cell tissue infiltration, in addition to decreased fibrosis. Avraham et al., *Am. J. Pathol.* 177:3202-3214 (2010). Interestingly, T Cell$^{cre}$ mice had markedly decreased numbers of T-helper cells infiltrating the dermis and subcutaneous fat as compared with Myeloid$^{cre}$ and control mice (FIG. 22 (A), (B); p<0.01). Furthermore, similar to our findings in the pirfenidone treated animals, we noted a significant decrease in accumulation of IFN-γ protein (FIG. 22 (D); p<0.01). Analysis of TGF-β1$^+$ cells and protein accumulation as well as cellular expression of its activated downstream signaling molecule, pSMAD3, was found to be markedly decreased in T Cell$^{cre}$ mice as compared with Myeloid$^{cre}$ and control mice (FIG. 22 (A), (C), (E); p<0.01 for pSMAD3 and p<0.05 for TGF-β1 protein). We found no difference in F4/80$^+$ cells or VEGF-C protein accumulation between all groups (FIG. 22 (F); p=NS). This correlated with significantly decreased dermal and subcutaneous type I collagen deposition in T Cell$^{cre}$ mice as compared with Myeloid$^{cre}$ and control mice (FIG. 21 (D); p<0.05). While there appeared to be a trend in decreased inflammation, fibrosis, and anti-lymphangiogenic cytokine expression in Myeloid$^{cre}$ mice it did not achieve significance. These findings are important because they indicate that the major cellular source of TGF-β1 in lymphedema is T cells.

Impaired LEC TGF-β1 Responsiveness had No Change in Tail Lymphedema, Inflammation, or Fibrosis in the Tail after Lymphatic Injury To analyze the direct effects of TGF-β1 on LECs in the setting of lymphedema and apply our previous in vitro findings to an in vivo model, we performed tail surgeries on FLT4$^{Cre}$ mice and analysis was performed 6 weeks after surgery. Avraham et al., *Plast. Reconstr. Surg.* 124:438-450 (2009). Phenotypic confirmation of these transgenic mice was confirmed with staining on lymph nodes for LYVE-1 and pSMAD3. FLT4$^{Cre}$ mice had no detectable pSMAD3 staining on LECs, indicating LEC unresponsiveness to TGF-β1 (FIG. 23 (A), white arrows indicate pSMAD3$^+$ LECs). FLT4$^{Cre}$ mice had no differences in gross tail swelling, tail volume, and fibroadipose thickness as compared to control mice (FIG. 23 (C)-(E), (G); p=NS). Interestingly and similar to our previous in vitro findings, we found increased lymphatic vessel density in the bridging portion of the wounds (FIG. 23 (H); p<0.01). Clavin et al., *Am. J. Physiol. Heart Circ. Physiol.* 295:H2113-H2127 (2008). The bridging portion of the wound is the area where all dermal lymphatic vessels were removed with surgery. Therefore, this indicates improved lymphangiogenesis as a result of LEC unresponsiveness to TGF-β1 in the setting of lymphedema.

Figure 23:
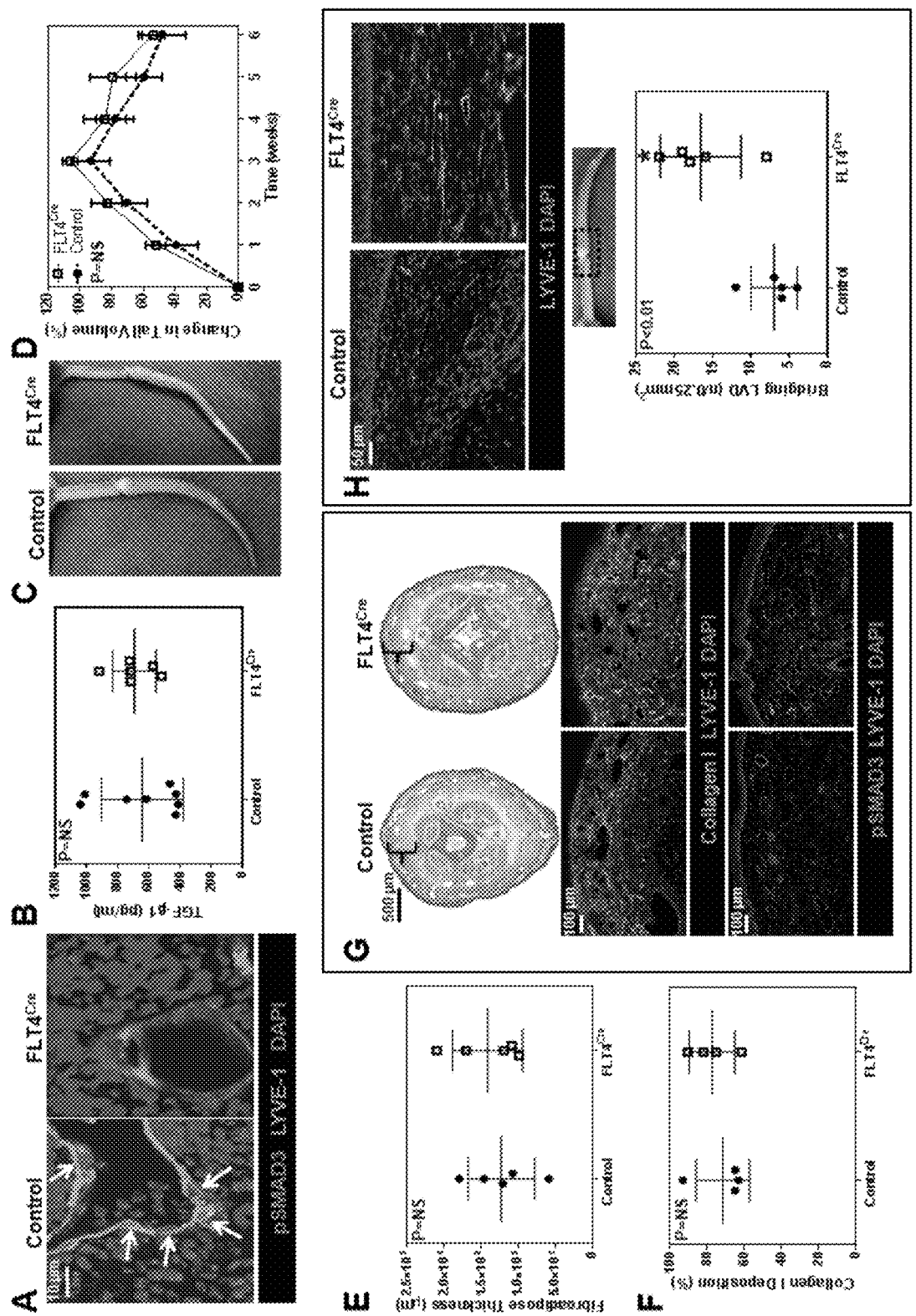
FIG. 23 shows that impaired LEC TGF-β1 responsiveness has no change in tail lymphedema, inflammation, or fibrosis, but has improved lymphangiogenesis. (A) shows representative high power (80×) images of lymph node sections harvested from control and FLT4$^{cre}$ mice with immunofluorescent co-localization of pSMAD$^+$ and LYVE-1, scale bar=10 μm. Arrows indicate co-localization of pSMAD3 in LYVE-1$^-$ vessels. (B) shows quantification of tail TGF-β1 protein concentration in control and FLT4$^{cre}$ mice 6 weeks after surgery (n=5 animals/group; p=NS for both). (C) shows representative photographs of control and FLT4$^{cre}$ mouse tails after surgical excision of superficial/deep collecting lymphatics 6 weeks after surgery. (D) shows a graphical representation of tail volume changes of FLT4$^{cre}$ mouse tails as compared with controls (n=5 animals/group; p=NS). (E) shows quantification of soft tissue changes of control and FLT4$^{cre}$ mice (n=5 animals/group; p=NS). (F) shows quantification of collagen I-staining area (n=5 animals/group; p=NS). (G) (upper panels) shows representative cross-sectional histological images of control and FLT4$^{cre}$ mouse tails harvested 6 weeks after lymphatic ablation. Brackets illustrate soft tissue thickness. Scale bar=500 μm. (G) (middle panels) shows representative 40× images of tail tissues harvested from control and FLT4$^{cre}$ animals 6 weeks after surgery with immunofluorescent localization of type I collagen and lymphatic vessels. (G) (lower panels) shows localization of pSMAD3 and lymphatic vessels. Scale bar=100 μm. (H) shows representative higher-power (60×) images of longitudinal tail tissue sections harvested from tail wounds of control and FLT4$^{cre}$ mice 6 weeks after surgery with immunofluorescent localization of LYVE-1, scale bar=50 μm. Quantifications of bridging LYVE-1 vessels density (LVD) (n/0.25 mm$^2$ area) for control and FLT4$^{cre}$ mice (n=5 animals/group; *p<0.01).

Analysis of the inflammatory infiltrating cells and cytokine accumulation between FLT4$^{Cre}$ and control mice revealed no differences in CD4$^+$ cells and IFN-γ protein accumulation (p=NS for both), F4/80$^+$ cells or VEGF-C protein accumulation (p=NS), TGF-β1$^+$ cells and protein accumulation (FIG. 23 (B); p=NS), as well as cellular expression of its activated downstream signaling molecule, pSMAD3 (FIG. 23 (G); p=NS). Similarly, collagen I deposition was not significantly different between FLT4$^{Cre}$ and control mice (FIG. 23 (F), (G); p=NS). These findings suggest that the main effect of TGF-β1 in promoting inflammation, fibrosis and ultimately lymphatic dysfunction is in the extracellular matrix while its direct anti-lymphangiogenic plays a relatively minor role in the setting of lymphedema.

Methods

Study Design

Our hypothesis was that lymphedema could be treated by TGF-β1 inhibition, thereby decreasing both inflammation and fibrosis. We explored different aspects of this hypothesis in several different animal models to allow us to thoroughly assess swelling, inflammation, fibrosis, lymphatic vessel function, and lymphangiogenesis after injury. Adult female (10-14 week old) C57BL/6J mice (Jackson Laboratories, Bar Harbor, Me.) were maintained in light- and temperature-controlled pathogen free environments, and fed ad libitum. All studies were approved by the Institutional Animal Care and Use Committee (IACUC) at Memorial Sloan Kettering Cancer Center. After undergoing tail surgery, animals were excluded from the experiment if they underwent distal tail necrosis. This assessment was made before animals were randomized to treatment or control groups. Each experiment was performed using a minimum of 6-8 animals and assays were performed in triplicate. All counts were performed by reviewers blinded to the intervention.

Animal Models and Treatments

Animals underwent lymphatic ablation using a well-described mouse tail model of lymphedema in which the superficial and deep lymphatic systems of the tail are excised through a 2 mm circumferential skin excision in the mid-portion of the tail. Clavin et al., *Am. J. Physiol. Heart Circ. Physiol.* 295:H2113-H2127 (2008); Avraham et al., *Am. J. Pathol.* 177:3202-3214 (2010); Rutkowski et al., *Microvasc. Res.* 72:161-271 (2006); Tabibiazar et al., *PLoS Med.* 3:e254 (2006). Our group and others have previously shown that this model results in sustained lymphedema of the distal tail, severe impairment in lymphatic function, and histological features of clinical lymphedema (e.g., chronic inflammation, adipose deposition, fibrosis) for at least 10 weeks postoperatively. Clavin et al., *Am. J. Physiol. Heart Circ. Physiol.* 295:H2113-H2127 (2008); Avraham et al., *Am. J. Pathol.* 177:3202-3214 (2010); Rutkowski et al., *Microvasc. Res.* 72:161-271 (2006); Tabibiazar et al., *PLoS Med.* 3:e254 (2006). Seven weeks after surgery, when lymphedema was established, animals were randomized to experimental (pirfenidone) or control groups and treated once daily for 3 weeks followed by analysis as outlined below.

The tail model is useful for analyzing histological tissue changes (i.e., fibrosis and adipose deposition); however, due to the small caliber of the collecting vessels this model, is not ideal for analyzing lymphatic pumping function. Therefore, to determine the efficacy of pirfenidone in restoring lymphatic pumping capacity of collecting lymphatics and to analyze the effect of this treatment on lymphatic proliferation in the tissues distal to the zone of lymphatic injury, we performed popliteal lymph node dissections (PLND) as previously described. Blum et al., *Breast Cancer Res. Treat.* 139:81-86 (2013). Briefly, the lymphatics were visualized after injection of 50 µl of 3% Evans Blue into the hind paw. The collecting lymphatics in the popliteal region, together with the popliteal lymph nodes, were excised. Two weeks following surgery, animals were randomized to treatment with systemic pirfenidone or control once daily for 2 weeks followed by analysis.

In systemic experiments, mice were treated orally daily with either pirfenidone (Cayman Chemical, Ann Arbor, Mich.) at a dose of 400 mg/kg dissolved in 10% DMSO/0.5% carboxymethycellulose (CMC) in PBS or with vehicle (10% DMSO/0.5% CMC in PBS). This dose was determined based on previous studies that showed an effective treatment regimen in various models of fibrosis. Oku et al., *Eur. J. Pharmacol.* 590:400-408 (2008); Kakugawa et al., *Eur. Respir. J.* 24:57-65 (2004); Tanaka et al., *Chest* 142:1011-1019 (2012). A topical formulation of pirfenidone was developed in collaboration with the Research Pharmacy Core Facility at Memorial Sloan Kettering Cancer Center. In these experiments, mice were treated daily with topical pirfenidone (Cayman Chemical, Ann Arbor, Mich.) 1 mg/ml in 41% petrolatum while control animals received vehicle alone (41% petrolatum).

To investigate the cellular source of TGF-β1 in lymphedema we developed non-inducible transgenic mice with selective knock out of TGF-β1 production from T cells and myelocytes. From Jackson Laboratories (Bar Harbor, Me.), we purchased B6.Cg-Tg(Lck-cre)548Jxm/J that express Cre under the control of the Lck (lymphocyte protein tyrosine kinase) promoter, enabling thymocyte-specific excision of loxP-flanked sequences of interest. The Lck gene is primarily expressed by T lymphocytes where it phosphorylates tyrosine residues of proteins involved with intracellular signaling pathways. Additionally, we purchased from Jackson Laboratories (Bar Harbor, Me.) a B6.129P2-Lyz2tm1 (cre)Ifo/J transgenic strain with the LysMcre knock-in allele that has a nuclear-localized Cre recombinase inserted into the first coding ATG of the lysozyme 2 gene (Lyz2); both abolishing endogenous Lyz2 gene function and placing NLS-Cre expression under the control of the endogenous Lyz2 promoter/enhancer elements. Each of these transgenic mice was crossed with Tgfb1$^{tm2.1Doe}$/J mutant mice (Jackson Laboratories, Bar Harbor, Me.) that harbor loxP sites flanking exon 6 of the TGF-β1 gene. As a result, Cre-mediated recombination results in deletion of the targeted gene (TGF-β1) in T lymphocytes and myeloid cell lineage (including monocytes, mature macrophages, and granulocytes).

To investigate the direct effects of TGF-β1 on LECs, we developed an inducible transgenic mouse with a non-functional TGF-β receptor on LECs. We used an FLT4cre mouse (a gift of Dr. Sagrario Ortega) where the Flt4 promoter of VEGFR-3 in these mice is under the control of estrogen receptor type 2 (ER2) and is highly expressed by all LECs in adult mice. Martinez-Corral et al., *Proc. Natl. Acad. Sci. USA* 109:6223-6228 (2012). We crossed FLT4cre mice with B6; 129-Tgfbr2tm1Karl/J (Jackson Laboratories, Bar Harbor, Me.) mutant mice that possesses loxP sites flanking exon 4 of the transforming growth factor, beta receptor II. Cre expression was induced in adult female FLT4$^{Cre}$ mice using tamoxifen (300 mg/kg/day subcutaneously for 5 days).

For all transgenic mice, gene expression of both transgenes was confirmed by genotyping (Transnetyx, Memphis, Tenn.) and double homozygous mice were backcrossed for 6 generations to ensure consistency. In addition, our lab performed confirmatory phenotypic studies for all of our newly developed transgenic models with gene expression using PCR, protein quantification using enzyme-linked immunosorbent assays (ELISA), and histologic staining (see below).

Tail Volumes, Lymphoscintigraphy, and Histological Analysis

Tail volumes were analyzed using multiple digital caliper tail circumference measurements distal to the zone of lymphatic injury and calculated using the truncated cone formula as previously described. Clavin et al., *Am. J. Physiol. Heart Circ. Physiol.* 295:H2113-H2127 (2008). Lymphoscintigraphy was also performed as previously described to quantify lymphatic flow to the sacral lymph nodes by injecting 50 µl of filtered technetium (Tc$^{99m}$) sulfur colloid into the distal tail. Avraham et al., *FASEB J.* 27:1114-1126 (2013). Decay-adjusted uptake was recorded in the sacral lymph nodes using an X-SPECT camera (Gamma Medica, Northridge, Calif.) and region-of-interest analysis was performed using ASIPro software (CTI Molecular Imaging, Knoxville, Tenn.). Clavin et al., *Am. J. Physiol. Heart Circ. Physiol.* 295:H2113-H2127 (2008).

For histological and immunohistochemical analysis, tail sections were harvested, briefly fixed in 4% ice cold paraformaldehyde (Sigma-Aldrich, St. Louis, Mo.), decalcified using 5% ethylenediaminetetraacetic acid (EDTA; Santa Cruz, Santa Cruz, Calif.), and embedded in paraffin. Hematoxylin and eosin sections were prepared using standard techniques and subcutaneous tissue thickness was quantified in standardized histological cross-sections by measuring the thickness of the skin and soft tissues in four quadrants of the tail by two blinded reviewers in a minimum of 6 animals per group.

Immunohistochemical staining was performed according to our established techniques. Avraham et al., *Am. J. Pathol.* 177:3202-3214 (2010). Paraffin-embedded tissues were rehydrated and antigen unmasking was performed using boiling sodium citrate (Sigma-Aldrich, St. Louis, Mo.) followed by quenching of endogenous peroxidase activity with 2% BSA/20% animal serum. Tissues were incubated with primary antibody overnight at 4° C. Primary antibodies used for immunohistochemical stains included, LYVE-1, CD45, and CD4 (all from R&D, Minneapolis, Minn.), F4/80, TGF-β1, pSMAD3, Podoplanin (all from Abcam, Cambridge, Mass.), alpha-SMA (Sigma-Aldrich, St. Louis, Mo.), iNOS (BD biosciences, San Jose, Calif.), and CD3 (Dako North America, Inc. Carpinteria, Calif.). All secondary antibodies were obtained from Vector Laboratories. Slides were analyzed after being scanned using a Mirax slide scanner (Zeiss, Munich, Germany). Type I collagen immunohistochemistry was performed using an antibody to mouse type I collagen (Abcam, Cambridge, Mass.) and quantified as a ratio of the area of positively stained dermis within a fixed threshold to total tissue area using Metamorph Offline software (Molecular Devices, Sunnyvale, Calif.). Cell counts were performed on high-powered sections, with a minimum of 4-6 animals per group and 4-5 HPF/animal by two blinded reviewers.

Protein Analysis

Tail tissues for protein analysis was harvested 1.5 cm distal to the lymphatic injury, flash frozen, crushed and extracted with tissue extraction protein reagent (ThermoFisher Scientific, Waltham, Mass.) mixed with phosphatase and protease inhibitor (Sigma-Aldrich, St. Louis, Mo.). 20-30 mg of protein from samples (n=3-5 animals/group) was analyzed by ELISA to quantify TGF-β1, interferon-gamma (IFN-γ), and vascular endothelial growth factor-C(VEGF-C) according to the manufacturer's protocol (eBioscience, San Diego, Calif.). All experiments were performed in duplicate.

In Vivo Imaging of Lymphatic Vessel Function

To assess the contractility of hind limb collecting lymphatic vessels, videos were recorded with near infrared imaging (NIR) after 15 µl of 0.15 mg/ml indocyanine green (ICG) (Sigma-Aldrich, Saint Louis, Mo.) was injected intradermally in the dorsal aspect of the hind foot. Twenty minutes was allowed after injection to allow uptake into the collecting vessels. The animals were then imaged using a custom-made EVOS EMCCD camera (Life Technologies, Carlsbad, Calif.) and a LED light source (CoolLED, Andover, UK). Video images were obtained using a Zeiss V12 Stereolumar microscope (Caliper Life Sciences, Hopkinton, Mass.). Images were obtained every eight seconds for 30 minutes. Lymphatic pumping function was analyzed using Fiji software (a free open source data analysis tool developed by the National Institutes of Health, Bethesda, Md.). A region-of-interest was selected over the dominant collecting vessel and the noise-subtracted fluorescent intensity was plotted over time. In order to evaluate intrinsic pumping function, the initial ten minutes of each video was excluded due to lymphatic stimulation from positioning, and only the final 20 minutes to each video were analyzed. The pumping function was quantified in pulsations per minute.

Gene Expression PCR

To confirm the phenotype of knock out of TGF-β1 from T cells and myelocytes, spleens were harvested from these mice. T cells were isolated from spleens of T Cell$^{cre}$ transgenic mice using positive selection CD3 magnetic beads (Miltenyi Biotec, Cambridge, Mass.) as per the manufacture's recommendations. Similarly, myeloid cells were isolated from spleens of Myeloid$^{cre}$ transgenic mice using positive selection CD11b magnetic beads (Miltenyi Biotec, Cambridge, Mass.) as per the manufacture's recommendations. Isolated cells were then placed in TRIzol. RNA was isolated using a standard TRIzol extraction procedure. Chomczynski et al. *Anal. Biochem.* 162:156-159 (1987); Ribaudo et al., *Curr. Protocols Immunol.*, (Coligan et al. eds.) Chapter 10, Unit 10 11 (2001). Reverse transcription was performed using TaqMan Reverse Transcription reagents (Applied Biosystems, Foster City, Calif.) followed by quantitative reverse transcriptase polymerase chain reaction (RT-PCR) using TaqMan Universal Mastermix (Applied Biosystems) and LightCycler thermocycler (Roche Diagnostics, Indianapolis, Ind.). TGF-β1 expression levels were normalized to GAPDH. Experiments were performed in triplicate.

Modulation of TGF-β1 Activity

Because previous studies have suggested that a major mechanism of action of pirfenidone is blockade of TGF-β1 activity, we compared the effect of pirfenidone treatment with TGF-β1 immunotherapy after PLND in separate studies. Schaefer et al., *Eur. Respir. Rev.* 20:85-97 (2011). Importantly, we have previously shown that monoclonal antibodies directed against TGF-β1 are not only effective in neutralizing TGF-β1 biologic activity but that this treatment markedly decreases lymphedema and improves lymphatic function. Avraham et al., *Am. J. Pathol.* 177:3202-3214 (2010). Animals underwent PLND as outlined above and two weeks after surgery were randomized to treatment with either TGF-β monoclonal mouse neutralizing antibody (TGFmab; clone 1D11; Bio-x-cell, West Lebanon, N.H.) alone or pirfenidone plus TGFmab at a dose of 5 mg/kg diluted in 150 µl of PBS delivered intraperitoneally three times per week. Ruzek et al., *Immunopharmacol. Immunotoxicol.* 25:235-257 (2003). Control animals were treated with either vehicle control for pirfenidone or non-specific isotype antibodies delivered intraperitoneally at the same schedule as TGFmab.

Statistical Analysis

Statistical analysis was performed using GraphPad Prism (GraphPad Software, Inc., San Diego, Calif.) software. The Student's T-test was used to compare differences between two groups. Analysis between multiple time points (lymphoscintigraphy) was performed using a two-way ANOVA with post hoc tests to compare individual groups. Descriptive analysis and graphical methods were used to analyze and summarize results. Data is presented as mean standard deviation unless otherwise noted, with p<0.05 considered significant.

Conclusions

One purpose of this study was to analyze the efficacy of pirfenidone on the treatment of lymphedema in preclinical mouse models of lymphedema and lymphatic injury. Using two different mouse models, we show that both systemic and topical pirfenidone treat established lymphedema, markedly decreasing fibrosis and improving lymphatic function. Treatment with pirfenidone decreases chronic inflammatory reactions and markedly increases lymphatic collecting vessel pumping capacity after lymphadenectomy. In addition, pirfenidone was highly effective in preventing fibrosis after lymphatic injury, and it is likely that this response is secondary to inhibition of TGF-β1. Using TGF-β1 immunotherapy in our PLND model, we showed pirfenidone's major effect to be TGF-β1 inhibition and that maximal inhibition of TGF-β1 was achieved at the doses we utilized. Furthermore, using our tail model of lymphedema in our mice, we show that T cells, specifically CD4$^+$ cells, are the predominant source of TGF-β1 in the setting of lymphedema. In addition, we showed that the lack of TGF-β1 from T cells reduced lymphedema-induced chronic inflammation such as CD4$^+$ cells along with Th1 and Th2 cytokines.

Example 3. Treatment and Prevention of Lymphedema Using Teriflunomide

To test the efficacy of teriflunomide in preventing lymphatic dysfunction after lymphatic injury, we used a well described mouse model of popliteal lymph node dissection (PLND) in which popliteal lymph nodes are removed using a small skin incision. In order to test the efficacy of this treatment in treating established lymphedema, we used a mouse tail model of lymphedema in which the superficial and deep lymphatic system of the tail is disrupted and animals develop histological changes that are consistent with clinical disease.

Animals were randomized to either the PLNID or tail lymphedema groups and 2 weeks after surgery were treated with a topical formulation of teriflunomide (27 mg/ml; Tocris Bioscience, Minneapolis, Minn.) or vehicle control (Aquaphor/glycerin ointment) once daily for 2-4 weeks (2 weeks after PLND; 4 weeks after tail lymphedema). Our topical formulation was developed in collaboration with the Research Pharmacy Core Facility at Memorial Sloan Kettering Cancer Center. Mice were then sacrificed and lymphatic function, fibrosis, lymphangiogenesis were all assessed using standard assays.

Figure 24:
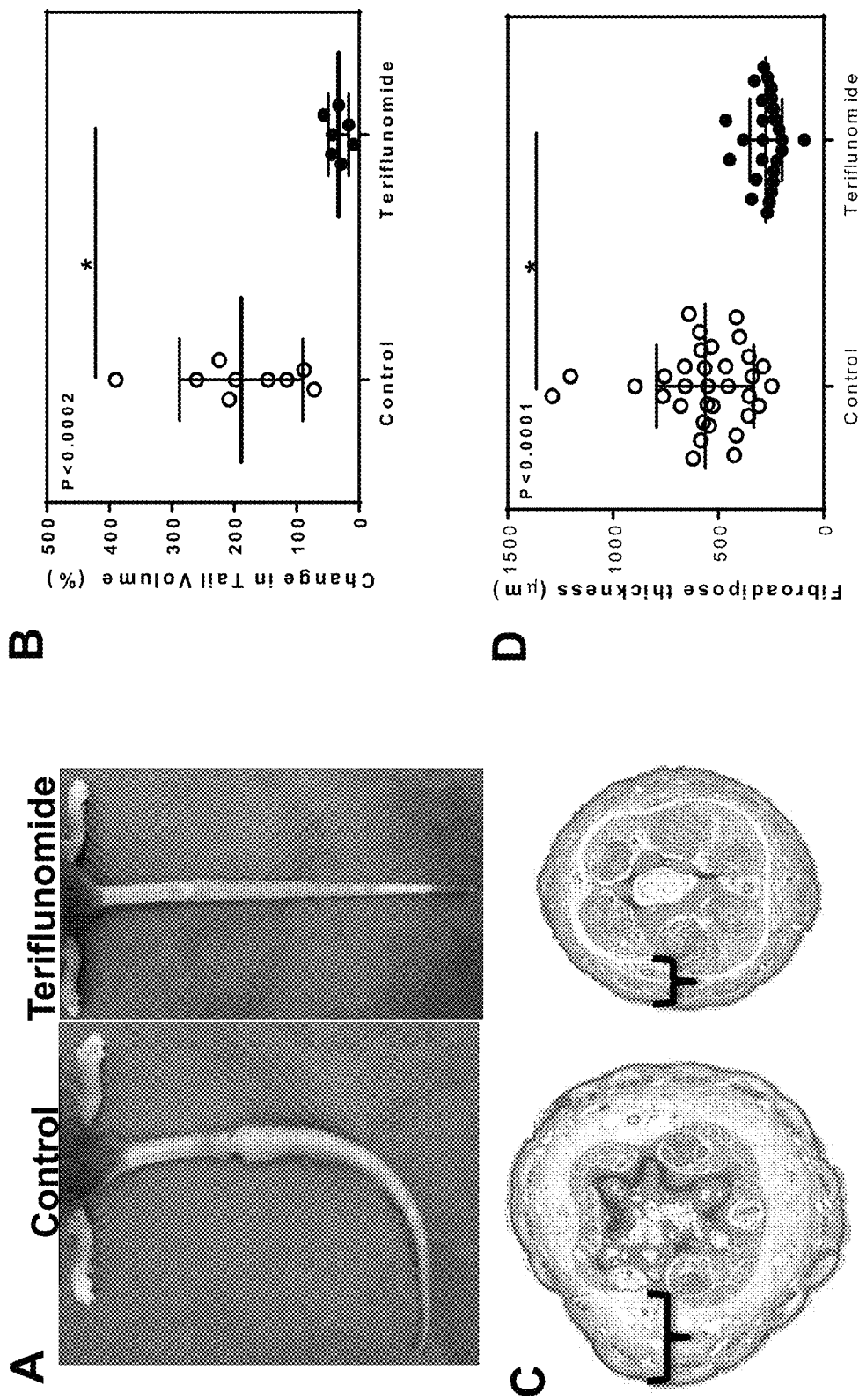
FIG. 24 shows that teriflunomide decreases lymphedema. (A) shows a gross photomicrograph of mouse tails treated with vehicle (control) or topical teriflunomide 6 weeks following lymphatic ablation. (B) shows a change in tail volume 6 weeks after lymphatic ablation in animals treated with vehicle or topical teriflunomide ((*p<0.0002). (C) shows histological cross-sections of mouse tails harvested 1 cm distal to the zone of lymphatic injury in control and teriflunomide treated mice. Brackets show area of fibroadipose tissue deposition. (D) shows quantification of fibroadipose tissue deposition in tail cross-sections of mice treated with vehicle control or topical teriflunomide (*p<0.0001).
Figure 25:
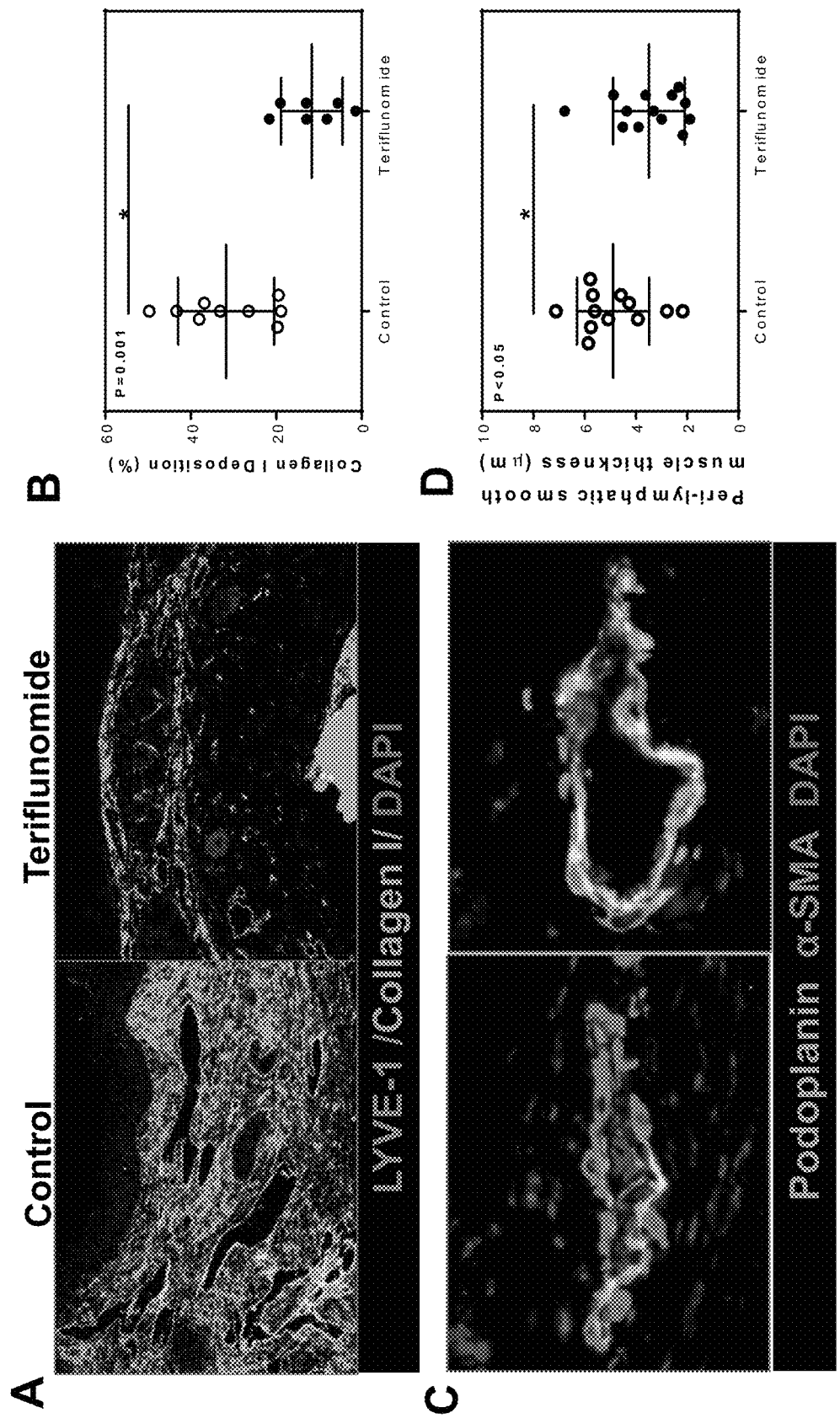
FIG. 25 shows that teriflunomide decreased fibrosis. (A) shows a representative photomicrograph of mouse tail cross-sections from control and teriflunomide treated mice localizing type I collagen fibers and dermal lymphatics. Notice marked decrease fibrosis in teriflunomide treated animals. (B) shows quantification of Type I collagen deposition in mice tails treated with vehicle control or topical teriflunomide (*p<0.001). (C) shows a representative photomicrograph of a main hind limb collecting vessel in animals treated with control or teriflunomide localizing α-SMA and podoplanin. Note decreased proliferation of α-SMA positive cells and wider lumen of collecting lymphatics in teriflunomide treated mice. (D) shows quantification of peri-lymphatic smooth muscle thickness in control and teriflunomide treated mice following PLND (*p<0.05).

Treatment of mice with topical teriflunomide after tail lymphatic ablation markedly decreased lymphedema and fibroadipose deposition, the histological hallmark of the disease (FIG. 24 (A)-(D)). While control mice had obvious swelling and fibrosis of the tail (fixed, "J-configuration" resulting from asymmetric collagen deposition), teriflunomide treated mice had essentially normal appearing tails 6 weeks after lymphatic injury (FIG. 24 (A)). These gross changes corresponded to a nearly 6-fold decrease in tail volume in teriflunomide treated mice (FIG. 24 (B)). Histological cross sections of control mice tails showed significant accumulation of fibroadipose tissues; in contrast, teriflunomide treated mice had minimal adipose tissue deposition (FIG. 24 (C), (D)). This finding was confirmed with type I collagen immunofluorescent staining demonstrating encasement of superficial lymphatics by collagen fibers in control animals and marked decreases in collagen deposition in teriflunomide treated animals 6 weeks after injury (FIG. 25 (A), (B)). In addition, teriflunomide decreased proliferation of alpha smooth muscle cells surrounding collecting lymphatics thus maintaining a more normal anatomical configuration of these vessels (FIG. 25 (C), (D)).

Figure 26:
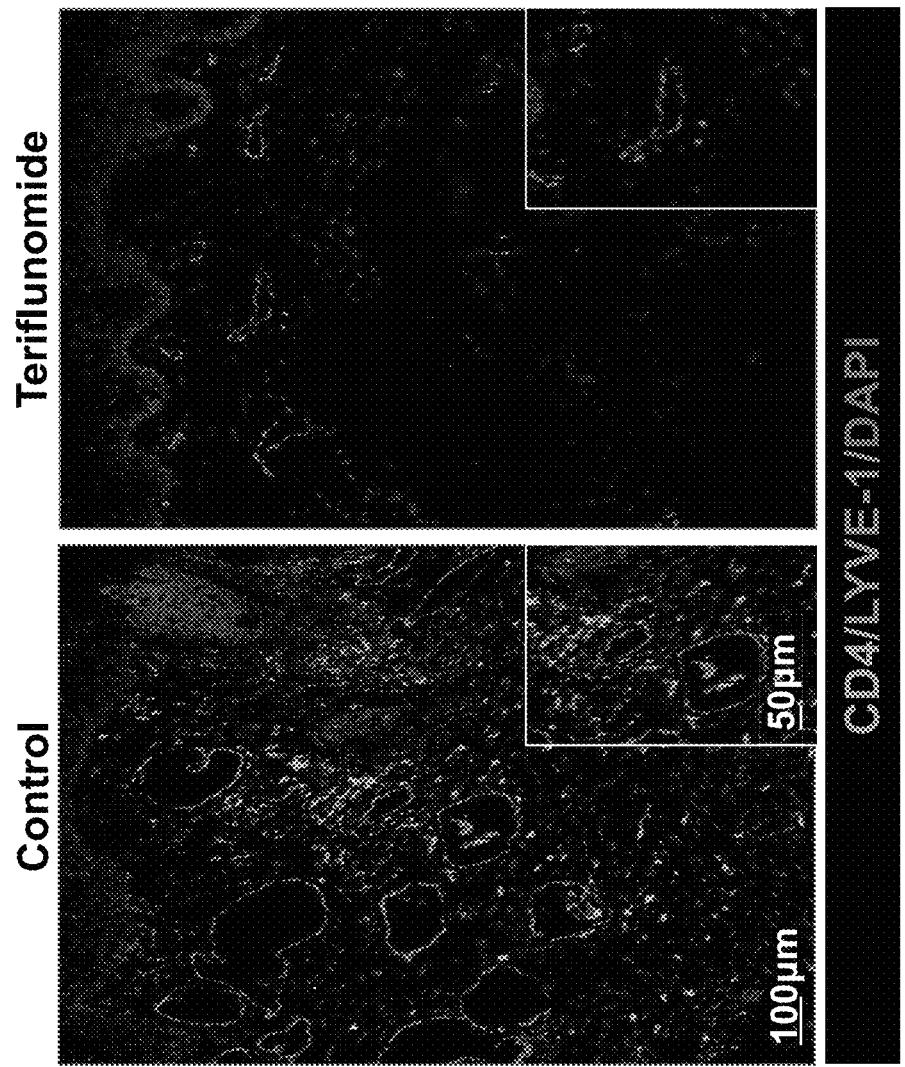
FIG. 26 shows that teriflunomide decreases inflammation. (A) shows a representative photomicrograph of mouse tail cross-sections from control and teriflunomide treated mice, localizing CD4$^+$ cells and dermal lymphatics. There is a marked decrease in CD4+ cell infiltration in teriflunomide-treated animals. Box insert shows a high power view (80×). (B) shows quantification of CD4$^+$ cells in mice tails treated with vehicle control or topical teriflunomide (*p<0.0001).

To determine if teriflunomide therapy decreased infiltration of CD4+ cells, we next analyzed tissue sections from control and treated mice using immunofluorescent antibodies targeting CD4 (FIG. 26 (A), (B)). This analysis demonstrated a marked decrease in CD4+ cell infiltration tail tissues harvested from teriflunomide treated animals as compared with controls. In fact, teriflunomide therapy decreased the number of infiltrating CD4+ cells by more than 8-fold (P<0.001).

Figure 27:
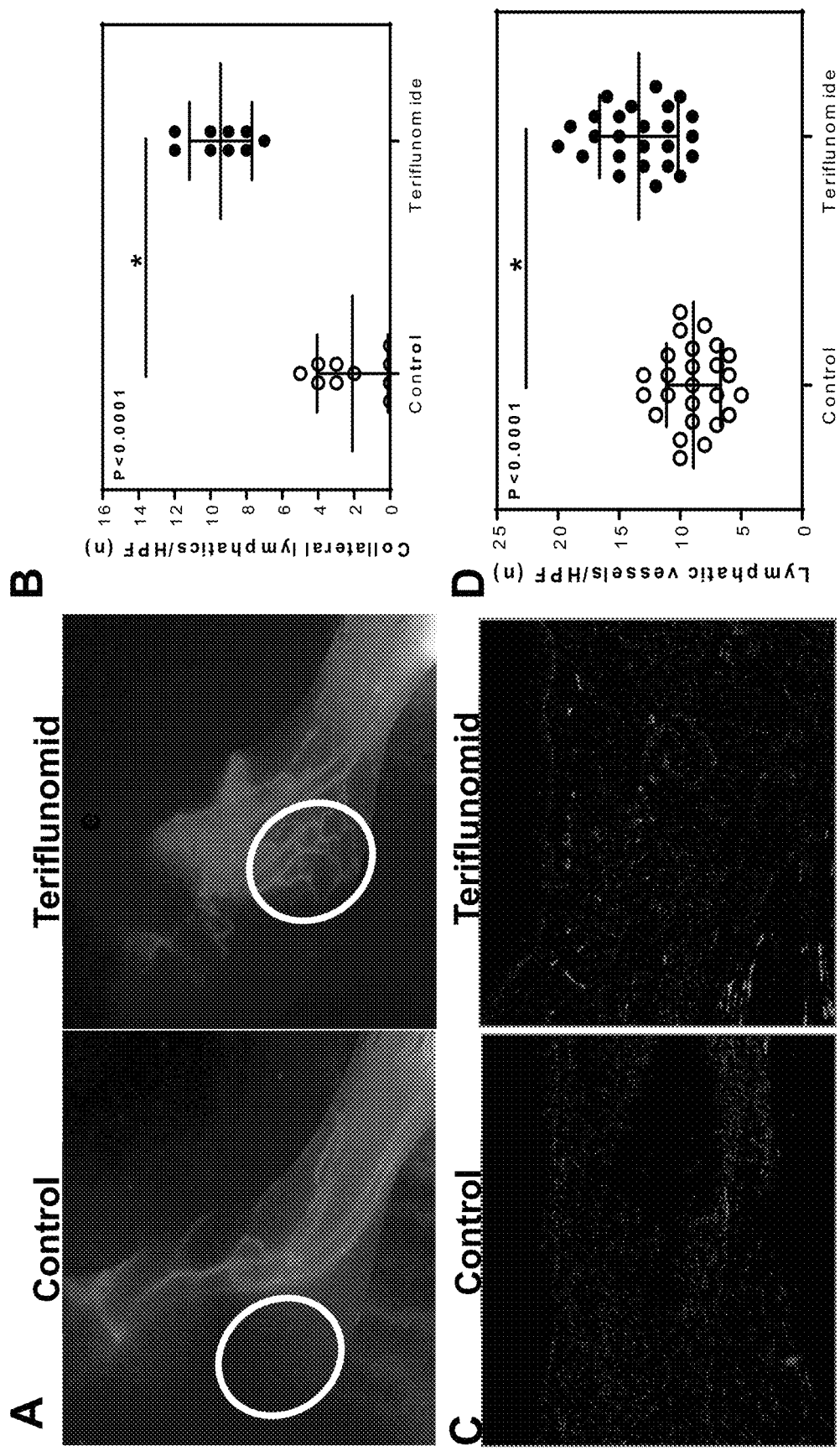
FIG. 27 shows that teriflunomide increases lymphangiogenesis. (A) shows a representative photomicrograph of near infra-red imaging of mouse hind limb lymphatics and collateral vessel formation (white circles) in animals treated with vehicle control or teriflunomide. Newly formed collateral lymphatics bypass the popliteal lymph node in teriflunomide-treated mice. (B) shows quantification of collateral lymphatic formation in animals following PLND and treated with vehicle control or teriflunomide (*p<0.001). (C) shows a representative photomicrograph of the tail wound in mice treated with vehicle control or topical teriflunomide localizing newly formed crossing lymphatic vessels. There is a marked increase in lymphangiogenesis in teriflunomide-treated mice. (D) shows quantification of collateral lymphatics in mouse tail wounds of control and teriflunomide treated animals 6 weeks after lymphatic ablation (*p<0.001).

Recent studies have shown that CD4+ cells produce potent anti-lymphangiogenic cytokines including interferon gamma, interluekin-4 (IL4), and IL13. Consistent with this, we found that treatment of animals that underwent PLND with teriflunomide markedly increased (4.5 fold; p<0.001) formation of collateral lymphatic vessels bypassing the zone of injury as assessed using indocyanine green (ICG) near infra-red imaging (FIG. 27 (A)). Similarly, treatment of mice with teriflunomide after tail lymphatic ablation resulted in a significant increase in newly formed lymphatics that crossed the zone of injury as compared with controls (FIG. 27 (B)).

Figure 28:
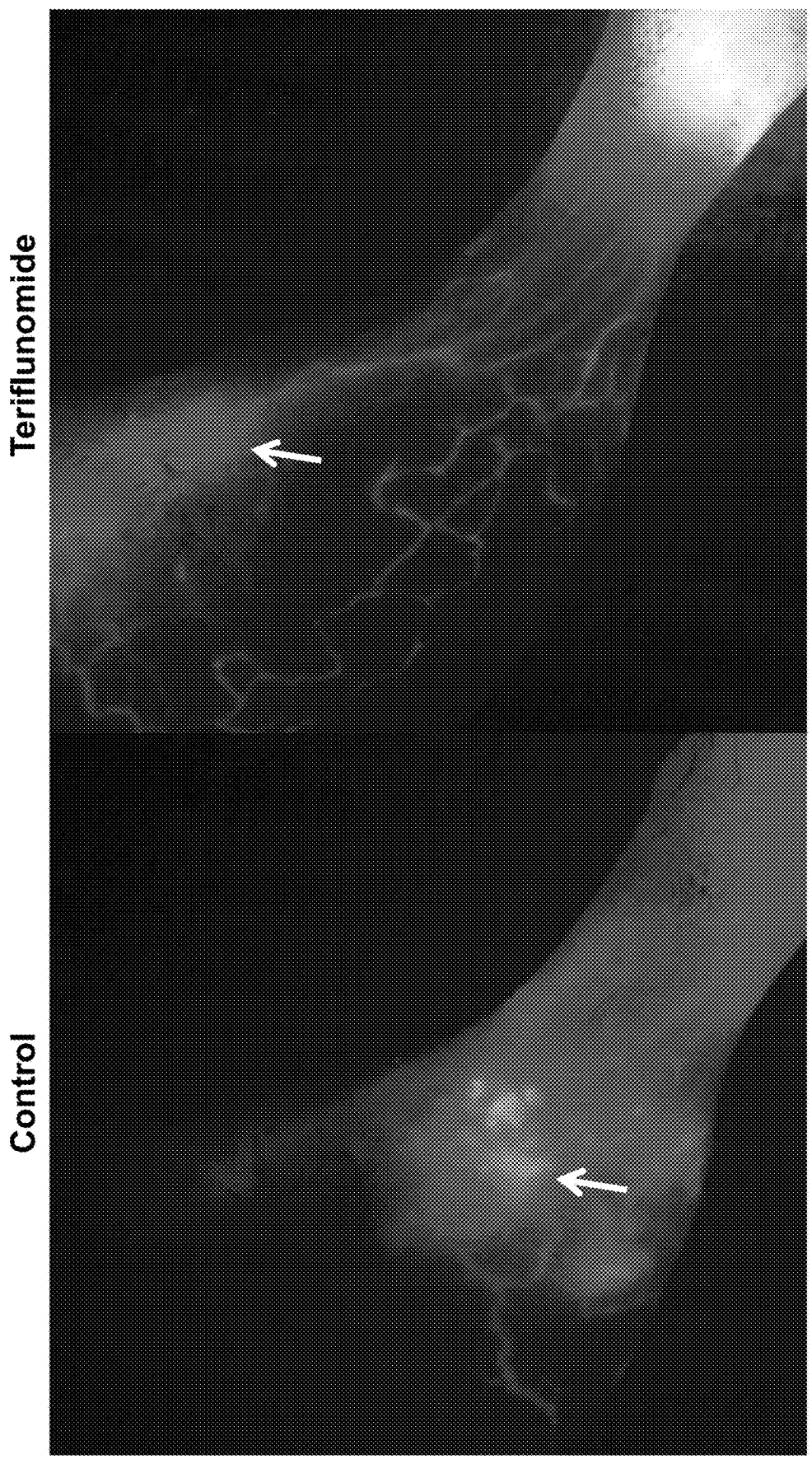
FIG. 28 shows that topical teriflunomide decrease lymphatic leakiness. Representative near infra-red image of lymphatic vessels in the hind limb of mice treated with vehicle control or teriflunomide after PLND. Note decreased leakiness of lymphatic vessels (arrows) in teriflunomide-treated mice.

The regeneration of collateral lymphatics in teriflunomide animals significantly decreased leakiness of lymphatic vessels in the dermis enabling greater amounts of interstitial fluid to be propagated proximally (FIG. 28).

Figure 29:
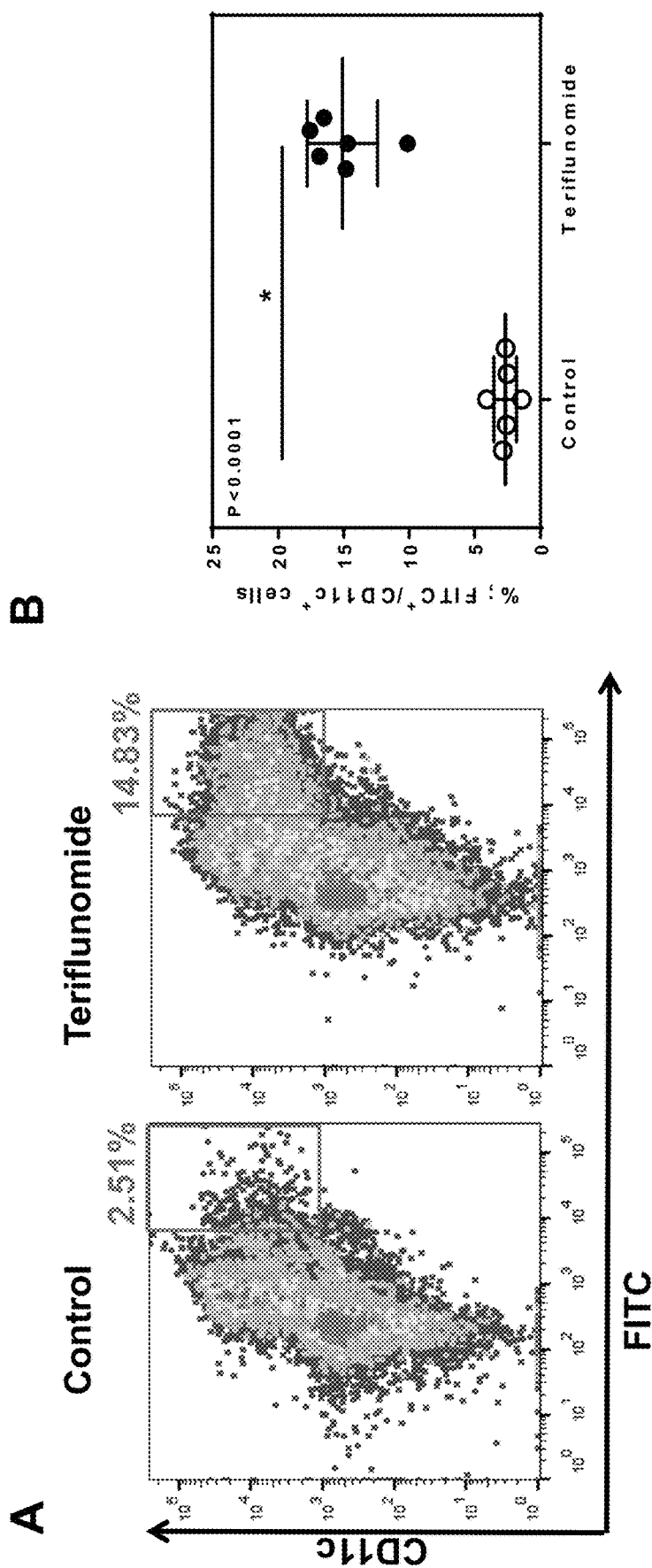
FIG. 29 shows that topical teriflunomide increases lymphatic function. (A) shows a representative flow cytometry plot of trafficked dendritic cells (DCs) in inguinal lymph nodes of mice treated with vehicle control or teriflunomide following PLND. Mice were treated with a topical formulation of FITC in the distal hind limb to tag tissue resident DCs and 24 hours later the inguinal lymph nodes were harvested and analyzed using flow cytometry to quantify the number of DCs that had trafficked from the periphery. Marked increase in DC trafficking indicates improved lymphatic function in teriflunomide-treated animals. (B) shows quantification of DC trafficking in control and teriflunomide-treated animals (n=6; *p<0.0001).

The newly formed lymphatics and decreased pathological changes in existing lymphatics of teriflunomide treated mice translated to markedly improved lymphatic function as analyzed by migration of dendritic cells (DCs). DCs migrate from the peripheral tissues via lymphatic vessels to regional lymph nodes to present antigens and promote adaptive immune responses. Analysis of DC trafficking in teriflunomide animals after PLND using a standard assay (FITC painting) demonstrated a more than 5-fold increase in the number of DCs that had trafficked to the inguinal lymph node (the next lymph node in the chain following the popliteal lymph node) as compared with controls (FIG. 29 (A), (B)). Because DCs only traffic via the lymphatics, this finding provides substantial evidence that teriflunomide increases lymphatic function.

Figure 30:
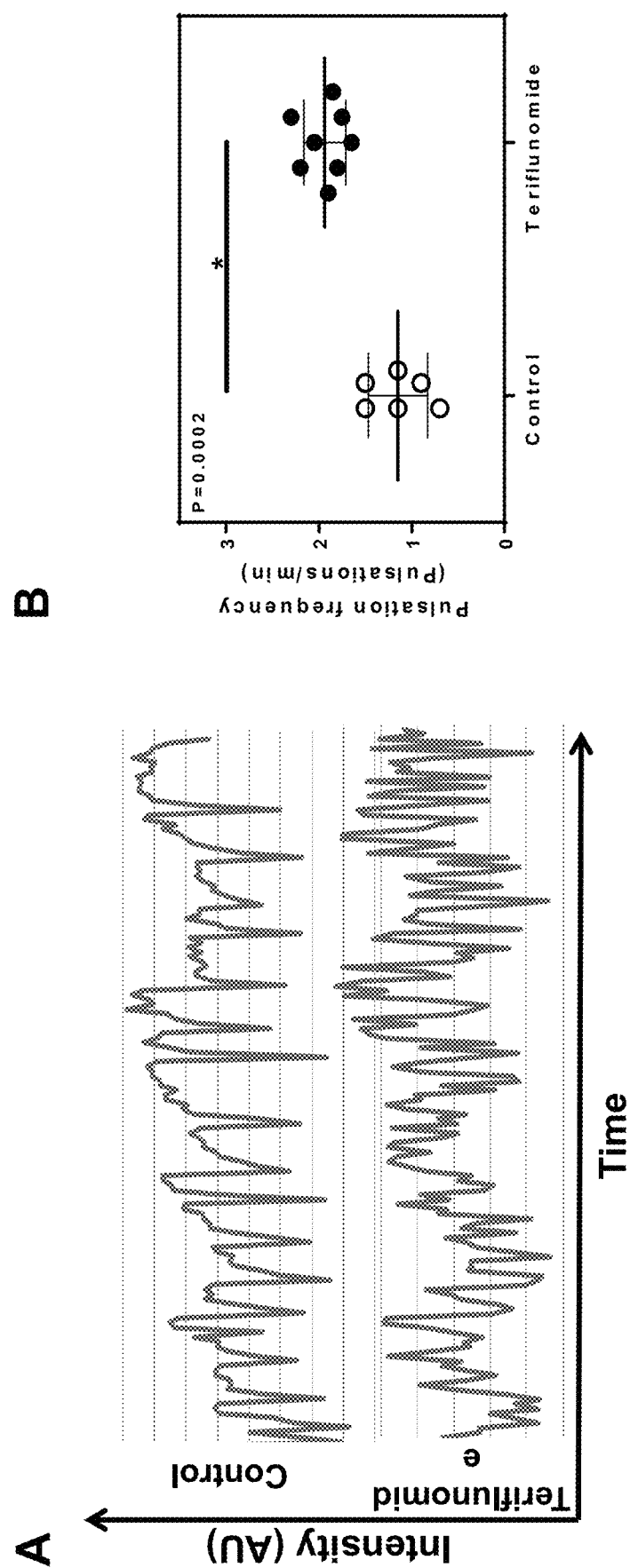
FIG. 30 shows that topical teriflunomide increases lymphatic pumping. (A) shows a plot of hind limb collecting lymphatic pumping in control and teriflunomide treated mice following PLND. (B) shows quantification of hind limb collecting lymphatic pumping frequency in control and teriflunomide-treated mice following PLND. Note significant increase in pumping in teriflunomide treated animals (*p<0.002).
Figure 36:
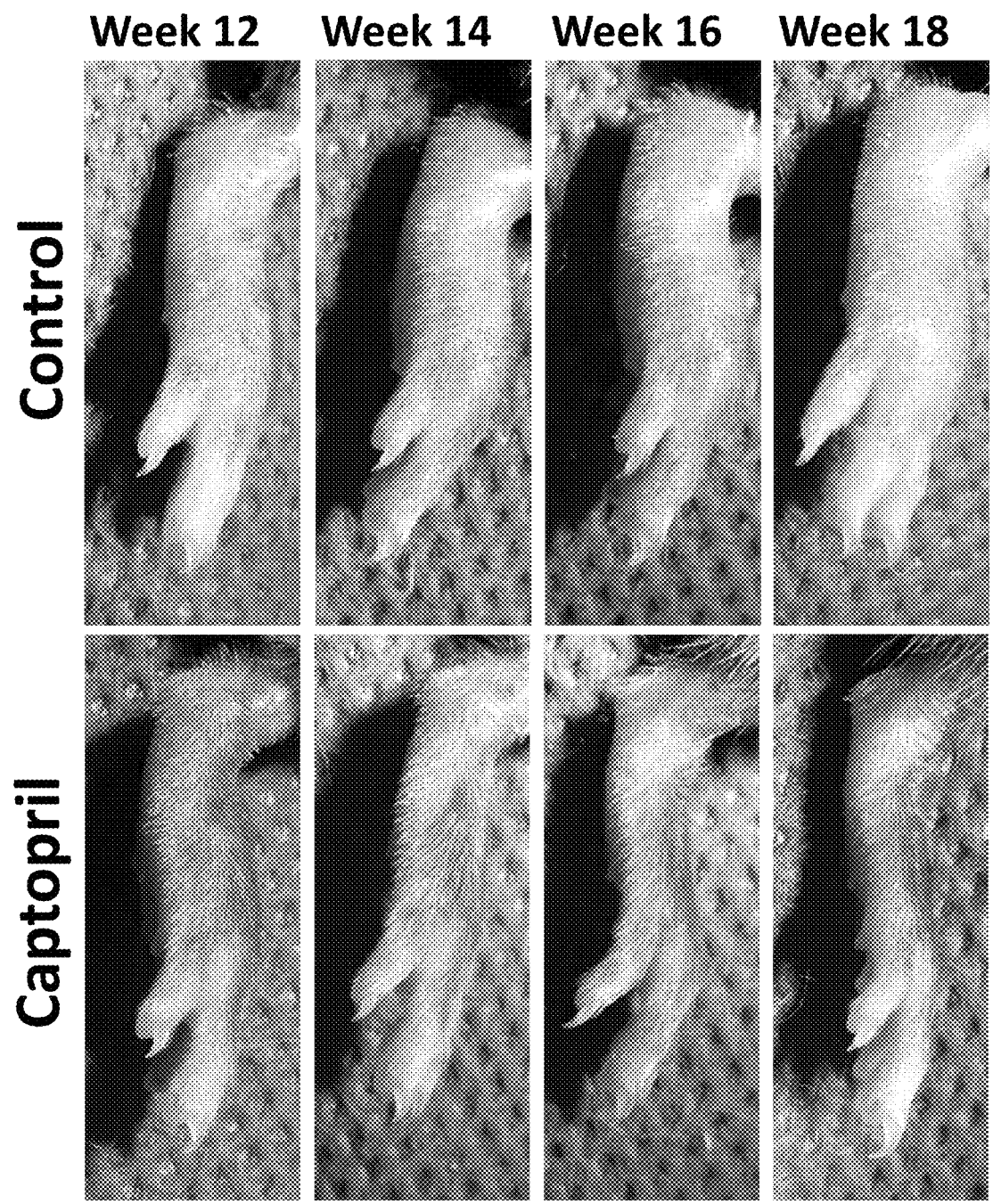
FIG. 36 shows that captopril treatment decreases foot swelling after hind limb lymphatic ablation with DT. Representative photographs of mouse feet in control (top) and Captopril treated (bottom) groups at various times following DT lymphatic ablation. Note obvious decrease in foot swelling in captopril treated mice.
Figure 37:
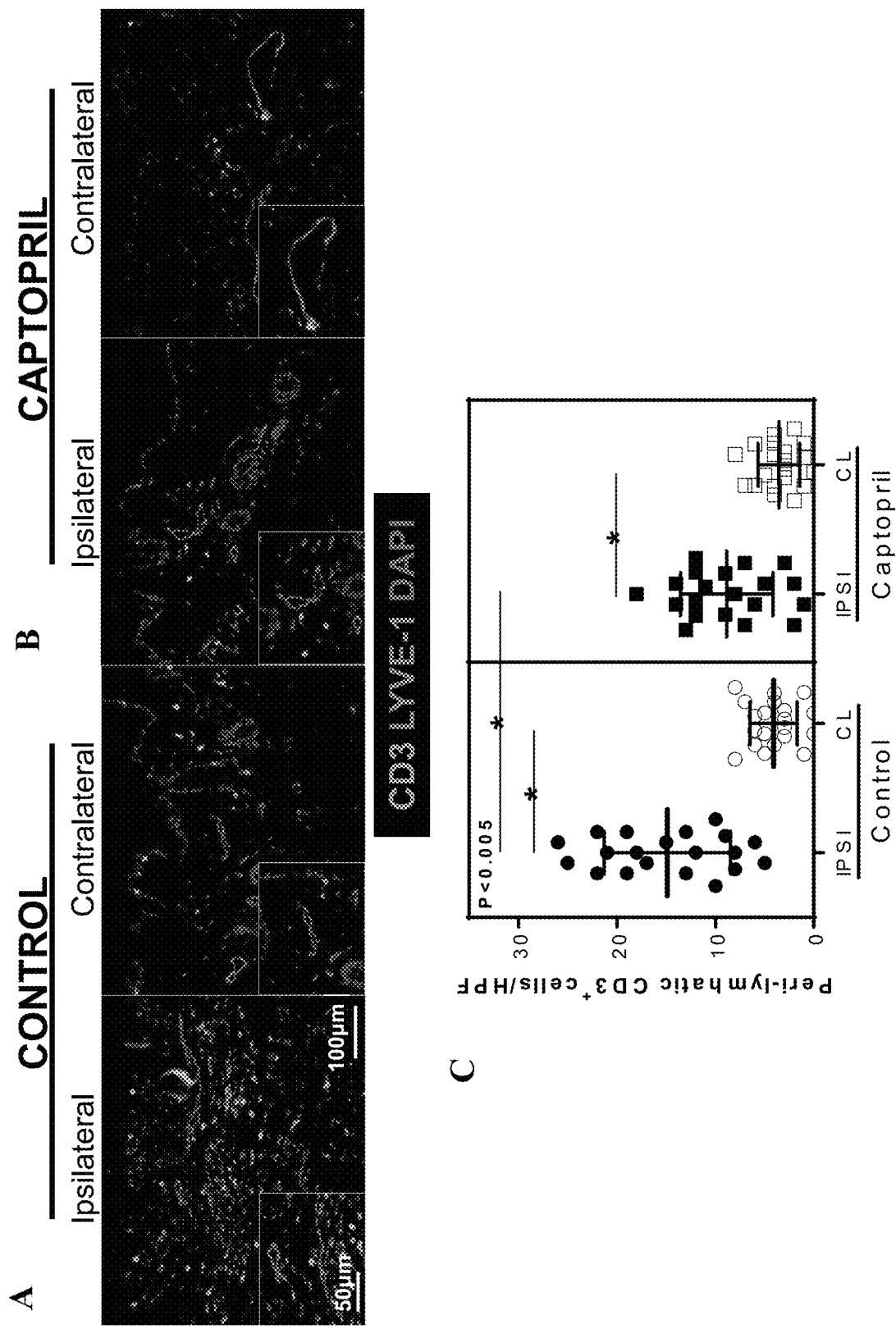
FIG. 37 shows that captopril treatment decreases T cell infiltration after hind limb lymphatic ablation with DT. Representative high power photomicrographs of control (A) and captopril treated (B) mouse hind limb sections stained for CD3+(T cell marker) and LYVE-1 (lymphatic marker). Ipsilateral tissues are harvested from the limb treated with DT while contralateral tissues are from the opposite untreated limb. Nuclear counterstain is shown with DAPI. (C) shows Quantification of CD3+ cells in hind limb tissues of control and captopril treated mice. Note significant difference (*p<0.05) between ipsilateral control and ipsilateral captopril limbs.
Figure 38:
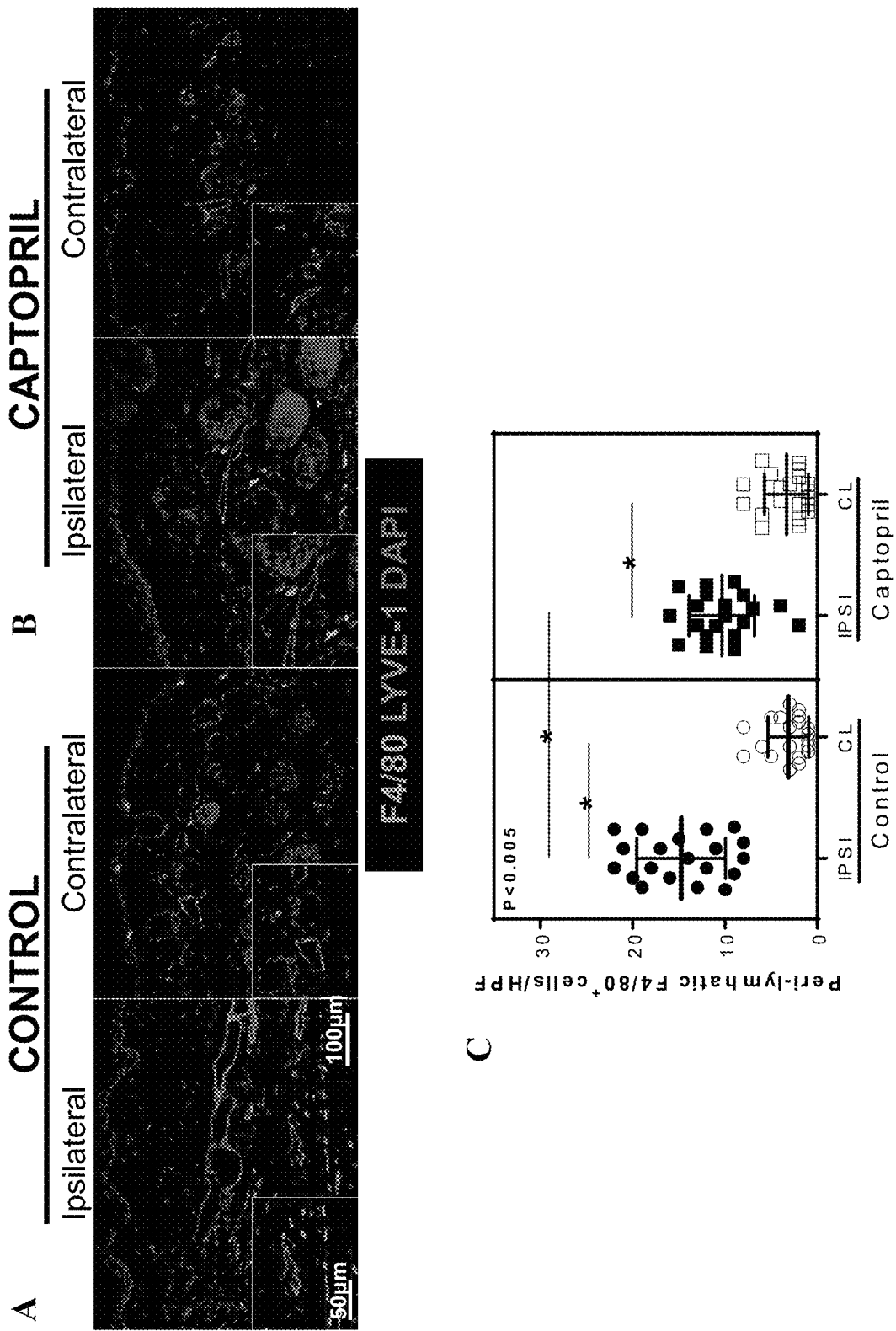
FIG. 38 shows that captopril treatment decreases hind limb macrophage infiltration after lymphatic ablation with DT. Representative high power photomicrographs of control (A) and captopril treated (B) mouse hind limb sections stained for F4/80 (macrophage marker) and LYVE-1 (lymphatic marker) are shown. Nuclear counterstain is shown with DAPI. (C) shows quantification of F4/80+ cells in hind limb tissues of control and captopril treated mice. Note significant difference (*p<0.005) between ipsilateral control and ipsilateral captopril limbs.
Figure 39:
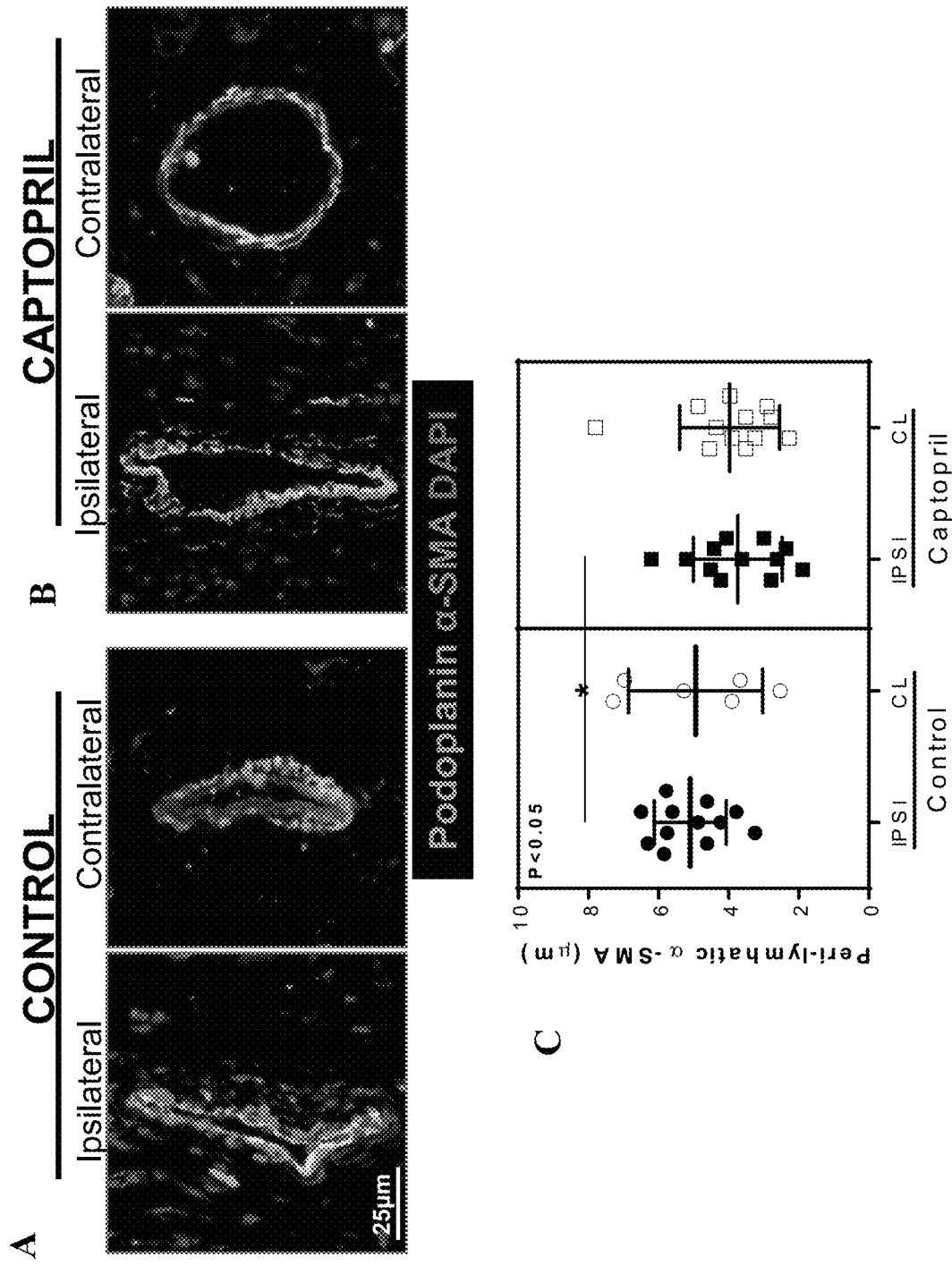
FIG. 39 shows that captopril treatment decreases hind limb collecting vessel smooth muscle deposition after lymphatic ablation with DT. Representative high power photomicrographs of control (A) and captopril treated (B) mouse hind limb sections stained for alpha smooth muscle actin ($\alpha$-SMA) (smooth muscle marker) and podoplanin (lymphatic marker). Nuclear counterstain is shown with DAPI. (C) shows quantification of $\alpha$-SMA+ cells in hind limb tissues of control and captopril treated mice. Note significant difference (*p<0.05) between ipsilateral control and ipsilateral captopril limbs.
Figure 41:
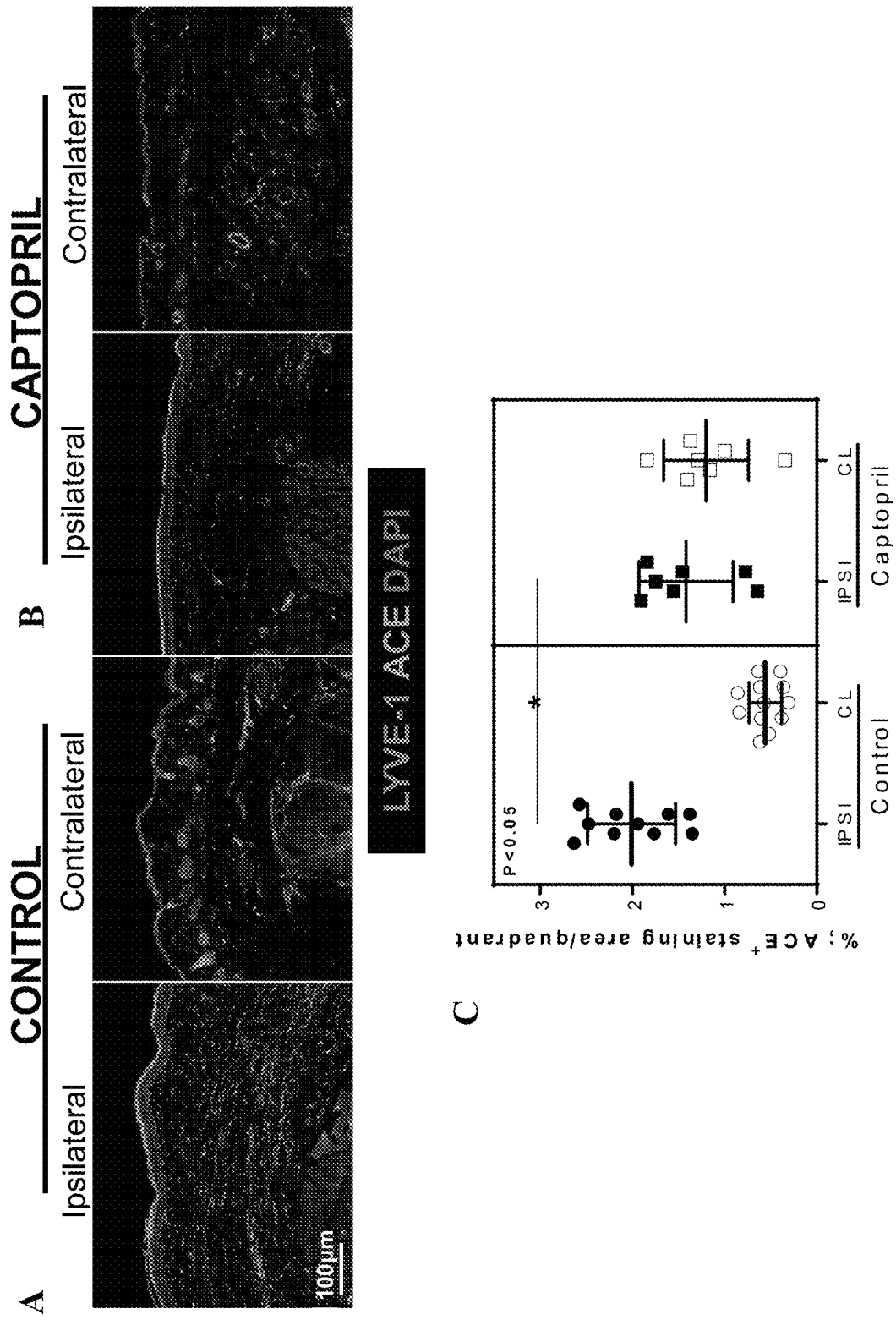
FIG. 41 show that captopril treatment decreases hind limb angiotensin converting enzyme (ACE) expression after lymphatic ablation with DT. Representative high power photomicrographs of control (A) and captopril treated (B) mouse hind limb sections stained for ACE and LYVE-1 (lymphatic marker). Nuclear counterstain is shown with DAPI. (C) shows quantification of ACE in hind limb tissues of control and captopril treated mice. Note significant difference (*p<0.0001) between ipsilateral control and ipsilateral captopril limbs.
Figure 42:
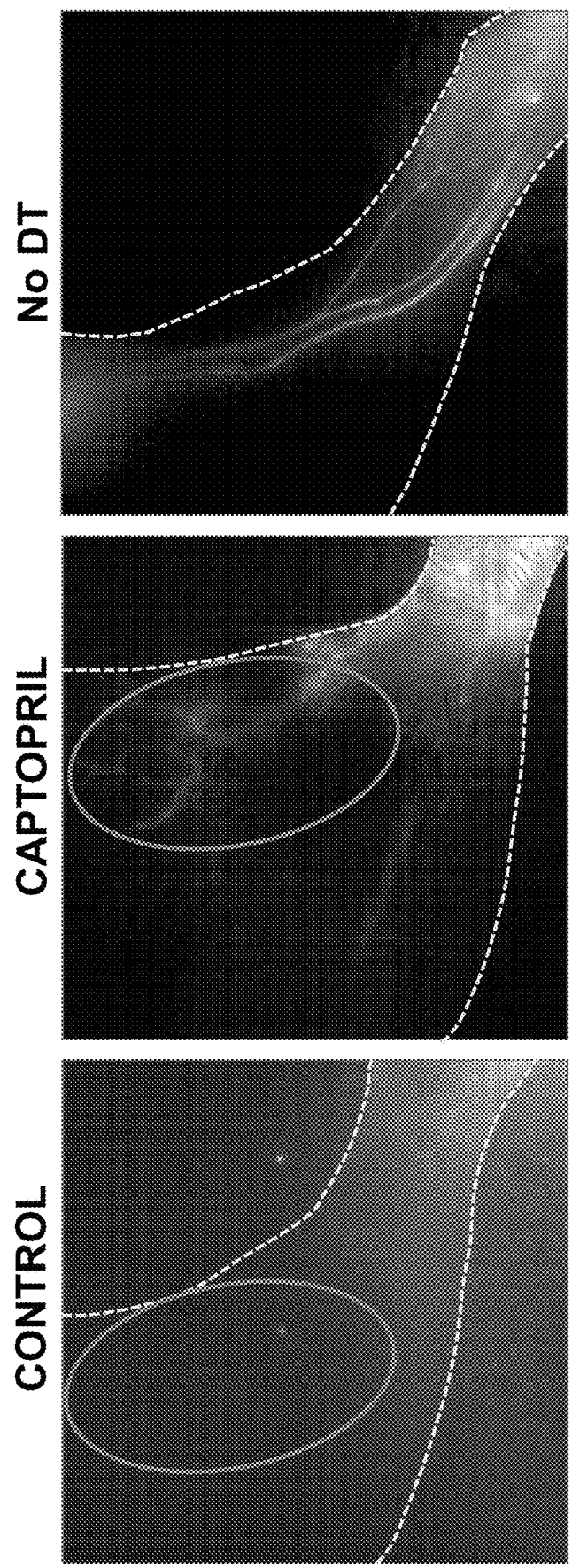
FIG. 42 shows that captopril treatment increases formation of collateral lymphatics after hind limb lymphatic ablation with DT. Representative ICG photographs of control (left panel), Captopril (middle), and normal lymphatic architecture (i.e., no DT treatment) hind limbs are shown. Dotted circle represents area in which collateral lymphatics form to drain into inguinal lymph nodes.
Figure 43:
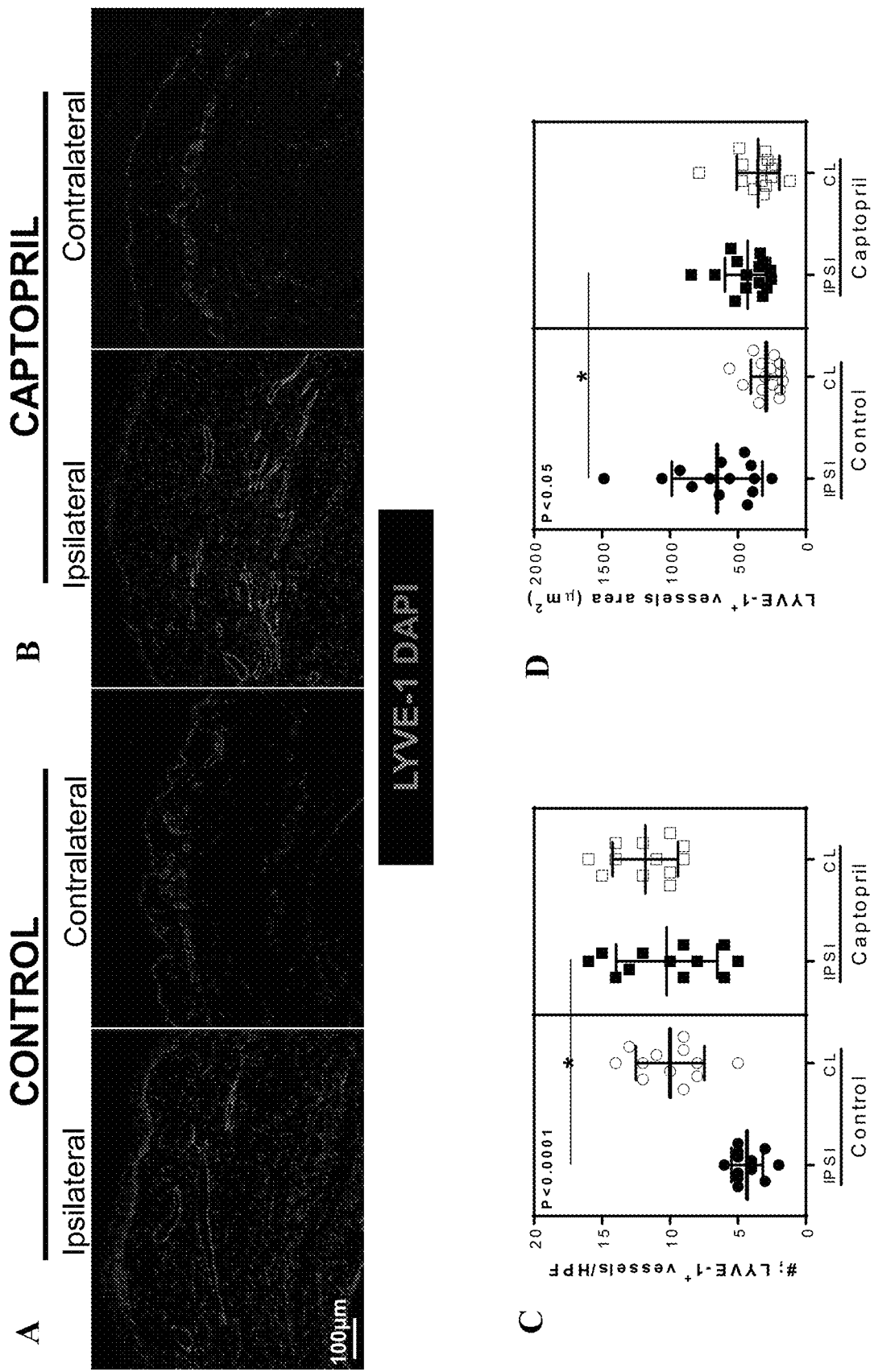
FIG. 43 shows that captopril treatment decreases hind limb lymphangiogenesis after lymphatic ablation with DT. Representative high power photomicrograph of control (A) and captopril treated (B) mouse hind limb sections stained for LYVE-1 (lymphatic marker). Nuclear counterstain is shown with DAPI. (C) shows quantification of LYVE-1+ lymphatic vessels in hind limb tissues of control and captopril treated mice. Note significant difference (*p<0.0001) between ipsilateral control and ipsilateral captopril limbs. (D) shows quantification of LYVE-1+ lymphatic vessel area in hind limb tissues of control and captopril treated mice. Note significant decrease (*p<0.005) between ipsilateral control and ipsilateral captopril limbs.
Figure 44:
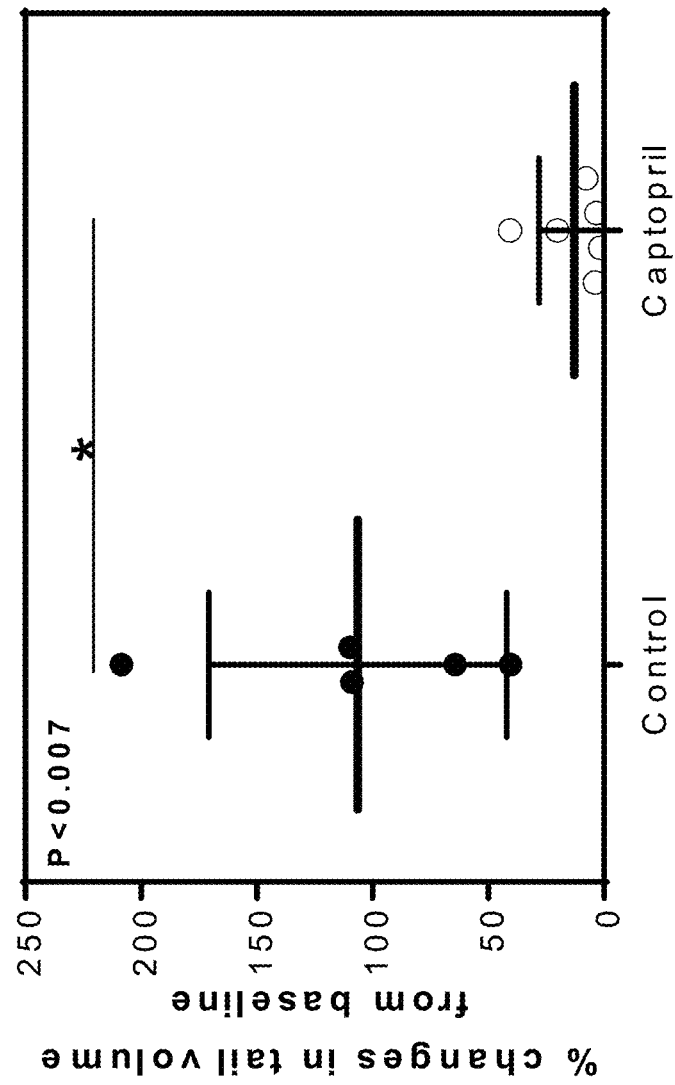
FIG. 44 shows that captopril treatment decreases limb volumes after hind limb lymphatic ablation with DT. Quantification of hind limb volumes in control and captopril treated mice after lymphatic ablation with DT. Note marked decrease in captopril treated mice (*p<0.007).
Figure 45:
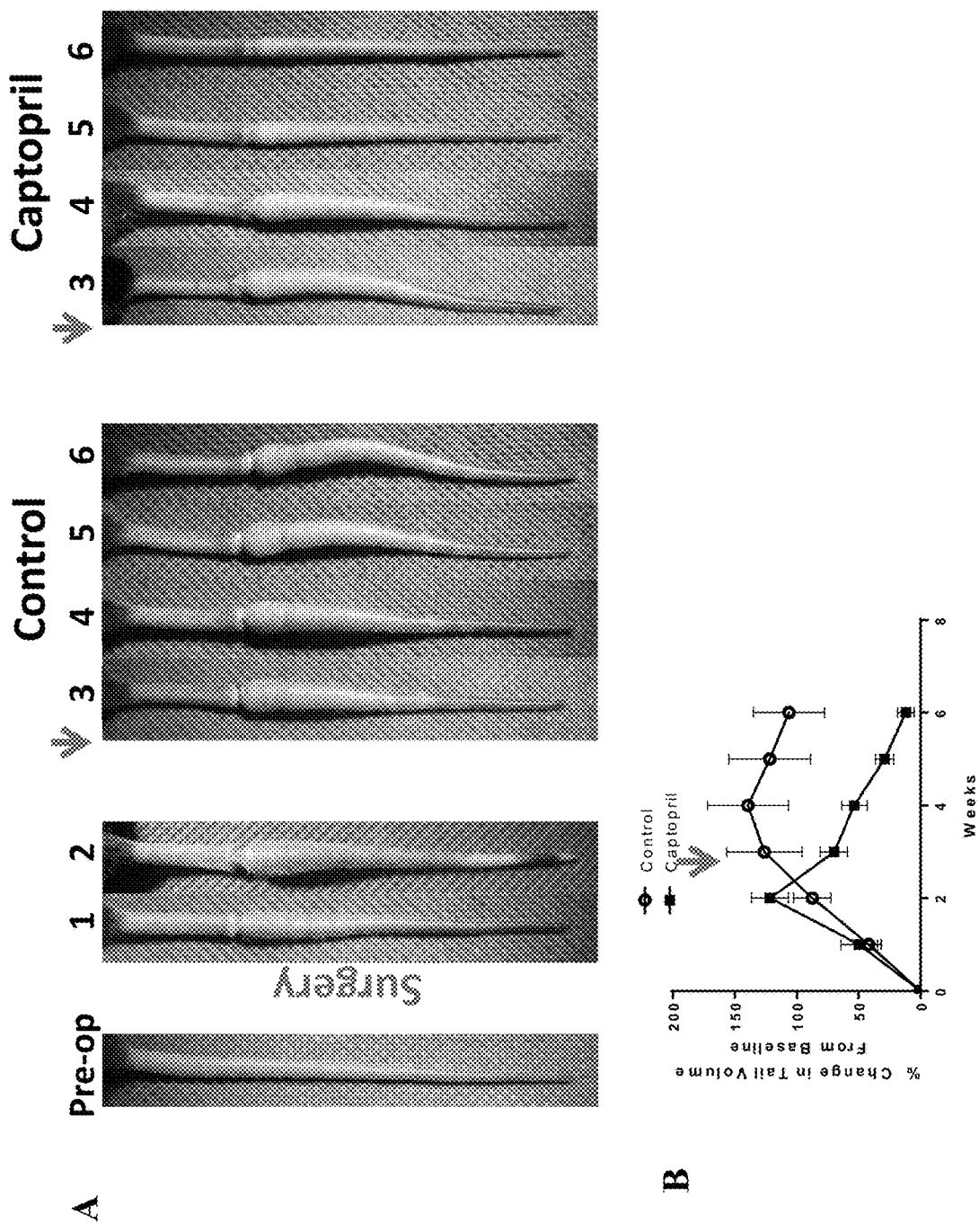
FIG. 45 shows that captopril treatment decreases mouse tail lymphedema 6 weeks after lymphatic ablation. (A) shows representative photographs of mouse tails pre-op and weekly, following lymphatic ablation and treatment with vehicle control or captopril. Arrows indicate timing of treatment initiation. (B) shows quantification of change in mouse tail volumes in control and captopril treated mice.
Figure 47:
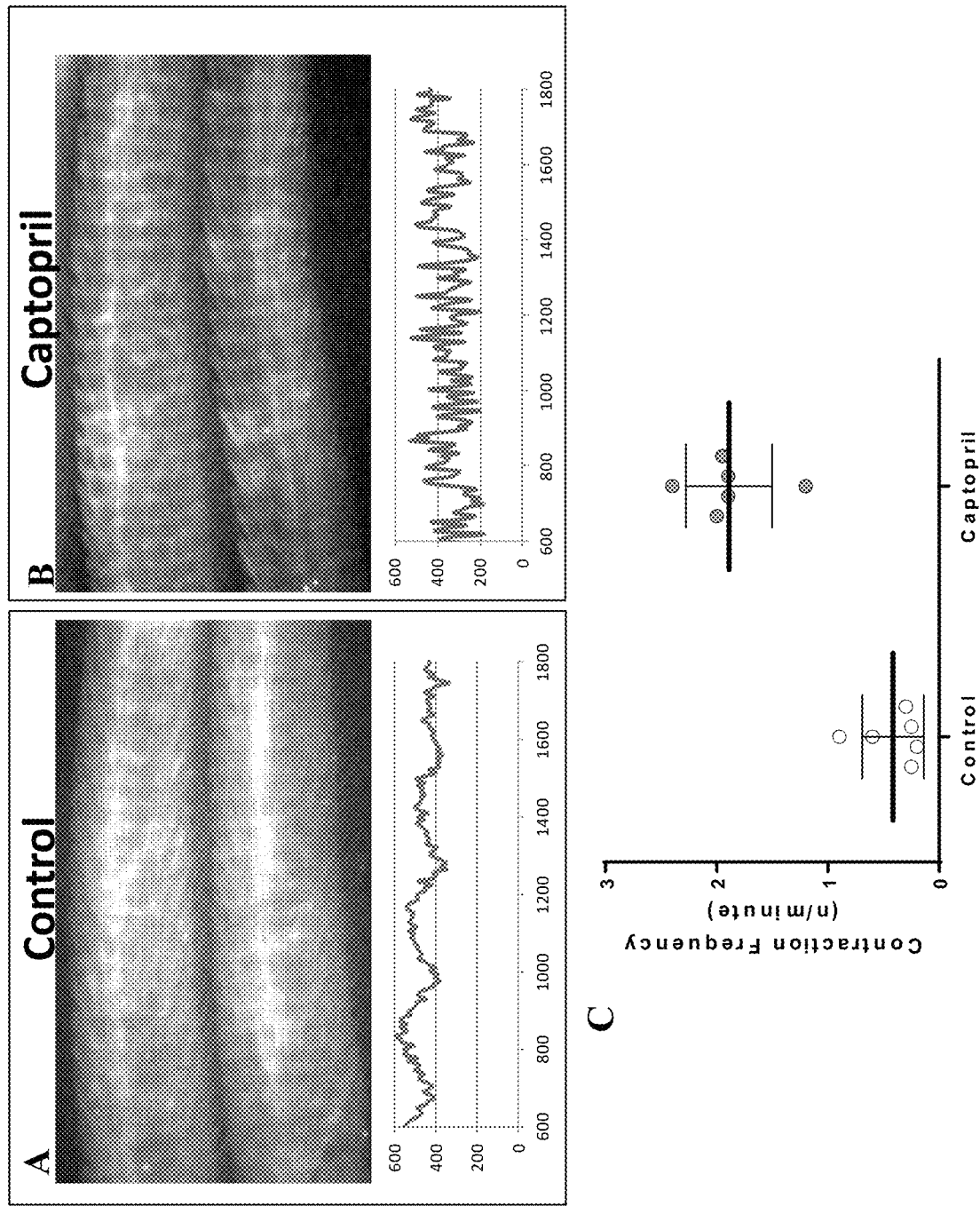
FIG. 47 shows that captopril treatment increases mouse tail collecting vessel pumping frequency 6 weeks after lymphatic ablation. Representative photographs of indocyanine green analysis (top) of mouse tails treated with control (A) or captopril ointment (B) topically for 6 weeks are shown. Line graphs representing collecting lymphatic contractions are shown below the photographs. Note increased number of contractions in captopril treated animals. (C) shows quantification of contraction frequency or mouse tail collecting lymphatics in control and captopril treated animals. Note increase frequency in captopril treated mice (*p<0.01).
Figure 48:
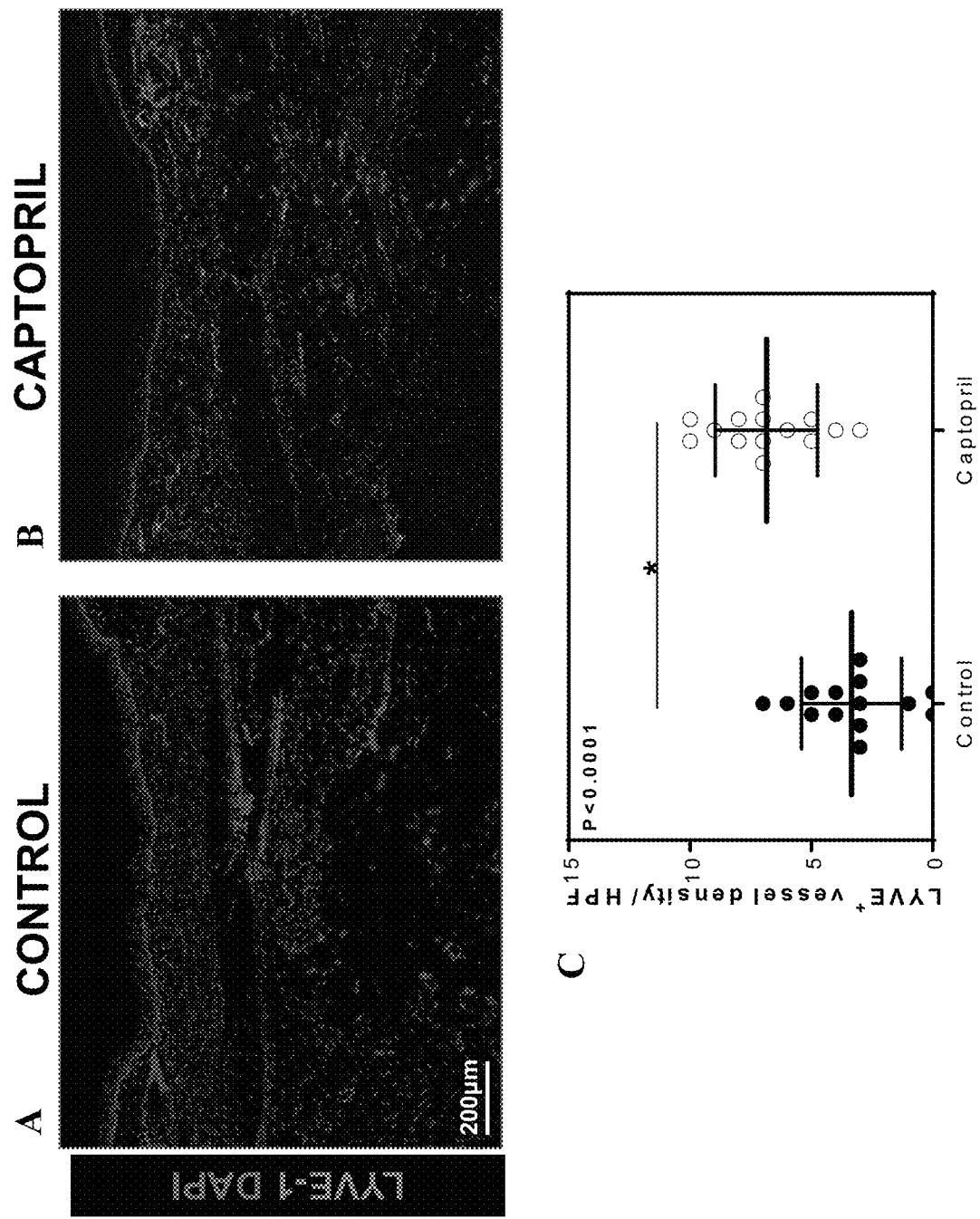
FIG. 48 shows that captopril treatment increases the number of lymphatic vessels crossing the region of the tail wound in the mouse tail model of lymphedema 6 weeks after lymphatic ablation. Representative longitudinal sections of the mouse tails in control (A) and captopril (B) treated animals stained for LYVE-1 (a lymphatic marker) are shown. (C) shows quantification of the LYVE-1+ vessel density in control and captopril treated mice 6 weeks after tail lymphatic ablation.
Figure 50:
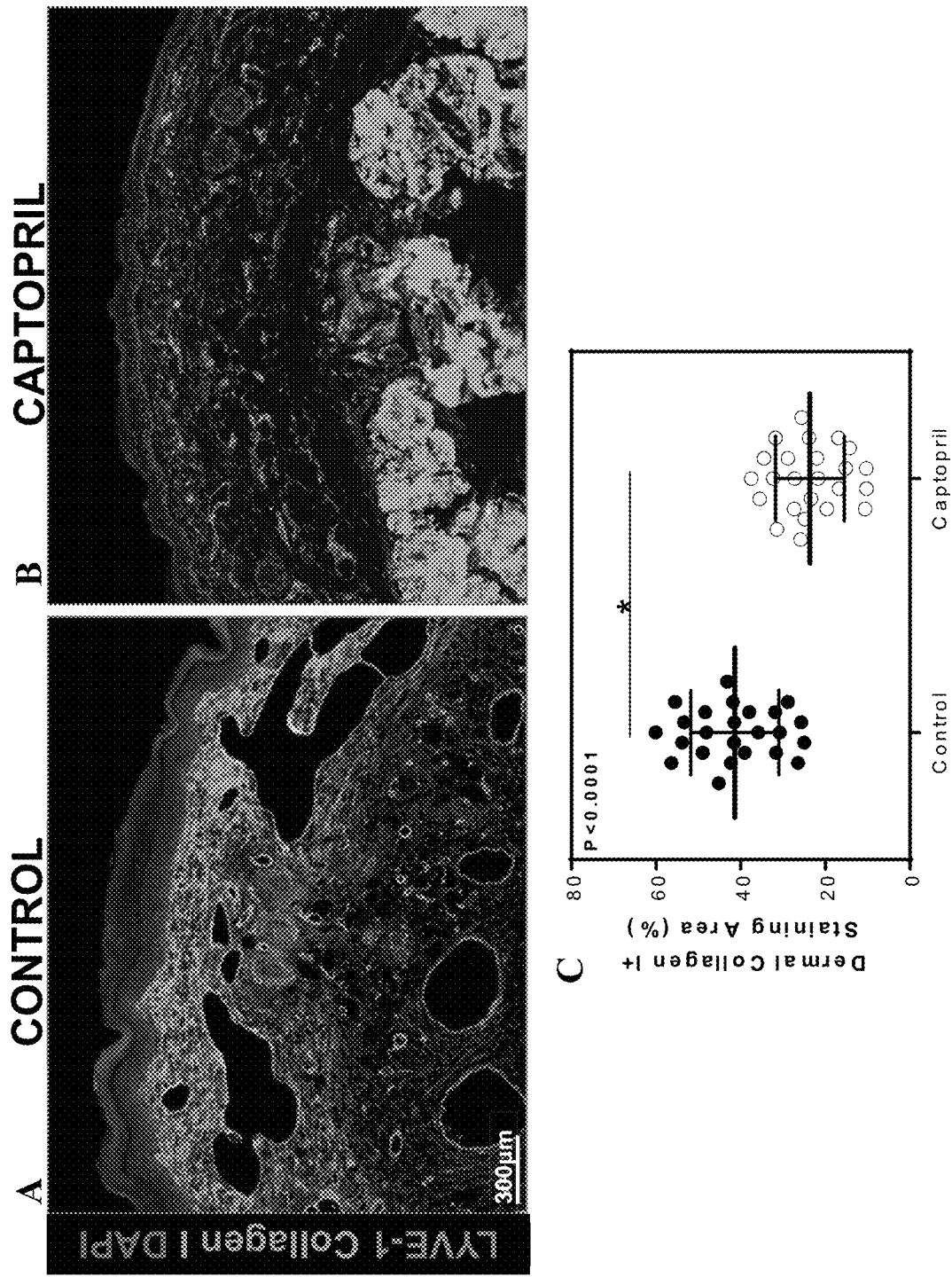
FIG. 50 shows that captopril treatment decreases dermal fibrosis and type I collagen deposition in the mouse tail model of lymphedema 6 weeks after lymphatic ablation. Representative cross sections of the mouse tails in control (A) and captopril (B) treated animals stained for type I collagen, LYVE-1, and DAPI are shown. Note decreased fibrosis in captopril treated animals. (C) shows quantification of mouse tail dermal type I collagen staining area in control and captopril treated mice. Note significant decrease in captopril treated animals (*p<0.0001).
Figure 51:
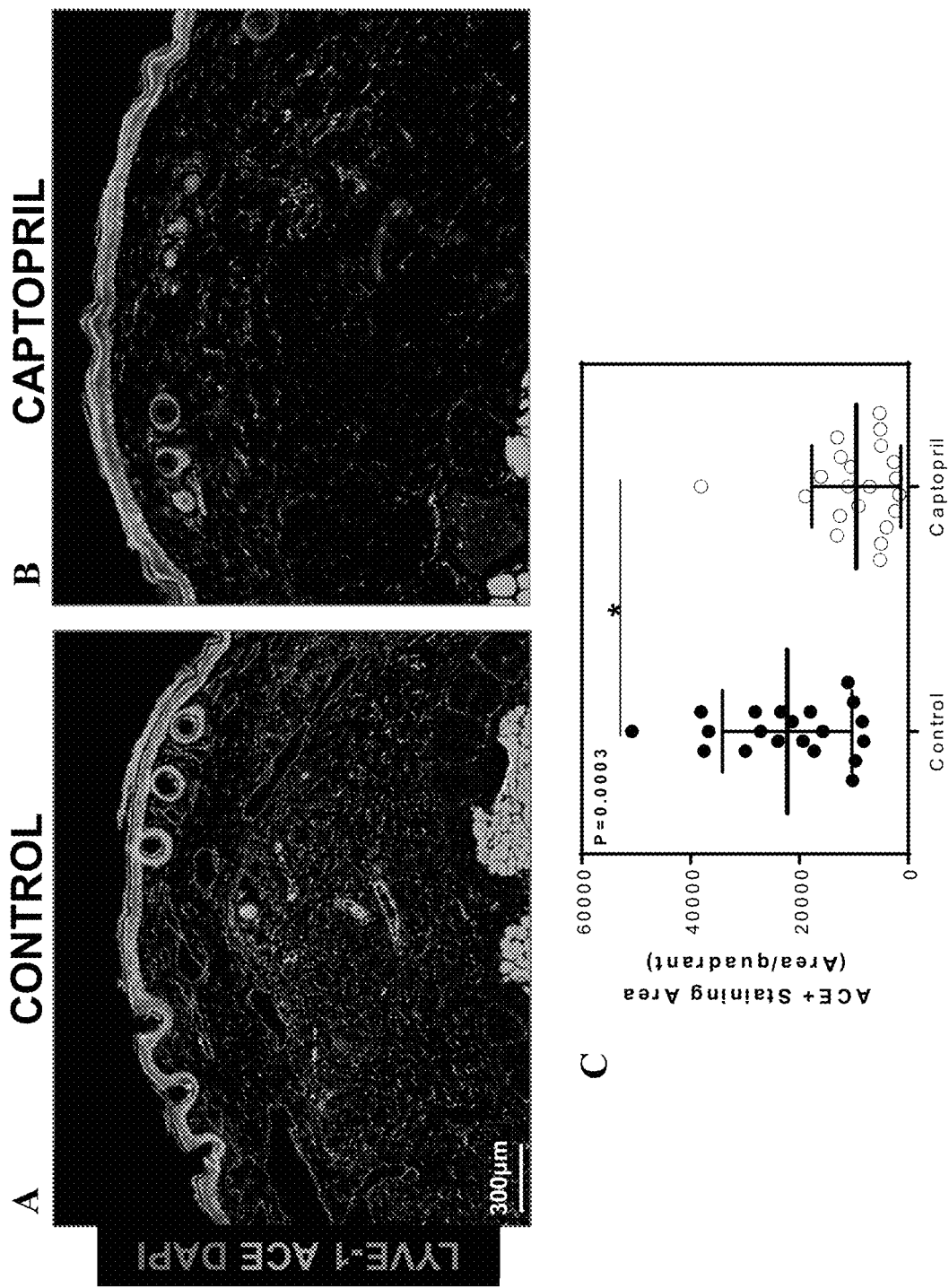
FIG. 51 shows that captopril treatment decreases angiotensin converting enzyme (ACE) expression in the mouse tail model of lymphedema 6 weeks after lymphatic ablation. Representative cross sections of the mouse tails in control (A) and captopril (B) treated animals stained for ACE, LYVE-1, and DAPI are shown. Note decreased ACE expression in captopril treated animals. (C) shows quantification of mouse tail ACE staining area in control and captopril treated mice. Note significant decrease in captopril treated animals (*p<0.0001).
Figure 52:
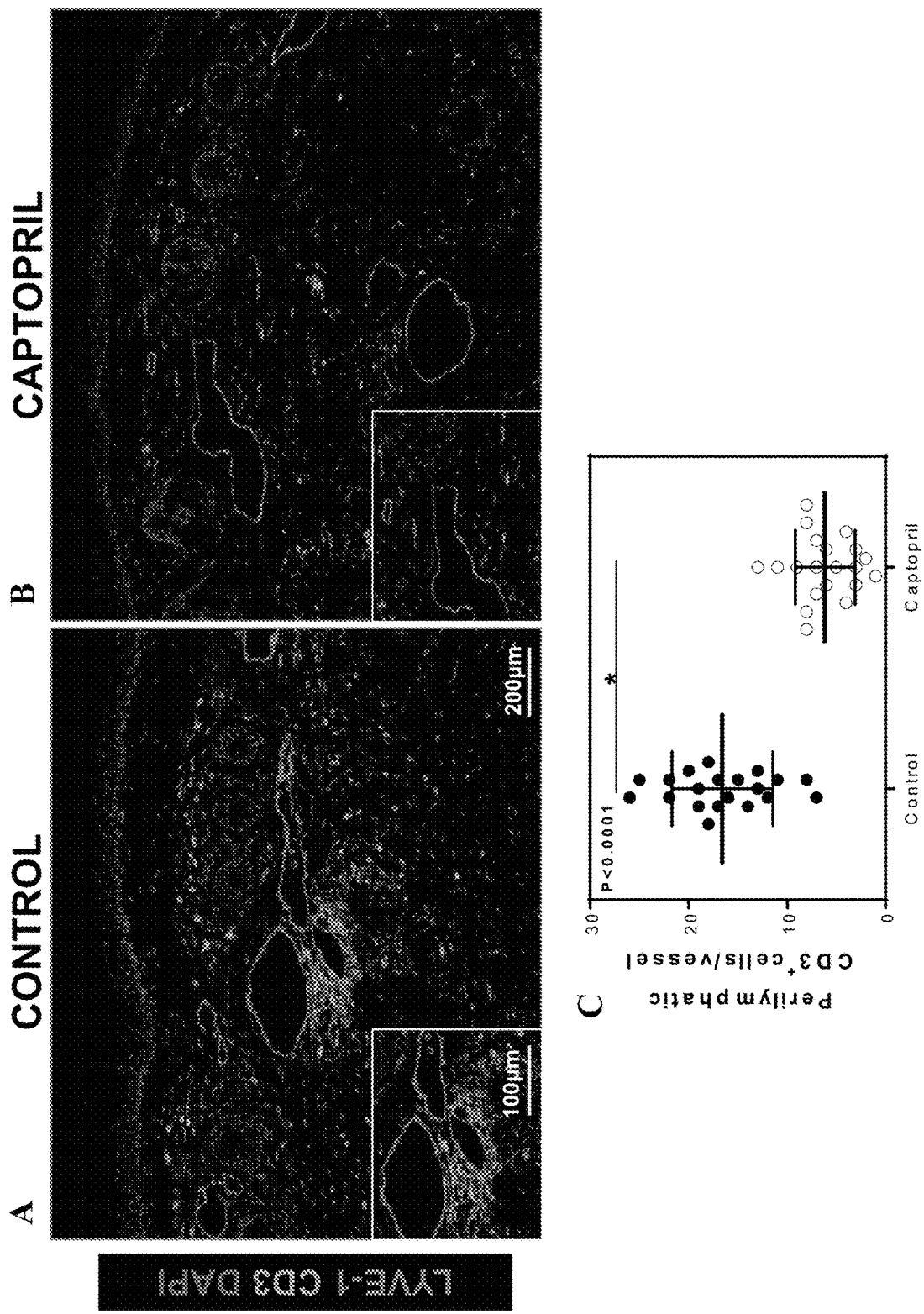
FIG. 52 shows that captopril treatment decreases perilymphatic accumulation of T cells (CD3+) in the mouse tail model of lymphedema 6 weeks after lymphatic ablation. Representative cross sections of the mouse tails in control (A) and captopril (B) treated animals stained for CD3, LYVE-1, and DAPI are shown. Note decreased ACE expression in captopril treated animals. (C) shows quantification of mouse tail perilymphatic CD3+ cells/vessel in control and captopril treated mice. Note significant decrease in captopril treated animals (*p<0.0001).
Figure 53:
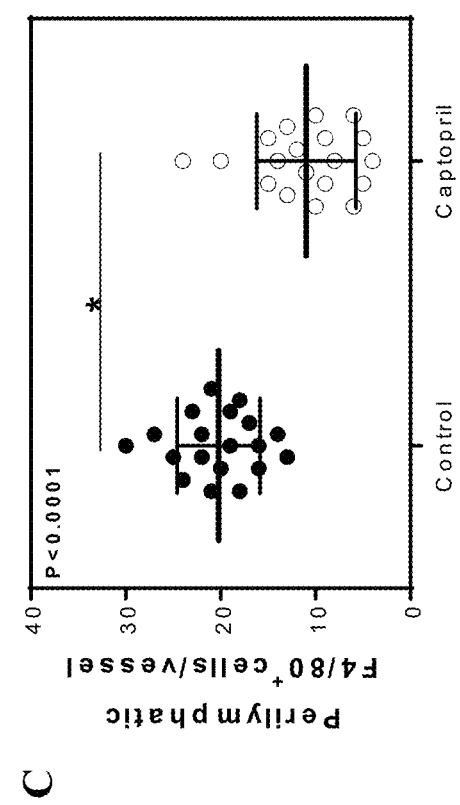
FIG. 53 shows that captopril treatment decreases perilymphatic accumulation of macrophages (F4/80+ cells) in the mouse tail model of lymphedema 6 weeks after lymphatic ablation. Representative cross sections of the mouse tails in control (A) and captopril (B) treated animals stained for F4/80, LYVE-1, and DAPI are shown. Note decreased ACE expression in captopril treated animals. (C) shows quantification of mouse tail perilymphatic F4/80 cells/vessel in control and captopril treated mice. Note significant decrease in captopril treated animals (*p<0.0001).

Collecting lymphatic vessels propagate lymph proximally using active contraction by surrounding smooth muscle cells and one way valves to prevent backflow. Consistent with our finding that teriflunomide increases lymphatic transport function and decreases fibrosis/proliferation of alpha smooth muscle cells surrounding lymphatic vessels, we found that this treatment also markedly increased collecting lymphatic pumping (FIG. 30 (A), (B)). Teriflunomide treatment after PLND nearly doubled the frequency of the main hind limb collecting lymphatics thereby increasing proximal propagation of lymphatic fluid.

We describe for the first time the use of teriflunomide for prevention and treatment of lymphedema. Our findings show that treatment with teriflunomide after lymphatic injury substantially decreases lymphedema and fibroadipose tissue deposition. In addition, we show that this effect correlates with decreased infiltration of CD4+ T cells, increased formation of collateral lymphatics, decreased lymphatic leakiness, and improved lymphatic function. These findings are novel since they provide a targeted therapy for lymphedema, a disease that has previously been treated only with palliative interventions.

Example 4. Treatment and Prevention of Lymphedema Using Captopril

As described above, we tested the efficacy of captopril in preventing lymphatic dysfunction after lymphatic injury using the PLNID model, and in treating established lymphedema using the mouse tail model. Animals were treated with a topical formulation of captopril (5%) or vehicle control petroleum jelly or Aquaphor/glycerin ointment) once daily for 24 weeks (2 weeks after PLND; 4 weeks after tail lymphedema). Mice were then sacrificed and lymphatic function, fibrosis, and lymphangiogenesis were all assessed using standard assays. Treatment with topical captopril resulted in improved lymphatic function in the PLND model and in decreased lymphedema in the tail model. Results are shown in FIGS. 31-53.

Example 5. Treatment and Prevention of Lymphedema Using Drug Combinations

Using the PLND and mouse tail models, as described in Examples 1-4, animals are administered a topical formulation comprising a combination of anti-fibrosis drugs or a vehicle control. Treatment compositions are shown in Table 1.

TABLE 1

Drug Combinations for Treatment and Prevention of Lymphedema

| Composition | Components | Conc. | Composition | Components | Conc. |
|---|---|---|---|---|---|
| A1 | tacrolimus | 0.1% | F1 | tacrolimus | 0.1% |
|    | pirfenidone | 1 mg/ml |    | captopril | 5% |
| A2 | tacrolimus | 0.05% | F2 | tacrolimus | 0.05% |
|    | pirfenidone | 0.5 mg/ml |    | captopril | 2.5% |
| B1 | tacrolimus | 0.1% | G1 | tacrolimus | 0.1% |
|    | pirfenidone | 1 mg/ml |    | pirfenidone | 1 mg/ml |
|    | teriflunomide | 27 mg/ml |    | leflunomide | 10% |
| B2 | tacrolimus | 0.05% | G2 | tacrolimus | 0.05% |
|    | pirfenidone | 0.5 mg/ml |    | pirfenidone | 0.5 mg/ml |
|    | teriflunomide | 13.5 mg/ml |    | leflunomide | 5% |
| C1 | teriflunomide | 27 mg/ml | H1 | leflunomide | 10% |
|    | pirfenidone | 1 mg/ml |    | pirfenidone | 1 mg/ml |
| C2 | teriflunomide | 13.5 mg/ml | H2 | leflunomide | 5% |
|    | pirfenidone | 0.5 mg/ml |    | pirfenidone | 0.5 mg/ml |
| D1 | tacrolimus | 0.1% | I1 | tacrolimus | 0.1% |
|    | captopril | 5% |    | captopril | 5% |
|    | teriflunomide | 27 mg/ml |    | leflunomide | 10% |
| D2 | tacrolimus | 0.05% | I2 | tacrolimus | 0.05% |
|    | captopril | 2.5% |    | captopril | 2.5% |
|    | teriflunomide | 13.5 mg/ml |    | leflunomide | 5% |
| E1 | teriflunomide | 27 mg/ml | J1 | leflunomide | 10% |
|    | captopril | 5% |    | captopril | 5% |
| E2 | teriflunomide | 13.5 mg/ml | J2 | leflunomide | 5% |
|    | captopril | 2.5% |    | captopril | 2.5% |

Mice are treated once daily for 2-4 weeks (2 weeks after PLND; 4 weeks after tail lymphedema). Mice are then sacrificed and lymphatic function, fibrosis, lymphangiogenesis are assessed using standard assays. In the PLND model, treatment with a combination of topical anti-fibrosis drugs results in improved lymphatic function compared to treatment with a single anti-fibrosis drug. Likewise, in the tail model, treatment with a combination of topical anti-fibrosis drugs results in decreased lymphedema compared to treatment with a single anti-fibrosis drug. In addition to being more effective, the combination produces synergistic effects, such that the effective dose of each drug administered in the combination is lower than the effective dose of each drug administered alone.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The present invention is further described by the following claims.

We claim:

1. A method of preventing lymphedema, the method comprising administering to a cancer patient undergoing radiation therapy, chemotherapy, and/or surgical lymph node dissection a pharmaceutical composition comprising an effective amount of pirfenidone, wherein the pharmaceutical composition is administered prophylactically within about six weeks of the radiation therapy, chemotherapy, and/or surgical lymph node dissection, and wherein lymphedema is prevented in the cancer patient.

2. The method of claim 1, wherein the pharmaceutical composition is administered topically.

3. The method of claim 2, wherein the pharmaceutical composition is in a form selected from the group consisting of an ointment, a cream, a lotion, a paste, a gel, a mousse, a foam, a lacquer, a suspension, a liquid, and a spray.

4. The method of claim 3, wherein the pharmaceutical composition is in the form of an ointment.

5. The method of claim 2, wherein the pharmaceutical composition is administered at least once a day.

6. The method of claim 2, wherein the pharmaceutical composition is administered at least twice a day.

7. The method of claim 1, wherein the pharmaceutical composition is administered orally.

8. The method of claim 7, wherein the pharmaceutical composition is in a form selected from the group consisting of a tablet, a capsule, a liquid, a solution, a softgel, a suspension, an emulsion, a syrup, and an elixir.

9. The method of claim 8, wherein the pharmaceutical composition is in the form of a tablet or a capsule.

10. The method of claim 7, wherein the pharmaceutical composition is administered at least once a day.

11. The method of claim 7, wherein the pharmaceutical composition is administered at least twice a day.

12. The method of claim 1, wherein the pharmaceutical composition is administered prophylactically within about two weeks of the radiation therapy, chemotherapy, and/or surgical lymph node dissection.

13. The method of claim 1, wherein the pharmaceutical composition is administered prophylactically within about one week of the radiation therapy, chemotherapy, and/or surgical lymph node dissection.

14. The method of claim 13, wherein the pharmaceutical composition is administered prophylactically about one week before the radiation therapy, chemotherapy, and/or surgical lymph node dissection.

15. The method of claim 13, wherein the pharmaceutical composition is administered prophylactically about 1, 2, 3, 4, 5, or 6 days before the radiation therapy, chemotherapy, and/or surgical lymph node dissection.

16. The method of claim 13, wherein the pharmaceutical composition is administered prophylactically on the same day as the radiation therapy, chemotherapy, and/or surgical lymph node dissection.

* * * * *